(12) United States Patent
Ochiai et al.

(10) Patent No.: US 9,857,683 B2
(45) Date of Patent: Jan. 2, 2018

(54) COMPOUND, RESIN, RESIST COMPOSITION AND METHOD FOR PRODUCING RESIST PATTERN

(71) Applicant: SUMITOMO CHEMICAL COMPANY, LIMITED, Tokyo (JP)

(72) Inventors: Mitsuyoshi Ochiai, Osaka (JP); Shota Nakano, Osaka (JP); Koji Ichikawa, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/936,924

(22) Filed: Nov. 10, 2015

(65) Prior Publication Data
US 2016/0131971 A1  May 12, 2016

(30) Foreign Application Priority Data

Nov. 11, 2014 (JP) ................................. 2014-228567

(51) Int. Cl.
| | | |
|---|---|---|
| *G03F 7/004* | (2006.01) | |
| *G03F 7/38* | (2006.01) | |
| *C07C 69/653* | (2006.01) | |
| *C07C 69/74* | (2006.01) | |
| *C08F 220/24* | (2006.01) | |
| *G03F 7/039* | (2006.01) | |
| *G03F 7/20* | (2006.01) | |
| *C08F 220/18* | (2006.01) | |
| *C08F 220/22* | (2006.01) | |
| *C08K 5/42* | (2006.01) | |
| *C08F 220/28* | (2006.01) | |

(52) U.S. Cl.
CPC .......... *G03F 7/0392* (2013.01); *C07C 69/653* (2013.01); *C07C 69/74* (2013.01); *C08F 220/18* (2013.01); *C08F 220/22* (2013.01); *C08F 220/24* (2013.01); *C08K 5/42* (2013.01); *G03F 7/004* (2013.01); *G03F 7/0397* (2013.01); *G03F 7/20* (2013.01); *G03F 7/38* (2013.01); *C08F 2220/1858* (2013.01); *C08F 2220/1875* (2013.01); *C08F 2220/1891* (2013.01); *C08F 2220/281* (2013.01); *C08F 2220/283* (2013.01)

(58) Field of Classification Search
CPC ....... G03F 7/0397; G03F 7/38; C07C 69/653; C07C 69/74; C08F 220/24
USPC ..... 430/270.1, 326, 907, 910; 560/126, 220, 560/223; 526/242, 245, 270, 281, 284, 526/321
See application file for complete search history.

(56) References Cited

U.S. PATENT DOCUMENTS

| | | | |
|---|---|---|---|
| 3,779,778 | A | 12/1973 | Smith et al. |
| 3,849,137 | A | 11/1974 | Barzynski et al. |
| 4,576,902 | A | 3/1986 | Saenger et al. |
| 4,822,716 | A | 4/1989 | Onishi et al. |
| 4,857,437 | A | 8/1989 | Banks et al. |
| 5,017,453 | A | 5/1991 | Onishi et al. |
| 5,073,476 | A | 12/1991 | Meier et al. |
| 5,198,520 | A | 3/1993 | Onishi et al. |

(Continued)

FOREIGN PATENT DOCUMENTS

| | | |
|---|---|---|
| DE | 39 14 407 A1 | 10/1990 |
| EP | 0 126 712 A1 | 11/1984 |
| JP | 55-164824 A | 12/1980 |
| JP | 62-069263 A | 3/1987 |
| JP | 62-153853 A | 7/1987 |
| JP | 63-026653 A | 2/1988 |
| JP | 63-146029 A | 6/1988 |
| JP | 63-146038 A | 6/1988 |
| JP | 63-163452 A | 7/1988 |
| JP | 01-305052 A | 12/1989 |
| JP | 2000-122294 A | 4/2000 |
| JP | 2008-209917 A | 9/2008 |
| JP | 2010-032994 A | 2/2010 |
| JP | 2010-061117 A | 3/2010 |
| JP | 2010-204634 A | 9/2010 |

(Continued)

OTHER PUBLICATIONS

Luis et al., "Non Concerted Pathways in the Generation of Dehydroarenes by Thermal Decomposition of Diaryliodonium Carboxylates", Tetrahedron vol. 45, No. 19, pp. 6281 to 6296, 1989.

(Continued)

*Primary Examiner* — John S Chu
(74) *Attorney, Agent, or Firm* — Birch, Stewart, Kolasch & Birch, LLP

(57) ABSTRACT

A resist composition includes (A1) a resin having an acid-labile group, (A2) a resin which includes a structural unit represented by formula (I), and an acid generator:

(I)

wherein $R^1$ represents a hydrogen atom, a halogen atom or a $C_1$ to $C_6$ alkyl group in which a hydrogen atom can be replaced by a halogen atom, $R^2$ represents a $C_1$ to $C_{12}$ fluorinated saturated hydrocarbon group, $A^1$ represents a $C_2$ to $C_6$ alkanediyl group or $\ast\text{-}A^2\text{-}X^1\text{-}(A^3\text{-}X^2)_a\text{-}A^4{}_b\text{-}$, $\ast$ represents a binding site to an oxygen atom in —O—CO—, $A^2$, $A^3$ and $A^4$ each independently represent a $C_1$ to $C_6$ alkanediyl group, $X^1$ and $X^2$ each independently represent —O—, —CO—O— or —O—CO—, and "a" represents 0 or 1.

8 Claims, No Drawings

(56) References Cited

U.S. PATENT DOCUMENTS

| | | |
|---|---|---|
| 5,260,410 A | 11/1993 | Schwalm |
| 5,453,341 A | 9/1995 | Schwalm |
| 8,835,098 B2* | 9/2014 | Fukuhara ............. G03F 7/0046 430/270.1 |
| 2002/0098441 A1 | 7/2002 | Okino et al. |
| 2003/0149225 A1 | 8/2003 | Okino et al. |
| 2004/0043324 A1 | 3/2004 | Okino et al. |
| 2005/0031990 A1 | 2/2005 | Okino et al. |
| 2005/0031991 A1 | 2/2005 | Okino et al. |
| 2005/0037283 A1 | 2/2005 | Okino et al. |
| 2005/0037284 A1 | 2/2005 | Okino et al. |
| 2005/0048400 A1 | 3/2005 | Okino et al. |
| 2008/0193874 A1 | 8/2008 | Takata et al. |
| 2009/0197204 A1 | 8/2009 | Shiono et al. |
| 2010/0035180 A1 | 2/2010 | Shimada et al. |
| 2010/0151380 A1 | 6/2010 | Ando et al. |
| 2010/0203446 A1 | 8/2010 | Ichikawa et al. |
| 2011/0171576 A1 | 7/2011 | Yamaguchi et al. |
| 2011/0200935 A1 | 8/2011 | Masuyama et al. |
| 2011/0201823 A1 | 8/2011 | Yoshida et al. |
| 2012/0077125 A1 | 3/2012 | Shiono et al. |
| 2012/0328986 A1 | 12/2012 | Anryu et al. |
| 2013/0143157 A1 | 6/2013 | Tanaka et al. |
| 2014/0272707 A1* | 9/2014 | Fukushima ........... C08F 220/24 430/270.1 |
| 2014/0287360 A1* | 9/2014 | Nakamura ............. G03F 7/038 430/281.1 |
| 2014/0322652 A1* | 10/2014 | Komuro ............... G03F 7/0397 430/283.1 |

FOREIGN PATENT DOCUMENTS

| | | |
|---|---|---|
| JP | 2010-204646 A | 9/2010 |
| JP | 2011-039502 A | 2/2011 |
| JP | 2011-191745 A | 9/2011 |
| JP | 2012-006908 A | 1/2012 |
| JP | 2012-041274 A | 3/2012 |
| JP | 2012-072109 A | 4/2012 |
| JP | 2012-229206 A | 11/2012 |

OTHER PUBLICATIONS

Zhang et al., "Synthesis, characterization and properties of a novel fluorinated methacrylate polymer," Journal of Fluorine Chemistry, vol. 132, 2011, pp. 915-919.

* cited by examiner

COMPOUND, RESIN, RESIST COMPOSITION AND METHOD FOR PRODUCING RESIST PATTERN

CROSS-REFERENCE TO RELATED APPLICATIONS

This application claims priority to Japanese Application No. 2014-228567 filed on Nov. 11, 2014. The entire disclosures of Japanese Application No. 2014-228567 is incorporated hereinto by reference.

BACKGROUND OF THE INVENTION

1. Field of the Invention

The disclosure relates to a compound, a resin, a resist composition and a method for producing resist pattern.

2. Related Art

A compound is described in Patent document of JP H01-305052 as below.

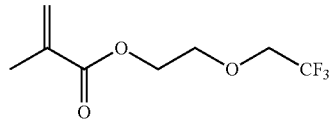

A resin having a structural unit below is described in non-Patent document of Journal of Fluorine Chemistry 132 (2011) 915-919.

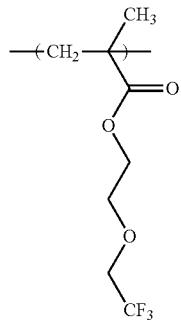

A resist composition containing a resin (AX2-1) having a structural unit below and a resin (AX2-2) having a structural unit below is described in Patent document of JP2010-32994A.

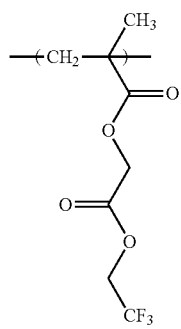
(AX2-1)

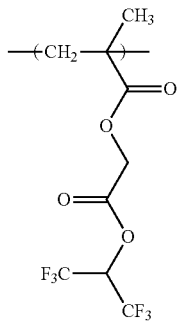
(AX2-1)

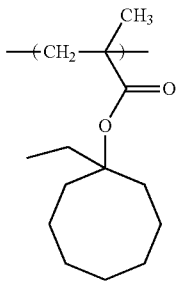

SUMMARY

The disclosure provides following inventions of <1> to <8>.

<1> A resist composition which contains
(A1) a resin having an acid-labile group,
(A2) a resin which includes a structural unit represented by formula (I), and
an acid generator:

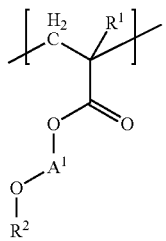
(I)

wherein $R^1$ represents a hydrogen atom, a halogen atom or a $C_1$ to $C_6$ alkyl group in which a hydrogen atom can be replaced by a halogen atom, $R^2$ represents a $C_1$ to $C_{12}$ fluorinated saturated hydrocarbon group, $A^1$ represents a $C_2$ to $C_6$ alkanediyl group or *-$A^2$-$X^1$-$(A^3$-$X^2)_a$-$A^4$-,

* represents a binding site to an oxygen atom in —O—CO—, $A^2$, $A^3$ and $A^4$ each independently represent a $C_1$ to $C_6$ alkanediyl group, $X^1$ and $X^2$ each independently represent —O—, —CO—O— or —O—CO—, and "a" represents 0 or 1.

<2> The resist composition according to <1>, wherein $A^1$ represents a $C_2$ to $C_6$ alkanediyl group.

<3> The resist composition according to <1> or <2>, wherein the resin (A2) has 50% by mole or more of the structural unit represented by formula (I).

<4> The resist composition according to any one of <1> to <3>, wherein the resin (A2) is contained in the amount of 0.5 to 60 parts by mass with respect to 100 part by mass of the resin (A1).

<5> The resist composition according to any one of <1> to <4>, further containing a salt which generates an acid weaker in acidity than an acid generated from the acid generator.

<6>. A method for producing a resist pattern including steps (1) to (5);
(1) applying the resist composition according to any one of <1> to <5> onto a substrate;
(2) drying the applied composition to form a composition layer;
(3) exposing the composition layer;
(4) heating the exposed composition layer, and
(5) developing the heated composition layer.
<7> A compound represented by formula (Ia):

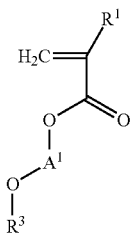

wherein $R^1$ represents a hydrogen atom, a halogen atom or a $C_1$ to $C_6$ alkyl group in which a hydrogen atom can be replaced by a halogen atom, $R^3$ represents $—CH(R^{f1})(R^{f2})$, $R^{f1}$ and $R^{f2}$ each independently represent a $C_1$ to $C_6$ perfluoroalkyl group, $A^1$ represents a $C_2$ to $C_6$ alkanediyl group or $*-A^2-X^1-(A^3-X^2)_a-A^4-$,

* represents a bonding site to an oxygen atom in $—O—CO—$, $A^2$, $A^3$ and $A^4$ each independently represent a $C_1$ to $C_6$ alkanediyl group, $X^1$ and $X^2$ each independently represent $—O—$, $—CO—O—$ or $—O—CO—$, and a represents 0 or 1.

<8> A resin has a structural unit derived from the compound according to <7>.

DETAILED DESCRIPTION OF THE PREFERRED EMBODIMENTS

In the specification, the term "(meth)acrylic monomer" means a monomer having a structure of "$CH_2=CH—CO—$" or "$CH_2=C(CH_3)—CO—$", as well as "(meth)acrylate" and "(meth)acrylic acid" mean "an acrylate or methacrylate" and "an acrylic acid or methacrylic acid," respectively. Herein, chain structure groups include those having a linear structure and those having a branched structure. Unless otherwise specified, the term "aliphatic hydrocarbon group" means a chain aliphatic hydrocarbon group. The indefinite articles "a" and "an" are taken as the same meaning as "one or more".

the term "solid components" means components other than solvents in a resist composition.

<Resist Composition>

The resist composition of the disclosure includes a resin having an acid-labile group (which resin is sometimes referred to as "resin (A1)"), a resin which has a structural unit represented by formula (I) described later (which resin is sometimes referred to as "resin (A2)"), and an acid generator (which resin is sometimes referred to as "acid generator (B)").

Here the "acid-labile group" means a group having a leaving group which is detached by contacting with an acid resulting in forming a hydrophilic group such as a hydroxy or carboxy group.

Here, when a resin has both an acid-labile group and the structural unit represented by formula (I), the resin is defined as "resin (A2)".

The resist composition preferably further contains a quencher (which is sometimes referred to as "quencher (C)") and/or a solvent (which is sometimes referred to as "solvent (E)") in addition to the resins (A1) and (A2), and the acid generator. Also, the resist composition may further contain other resin other than the resins (A1) and (A2).

<Resin (A1)>

The resin (A1) has a structural unit having an acid-labile group (which is sometimes referred to as "structural unit (a1)"). The resin (A1) preferably further has a structural unit other than the structural unit (a1). Examples of the structural unit other than the structural unit (a1) include a structural unit having no acid-labile group (which is sometimes referred to as "structural unit (s)", the structural unit (s) does not include the structural unit (I)), a structural unit other than the structural unit (a1) and a structural unit (s) as described later (which is sometimes referred to as "structural unit (t)"), as well as a structural unit derived from a known monomer in the art.

<Structural Unit (a1)>

The structural unit (a1) is derived from a monomer having an acid-labile group (which is sometimes referred to as "monomer (a1)"). Here the "acid-labile group" means a group having a leaving group which is detached by contacting with an acid resulting in forming a hydrophilic group such as a hydroxy or carboxy group.

In the resin (A1), the acid-labile group contained in the structural unit (a1) is preferably the following group (1) and/or group (2):

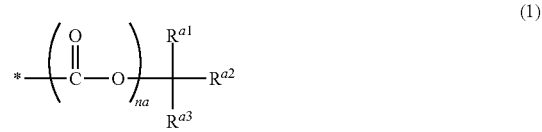

wherein $R^{a1}$ to $R^{a3}$ each independently represent a $C_1$ to $C_8$ alkyl group, a $C_3$ to $C_{20}$ alicyclic hydrocarbon group or a combination thereof, or $R^{a1}$ and $R^{a2}$ may be bonded together with a carbon atom bonded thereto to form a $C_3$ to $C_{20}$ divalent hydrocarbon group;

na represents an integer of 0 or 1; and

* represents a binding site;

wherein $R^{a1'}$ and $R^{a2'}$ each independently represent a hydrogen atom or a $C_1$ to $C_{12}$ hydrocarbon group, $R^{a3'}$ represents a $C_1$ to $C_{20}$ hydrocarbon group, or $R^{a2'}$ and $R^{a3'}$ may be bonded together with a carbon atom and X bonded thereto to form a divalent $C_3$ to $C_{20}$ (or 4 to 21-membered) heterocyclic group, and a methylene group contained in the hydrocarbon group or the divalent heterocyclic group may be replaced by an oxygen atom or a sulfur atom;

X represents —O— or —S—; and

* represents a binding site.

Examples of the alkyl group for $R^{a1}$ to $R^{a3}$ include methyl, ethyl, propyl, n-butyl, n-pentyl, n-hexyl, n-heptyl and n-octyl groups.

Examples of the alicyclic hydrocarbon group for $R^{a1}$ to $R^{a3}$ include monocyclic groups such as a cycloalkyl group, i.e., cyclopentyl, cyclohexyl, cycloheptyl, cyclooctyl groups; and polycyclic groups such as decahydronaphtyl, adamantyl and norbornyl groups as well as the following groups. In each of the formulae, * represents a binding site.

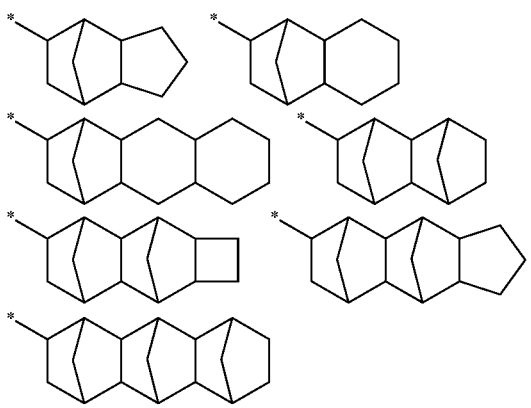

The carbon number of the alicyclic hydrocarbon group for $R_{a1}$ to $R^{a3}$ is preferably 3 to 16.

Examples of groups combining the alkyl group and the alicyclic hydrocarbon group include methyl cyclohexyl, dimethyl cyclohexyl, methyl norbornyl and methyl adamantly, cyclohexylmethyl, methyl cyclohexylmethyl, adamantylmethyl and norbornylmetyl groups.

na is preferably 0.

When $R^{a1}$ and $R^{a2}$ is bonded together to form a divalent hydrocarbon group, examples of the group —C($R^{a1}$)($R^{a2}$)($R^{a3}$) include the following groups. The carbon number of the divalent hydrocarbon group is preferably 3 to 12. In each of the formulae, * represent a binding site to —O—.

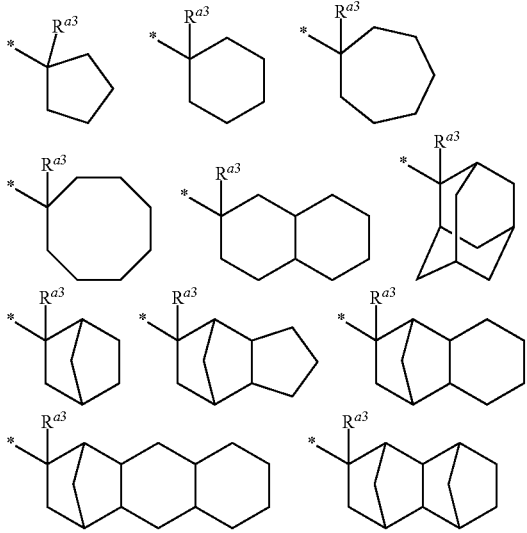

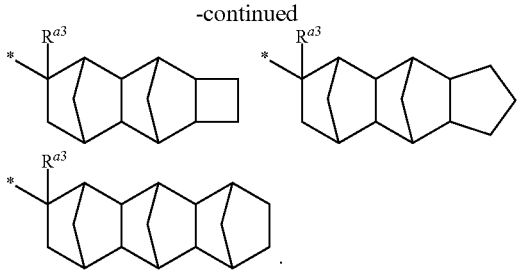

In each formula, $R^{a3}$ is as defined above.

Specific examples of the group represented by the formula (1) include, for example, 1,1-dialkylalkoxycarbonyl group (a group in which $R^{a1}$ to $R^{a3}$ are alkyl groups, preferably tert-butoxycarbonyl group, in the formula (1)), 2-alkyladamantane-2-yloxycarbonyl group (a group in which $R^{a1}$, $R^{a2}$ and a carbon atom form adamantyl group, and $R^{a3}$ is alkyl group, in the formula (1)), and 1-(adamantane-1-yl)-1-alkylalkoxycarbonyl group (a group in which $R^{a1}$ and $R^{a2}$ are alkyl group, and $R^{a3}$ is adamantyl group, in the formula (1)).

The hydrocarbon group for $R^{a1'}$ to $R^{a3'}$ includes any of an alkyl group, an alicyclic hydrocarbon group, an aromatic hydrocarbon group and a group formed by combining thereof.

Examples of the alkyl group and the alicyclic hydrocarbon group are the same examples as described above.

Examples of the aromatic hydrocarbon group include an aryl group such as phenyl, naphthyl, anthryl, p-methylphenyl, p-tert-butylphenyl, p-adamantylphenyl, tolyl, xylyl, cumenyl, mesityl, biphenyl, phenanthryl, 2,6-diethylphenyl and 2-methyl-6-ethylphenyl groups.

Examples of the divalent heterocyclic group formed by binding with $R^{a2'}$ and $R^{a3'}$ with a carbon atom and X bonded thereto include the following groups.

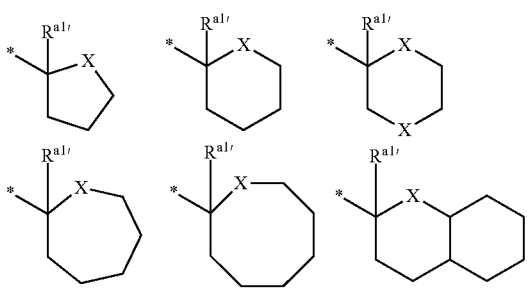

In each formula, $R^{a1'}$ and X are as defined above.

At least one of $R^{a1'}$ and $R^{a2'}$ is preferably a hydrogen atom.

Specific examples of the group represented by the formula (2) include the following groups. In each of the formulae, * represents a binding site.

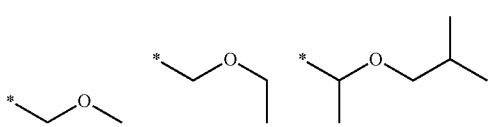

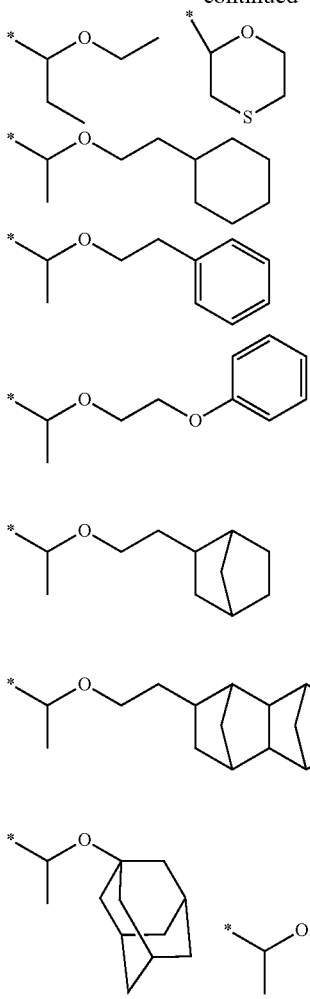

The monomer (a1) is preferably a monomer having an acid-labile group and an ethylenically unsaturated bond, and more preferably a (meth)acrylic monomer having an acid-labile group.

Among the (meth)acrylic monomer having an acid-labile group, a monomer having a $C_5$ to $C_{20}$ alicyclic hydrocarbon group is preferred. When a resin (A1) including a structural unit derived from a monomer (a1) having a bulky structure such as the alicyclic hydrocarbon group is used for a resist composition, the resist composition having excellent resolution tends to be obtained.

Examples of a structural unit derived from the (meth) acrylic monomer having the group represented by the formula (1) preferably include structural units represented by formula (a1-0), formula (a1-1) and formula (a1-2) below. These may be used as a single structural unit or as a combination of two or more structural units. The structural unit represented by formula (a1-0), the structural unit represented by formula (a1-1) and a structural unit represented by formula (a1-2) are sometimes referred to as "structural unit (a1-0)", "structural unit (a1-1)" and "structural unit (a1-2)"), respectively, and monomers inducing the structural unit (a1-0), the structural unit (a1-1) and the structural unit (a1-2) are sometimes referred to as "monomer (a1-0)", "monomer (a1-1)" and "monomer (a1-2)"), respectively:

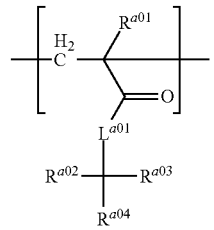

(a1-0)

wherein $L^{a01}$ represents —O— or *—O—$(CH_2)_{k01}$—CO—O—, k01 represents an integer of 1 to 7,

* represents a binding site to —CO—, $R^{a01}$ represents a hydrogen atom or a methyl group, and $R^{a02}$, $R^{a03}$ and $R^{a04}$ each independently represent a $C_1$ to $C_8$ alkyl group, a $C_3$ to $C_{18}$ alicyclic hydrocarbon group or a combination thereof.

$L^{a01}$ is preferably an —O— or *—O—$(CH_2)_{k01}$—CO—O— in which k01 is preferably an integer of 1 to 4, more preferably an integer of 1, more preferably an —O—.

Examples of the alkyl group and an alicyclic hydrocarbon group, and the combination thereof for $R^{a02}$, $R^{a03}$ and $R^{a04}$ are the same examples as the group described in $R^{a1}$ to $R^{a3}$ in the formula (1).

The alkyl group of $R^{a02}$, $R^{a03}$ and $R^{a04}$ is preferably a $C_1$ to $C_6$ alkyl group.

The alicyclic hydrocarbon group of $R^{a02}$, $R^{a03}$ and $R^{a04}$ is preferably a $C_3$ to $C_8$ alicyclic hydrocarbon group, more preferably a $C_3$ to $C_6$ alicyclic hydrocarbon group.

The group formed by combining the alkyl group and the alicyclic hydrocarbon group has preferably 18 or less of carbon atom. Examples of those groups include methylcyclohexyl, dimethylcyclohexyl, methylnorbornyl, methyladamantyl, cyclohexylmethl, methylcyclohexyl methyladamantylmethyl, adamantylmethyl and norbornylmethyl groups.

$R^{a02}$ and $R^{a03}$ is preferably a $C_1$ to $C_6$ alkyl group, more preferably a methyl group or an ethyl group.

$R^{a04}$ is preferably a $C_1$ to $C_6$ alkyl group or a $C_5$ to $C_{12}$ alicyclic hydrocarbon group, more preferably methyl, ethyl, cyclohexyl or adamantyl group.

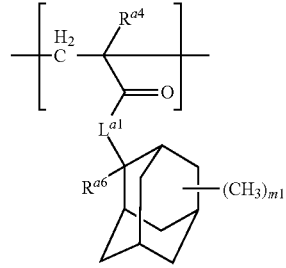

(a1-1)

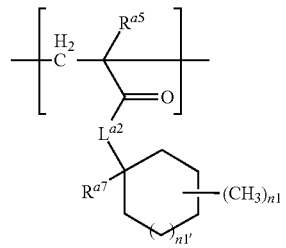

(a1-2)

In each formula, $L^{a1}$ and $L^{a2}$ each independently represent —O— or *—O—$(CH_2)_{k1}$—CO—O—, k1 represents an integer of 1 to 7,

* represents a binding site to —CO—, $R^{a4}$ and $R^{a5}$ each independently represent a hydrogen atom or a methyl group, $R^{a6}$ and $R^{a7}$ each independently represent a $C_1$ to $C_8$ alkyl group, a $C_3$ to $C_{18}$ alicyclic hydrocarbon group or a combination thereof, m1 represents an integer of 0 to 14, n1 represents an integer of 0 to 10, and n1' represents an integer of 0 to 3.

$L^{a1}$ and $L^{a2}$ are preferably —O— or *—O—$(CH_2)_{k1'}$—CO—O— in which k1' represents an integer of 1 to 4 and more preferably 1, and still more preferably —O—.

$R^{a4}$ and $R^{a5}$ are preferably a methyl group.

Examples of the alkyl group and an alicyclic hydrocarbon group, and the combination thereof for $R^{a6}$ and $R^{a7}$ are the same examples as the group described in $R^{a1}$ to $R^{a3}$ in the formula (1).

The alkyl group of $R^{a6}$ and $R^{a7}$ is preferably a $C_1$ to $C_6$ alkyl group. The alicyclic hydrocarbon group of $R^{a6}$ and $R^{a7}$ is preferably a $C_3$ to $C_8$ alicyclic hydrocarbon group, and more preferably a $C_3$ to $C_6$ alicyclic hydrocarbon group.

m1 is preferably an integer of 0 to 3, and more preferably 0 or 1.

n1 is preferably an integer of 0 to 3, and more preferably 0 or 1.

n1' is preferably 0 or 1.

Examples of the structural unit (a1-0) preferably include structural units represented by formula (a1-0-1) to formula (a1-0-12), and more preferably structural units represented by formula (a1-0-1) to formula (a1-0-10) below.

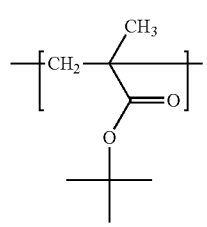

(a1-0-1)

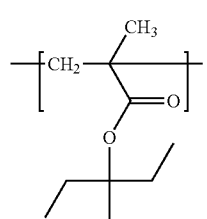

(a1-0-2)

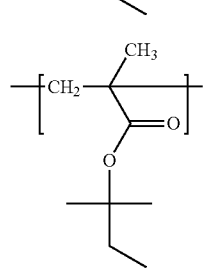

(a1-0-3)

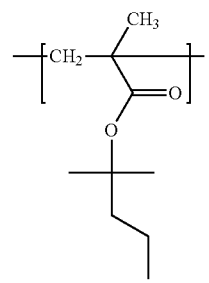

(a1-0-4)

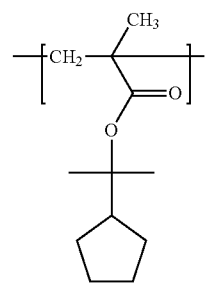

(a1-0-5)

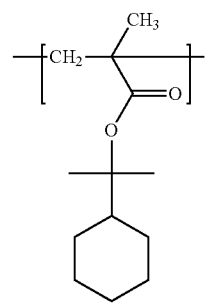

(a1-0-6)

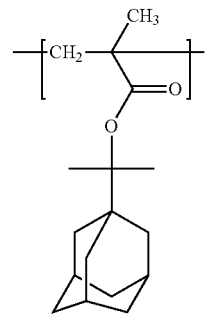

(a1-0-7)

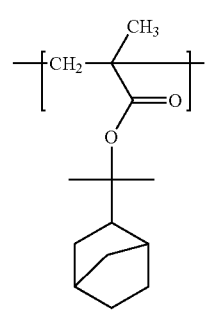

(a1-0-8)

-continued (a1-0-9)
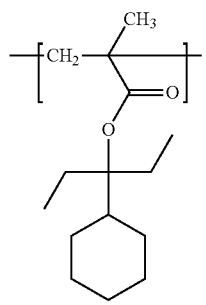

(a1-0-10)
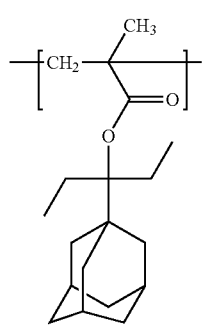

(a1-0-11)
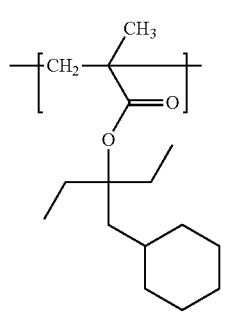

(a1-0-12)
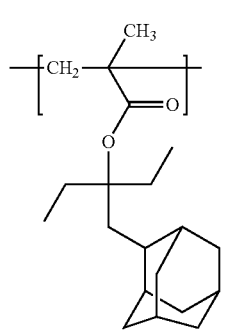

(a1-1-1)
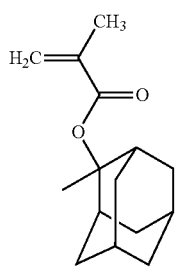

(a1-1-2)
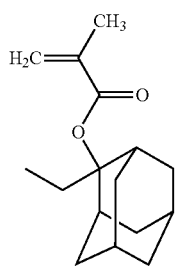

(a1-1-3)
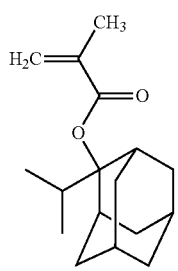

(a1-1-4)
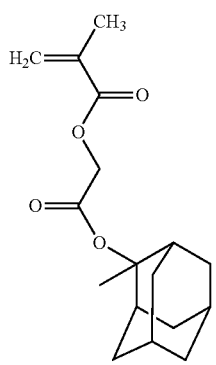

(a1-1-5)
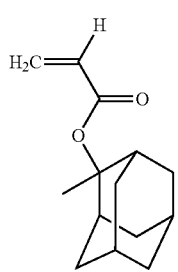

Examples of the structural units (a1-0) include structural units in which a methyl group corresponding to $R^{a01}$ has been replaced by a hydrogen atom.

Examples of the monomer (a1-1) include monomers described in JP 2010-204646A. Among these, the monomers are preferably monomers represented by formula (a1-1-1) to formula (a1-1-8), and more preferably monomers represented by formula (a1-1-1) to formula (a1-1-4) below.

(a1-1-6)
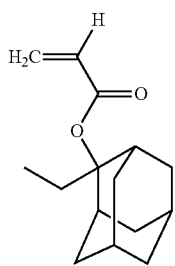

(a1-1-7)
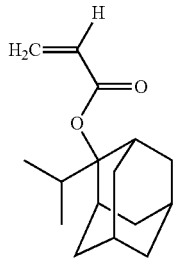

(a1-1-8)
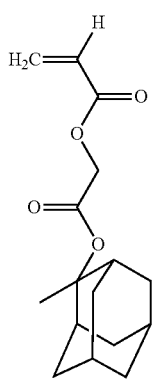

Examples of the monomer (a1-2) include 1-methylcyclopentane-1-yl (meth)acrylate, 1-ethylcyclopentane-1-yl (meth)acrylate, 1-methylcyclohexane-1-yl (meth)acrylate, 1-ethylcyclohexane-1-yl (meth)acrylate, 1-ethylcycloheptane-1-yl (meth)acrylate, 1-ethylcyclooctane-1-yl (meth)acrylate, 1-isopropylcyclopentane-1-yl (meth)acrylate and 1-isopropylcyclohexane-1-yl (meth)acrylate. Among these, the monomers are preferably monomers represented by formula (a1-2-1) to formula (a1-2-12), and more preferably monomers represented by formula (a1-2-3), formula (a1-2-4), formula (a1-2-9) and formula (a1-2-10), and still more preferably monomer represented by formula (a1-2-3) and formula (a1-2-9) below.

(a1-2-1)
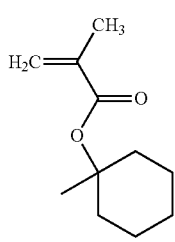

(a1-2-2)
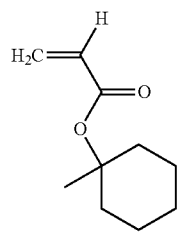

(a1-2-3)
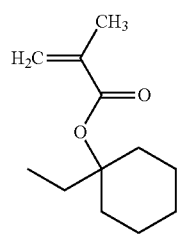

(a1-2-4)
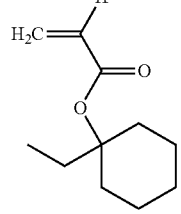

(a1-2-5)
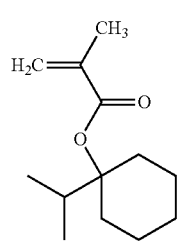

(a1-2-6)
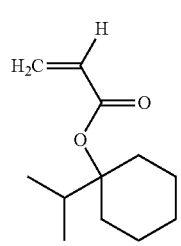

(a1-2-7)
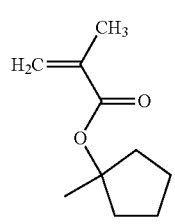

(a1-2-8)
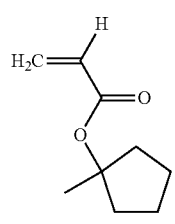

-continued

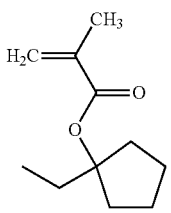
(a1-2-9)

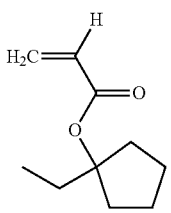
(a1-2-10)

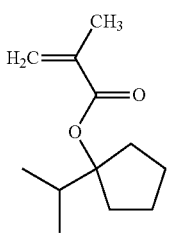
(a1-2-11)

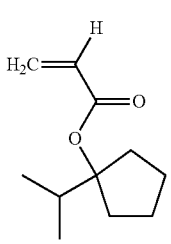
(a1-2-12)

When the resin (A1) has the structural unit (a1-0) and/or the structural unit (a1-1) and/or the structural unit (a1-2), the total proportion thereof is generally 10 to 95% by mole, preferably 15 to 90% by mole, and more preferably 20 to 85% by mole, with respect to the total structural units (100% by mole) of the resin (A1).

Further, examples of the structural unit (a1) having the group (1) include a structural unit presented by formula (a1-3). The structural unit represented by formula (a1-3) is sometimes referred to as "structural unit (a1-3)". The monomer from which the structural unit (a1-3) is derived is sometimes referred to as "monomer (a1-3)".

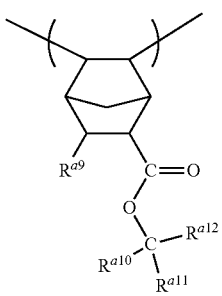
(a1-3)

In the formula, $R^{a9}$ represents a carboxy group, a cyano group, a $-COOR^{a13}$, a hydrogen atom or a $C_1$ to $C_3$ aliphatic hydrocarbon group that may have a hydroxy group, $R^{a13}$ represents a $C_1$ to $C_8$ aliphatic hydrocarbon group, a $C_3$ to $C_{20}$ alicyclic hydrocarbon group or a group formed by combining thereof, a hydrogen atom contained in the aliphatic hydrocarbon group and the alicyclic hydrocarbon group may be replaced by a hydroxy group, a methylene group contained in the aliphatic hydrocarbon group and the alicyclic hydrocarbon group may be replaced by an oxygen atom or a carbonyl group, and $R^{a10}$, $R^{a11}$ and $R^{a12}$ each independently represent a $C_1$ to $C_8$ alkyl group, a $C_3$ to $C_{20}$ alicyclic hydrocarbon group or a group formed by combining thereof, or $R^{a10}$ and $R^{a11}$ may be bonded together with a carbon atom bonded thereto to form a $C_2$ to $C_{20}$ divalent hydrocarbon group.

Here, examples of $-COOR^{a13}$ group include a group in which a carbonyl group is bonded to the alkoxy group, such as methoxycarbonyl and ethoxycarbonyl groups.

Examples of the aliphatic hydrocarbon group that may have a hydroxy group for $R^{a9}$ include methyl, ethyl, propyl, hydroxymethy and 2-hydroxyethyl groups.

Examples of the $C_1$ to $C_8$ aliphatic hydrocarbon group for $R^{a13}$ include methyl, ethyl, propyl, isopropyl, n-butyl, sec-butyl, tert-butyl, n-pentyl, n-hexyl, n-heptyl, 2-ethylhexyl and n-octyl groups.

Examples of the $C_3$ to $C_{20}$ alicyclic hydrocarbon group for $R^{a13}$ include cyclopentyl, cyclopropyl, adamantyl, adamantylmetyl, 1-(adamantyl-1-yl)-methylethyl, 2-oxo-oxolane-3-yl, 2-oxo-oxolane-4-yl groups.

Examples of the alkyl group for $R^{a10}$ to $R^{a12}$ include methyl, ethyl, n-propyl, isopropyl, n-butyl, sec-butyl, tert-butyl, n-pentyl, n-hexyl, n-heptyl, 2-ethylhexyl and n-octyl groups.

Examples of the alicyclic hydrocarbon group for $R^{a10}$ and $R^{a12}$ include monocyclic groups such as a cycloalkyl group, i.e., cyclopropyl, cyclobutyl, cyclopentyl, cyclohexyl, methylcyclohexyl, dimethylcyclohexyl, cycloheptyl, cyclooctyl and cyclodecyl groups; and polycyclic groups such as decahydronaphtyl, adamantyl, 2-alkyl-2-adamantyl, 1-(adamantane-1-yl)alkane-1-yl, norbornyl, methyl norbornyl and isobornyl groups.

When $R^{a10}$ and $R^{a11}$ are bonded together with a carbon atom bonded thereto to form a divalent hydrocarbon group, examples of the group $-C(R^{a10})(R^{a11})(R^{a12})$ include the following groups.

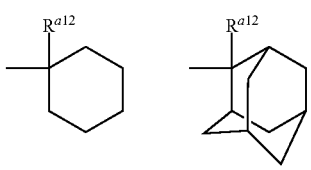

In each formula, $R^{a12}$ is as defined above.

Examples of the monomer (a1-3) include tert-butyl 5-norbornene-2-carboxylate, 1-cyclohexyl-1-methylethyl 5-norbornene-2-carboxylate, 1-methylcyclohexyl 5-norbornene-2-carboxylate, 2-methy-2-adamantane-2-yl 5-norbornene-2-carboxylate, 2-ethyl-2-adamantane-2-yl 5-norbornene-2-carboxylate, 1-(4-methycyclohexyl)-1-methylethyl 5-norbornene-2-carboxylate, 1-(4-hydroxycyclohexyl)-1-methylethyl 5-norbornene-2-carboxylate, 1-methyl-(4-oxocyclohexyl)-1-ethyl 5-norbornene-2-carboxylate, and 1-(1-adamantane-1-yl)-1-methylethyl 5-norbornene-2-carboxylate.

The resin (A1) including the structural unit (a1-3) can improve the resolution of the obtained resist composition because it has a bulky structure, and also can improve a dry-etching tolerance of the obtained resist composition because of incorporated a rigid norbornene ring into a main chain of the resin (A1).

When the resin (A1) has the structural unit (a1-3), the proportion thereof is preferably 10% by mole to 95% by mole, more preferably 15% by mole to 90% by mole, and still more preferably 20% by mole to 85% by mole, with respect to the total structural units constituting the resin (A1) (100% by mole).

Examples of a structural unit (a1) having the group (2) include a structural unit represented by formula (a1-4). The structural unit is sometimes referred to as "structural unit (a1-4)".

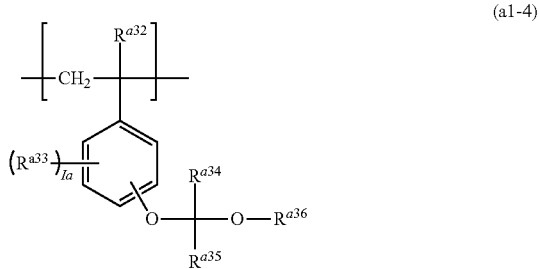

(a1-4)

In the formula, $R^{a32}$ represents a hydrogen atom, a halogen atom or a $C_1$ to $C_6$ alkyl group that may have a halogen atom, $R^{a33}$ in each occurrence independently represent a halogen atom, a hydroxy group, a $C_1$ to $C_6$ alkyl group, a $C_1$ to $C_6$ alkoxy group, a $C_2$ to $C_4$ acyl group, a $C_2$ to $C_4$ acyloxy group, an acryloyloxy group or methacryloyloxy group, la represents an integer 0 to 4, $R^{a34}$ and $R^{a35}$ each independently represent a hydrogen atom or a $C_1$ to $C_{12}$ hydrocarbon group; and $R^{a36}$ represents a $C_1$ to $C_{20}$ hydrocarbon group, or $R^{a35}$ and $R^{a36}$ may be bonded together with a C—O bonded thereto to form a divalent $C_3$ to $C_{20}$ heterocyclic group, and a methylene group contained in the hydrocarbon group or the divalent heterocyclic group may be replaced by an oxygen atom or a sulfur atom.

Examples of the alkyl group of $R^{a32}$ and $R^{a33}$ include methyl, ethyl, propyl, isopropyl, butyl, pentyl and hexyl groups. The alkyl group is preferably a $C_1$ to $C_4$ alkyl group, and more preferably a methyl group or an ethyl group, and still more preferably a methyl group.

Examples of the halogen atom of $R^{a32}$ and $R^{a33}$ include a fluorine, chlorine, bromine and iodine atoms.

Examples of the alkyl group that may have a halogen atom include trifluoromethyl, difluoromethyl, methyl, perfluoroethyl, 1,1,1-trifluoroethyl, 1,1,2,2-tetrafluoroethyl, ethyl, perfluoropropyl, 1,1,1,2,2-pentafluoropropyl, propyl, perfluorobutyl, 1,1,2,2,3,3,4,4-octafluorobutyl, butyl, perfluoropentyl, 1,1,1,2,2,3,3,4,4-nonafluoropentyl, n-pentyl, n-hexyl and n-perfluorohexyl groups.

Examples of an alkoxy group include methoxy, ethoxy, propoxy, butoxy, pentyloxy and hexyloxy groups. The alkoxy group is preferably a $C_1$ to $C_4$ alkoxy group, more preferably a methoxy group or an ethoxy group, and still more preferably methoxy group.

Examples of the acyl group include acetyl, propionyl and butyryl groups.

Examples of the acyloxy group include acetyloxy, propionyloxy and butyryloxy groups.

Examples of the hydrocarbon group for $R^{a34}$ and $R^{a35}$ are the same examples as described in $R^{a1'}$ to $R^{a2'}$ in the formula (2).

Examples of hydrocarbon group for $R^{a36}$ include a $C_1$ to $C_{18}$ alkyl group, a $C_3$ to $C_{18}$ alicyclic hydrocarbon group, a $C_6$ to $C_{18}$ aromatic hydrocarbon group or a group formed by combining thereof.

In the formula (a1-4), $R^{a32}$ is preferably a hydrogen atom.

$R^{a33}$ is preferably a $C_1$ to $C_4$ alkoxy group, more preferably a methoxy group or an ethoxy group, and still more preferably a methoxy group.

la is preferably 0 or 1, and more preferably 0.

$R^{a34}$ is preferably a hydrogen atom.

$R^{a35}$ is preferably a $C_1$ to $C_{12}$ hydrocarbon group, and more preferably a methyl group or an ethyl group.

The hydrocarbon group for $R^{a36}$ is preferably a $C_1$ to $C_{18}$ alkyl group, a $C_3$ to $C_{18}$ alicyclic hydrocarbon group, a $C_6$ to $C_{18}$ aromatic hydrocarbon group or a combination thereof, and more preferably a $C_1$ to $C_{18}$ alkyl group, a $C_3$ to $C_{18}$ alicyclic hydrocarbon group or a $C_7$ to $C_{18}$ aralkyl group. The alkyl group and the alicyclic hydrocarbon group for $R^{a36}$ are preferably unsubstituted. When the aromatic hydrocarbon group of $R^{a36}$ has a substituent, the substituent is preferably a $C_6$ to $C_{10}$ aryloxy group.

Examples of the monomer from which the structural unit (a1-4) is derived include monomers described in JP 2010-204646A. Among these, the monomers are preferably the following monomers represented by formula (a1-4-1) to formula (a1-4-7), and more preferably monomers represented by formula (a1-4-1) to formula (a1-4-5).

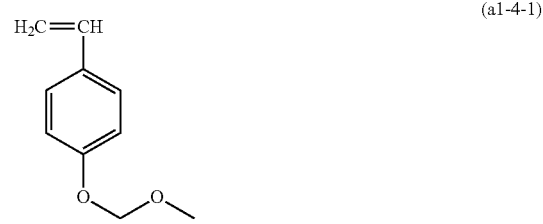

(a1-4-1)

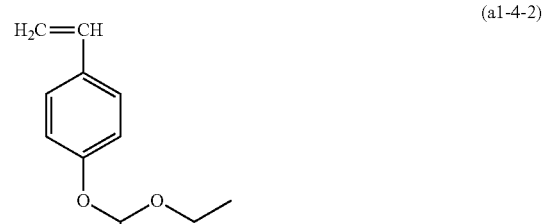

(a1-4-2)

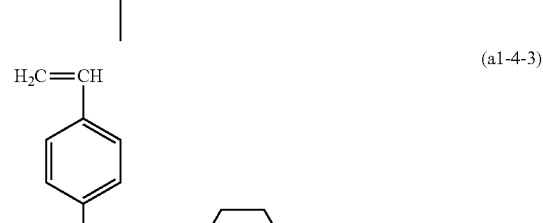

(a1-4-3)

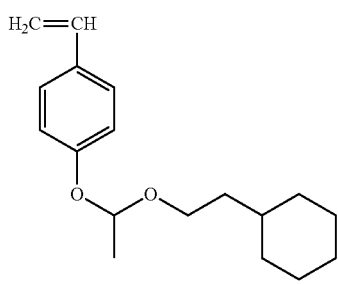
(a1-4-4)

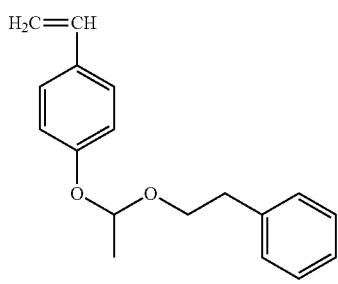
(a1-4-5)

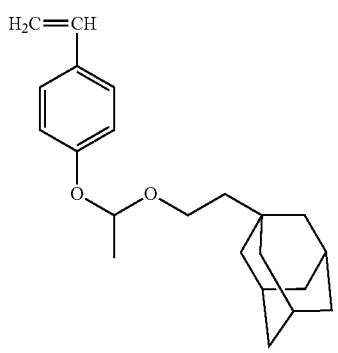
(a1-4-6)

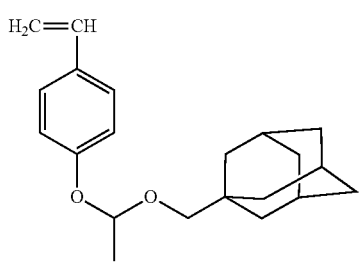
(a1-4-7)

When the resin (A1) has the structural unit (a1-4), the proportion thereof is preferably 10% by mole to 95% by mole, more preferably 15% by mole to 90% by mole, and still more preferably 20% by mole to 85% by mole, with respect to the total structural units constituting the resin (A1) (100% by mole).

Examples of the structural unit having an acid-labile group include a structural unit represented by formula (a1-5). The structural unit is sometimes referred to as "structural unit (a1-5)".

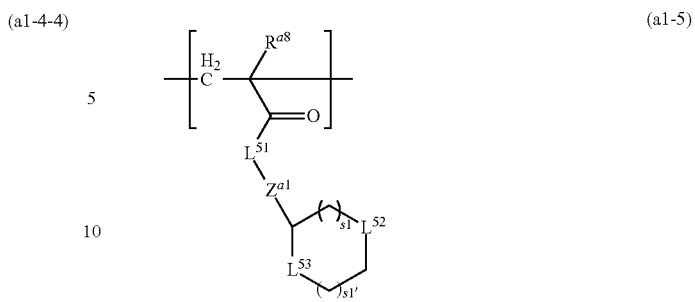
(a1-5)

In the formula (a1-5), $R^{a8}$ represents a hydrogen atom, a halogen atom or a $C_1$ to $C_6$ alkyl group that may have a halogen atom, $Z^{a1}$ represent a single bond or *—$(CH_2)_{h3}$—CO-$L^{54}$-, h3 represents an integer of 1 to 4,

* represents a binding site to $L^{51}$, $L^{51}$, $L^{52}$, $L^{53}$ and $L^{54}$ each independently represent —O— or —S—, s1 represents an integer of 1 to 3, and s1' represents an integer of 0 to 3.

In the formula (a1-5), $R^{a8}$ is preferably a hydrogen atom, a methyl group or a trifluoromethyl group;

$L^{51}$ is preferably —O—;

$L^{52}$ and $L^{53}$ are independently preferably —O— or —S—, and more preferably one is —O— and another is —S—.

s1 is preferably 1;

s1' is preferably an integer of 0 to 2;

$Z^{a1}$ is preferably a single bond or *—$CH_2$—CO—O—. * represents a binding site to $L^{51}$.

Examples of a monomer from which the structural unit (a1-5) is derived include a monomer described in JP 2010-61117A. Among these, the monomers are preferably monomers represented by formula (a1-5-1) to formula (a1-5-4), and more preferably monomers represented by formula (a1-5-1) to formula (a1-5-2) below.

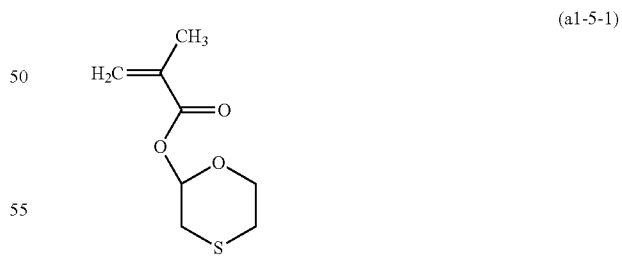
(a1-5-1)

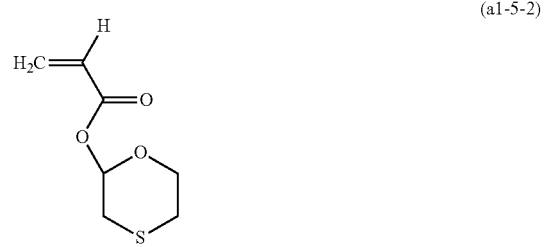
(a1-5-2)

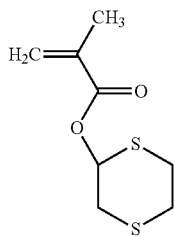

(a1-5-3)

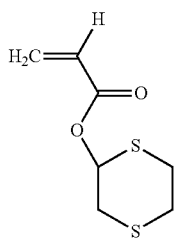

(a1-5-4)

When the resin (A1) has the structural unit (a1-5), the proportion thereof is preferably 1% by mole to 50% by mole, more preferably 3% by mole to 45% by mole, and still more preferably 5% by mole to 40% by mole, with respect to the total structural units (100% by mole) constituting the resin (A1).

The resin (A1) has, as the structural unit (a1), preferably at least one, more preferably two or more structural units selected from the structural unit (a1-0), the structural unit (a1-1), the structural unit (a1-2) and the structural unit (a1-5), still more preferably the structural unit (a1-1) or the structural unit (a1-2), a combination of the structural unit (a1-1) and the structural unit (a1-2), a combination of the structural unit (a1-1) and the structural unit (a1-5), a combination of the structural unit (a1-1) and the structural unit (a1-0), a combination of the structural unit (a1-2) and the structural unit (a1-0), a combination of the structural unit (a1-5) and the structural unit (a1-0), a combination of the structural unit (a1-0), the structural unit (a1-1) and the structural unit (a1-2), a combination of the structural unit (a1-0), the structural unit (a1-1) and the structural unit (a1-5), and further still preferably a combination of the structural unit (a1-1) and the structural unit (a1-2), a combination of the structural unit (a1-1) and the structural unit (a1-5).

<Structural Unit (s)>

The structural unit (s) is derived from a monomer having no acid-labile group (which monomer is sometimes referred to as "monomer (s)").

As the monomer (s) from which the structural unit (s) is derived, a known monomer having no acid-labile group can be used.

As the structural unit (s), a structural unit having a hydroxy group or a lactone ring but having no acid-labile group is preferred. When a resin including the structural unit derived from a structural unit having a hydroxy group but having no acid-labile group (such structural unit is sometimes referred to as "structural unit (a2)") and/or a structural unit having a lactone ring but having no acid-labile group (such structural unit is sometimes referred to as "structural unit (a3)") is used, the adhesiveness of resist to a substrate and resolution of resist pattern tend to be improved.

<Structural Unit (a2)>

The structural unit (a2) having a hydroxy group may be an alcoholic hydroxy group or a phenolic hydroxy group.

When KrF excimer laser lithography (248 nm), or high-energy irradiation such as electron beam or EUV (extreme ultraviolet) is used for the resist composition, using the structural unit having a phenolic hydroxy group as the structural unit (a2) is preferred.

When ArF excimer laser lithography (193 nm) is used, using the structural unit having an alcoholic hydroxy group as the structural unit (a2) is preferred, and using the structural unit represented by formula (a2-1) is more preferred.

The structural unit (a2) may be used as a single structural unit or as a combination of two or more structural units.

When the resin (A1) includes the structural unit (a2), the total proportion thereof is preferably 5% by mole to 95% by mole, more preferably 10% by mole to 80% by mole, and still more preferably 15% by mole to 80% by mole, with respect to the total structural units (100% by mole) constituting the resin (A1).

Examples of the structural unit (a2) having a phenolic hydroxy group include a structural unit represented by formula (a2-0) (which is sometimes referred to as "structural unit (a2-0)").

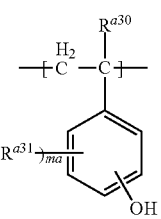

(a2-0)

wherein $R^{a30}$ represents a hydrogen atom, a halogen atom or a $C_1$ to $C_6$ alkyl group that may have a halogen atom, $R^{a31}$ in each occurrence independently represents a halogen atom, a hydroxy group, a $C_1$ to $C_6$ alkyl group, a $C_1$ to $C_6$ alkoxy group, a $C_2$ to $C_4$ acyl group, a $C_2$ to $C_4$ acyloxy group, an acryloyloxy group or methacryloyloxy group, and ma represents an integer 0 to 4.

Examples of the alkyl group include methyl, ethyl, propyl, butyl, n-pentyl and n-hexyl groups.

Examples of the halogen atom include a chlorine atom, a fluorine atom and bromine atom.

Examples of the $C_1$ to $C_6$ alkyl group that may have a halogen atom for $R^{a30}$ include trifluoromethyl, difluoromethyl, methyl, perfluoromethyl, 1,1,1-trifluoroethyl, 1,1,2,2-tetrafluoroethyl, ethyl, perfluoropropyl, 1,1,1,2,2-pentafluoropropyl, propyl, perfluorobutyl, 1,1,2,2,3,3,4,4-octafluorobutyl, butyl, perfluoropentyl, 1,1,1,2,2,3,3,4,4-nonafluoropentyl, n-pentyl, n-hexyl and n-perfluorohexyl groups.

$R^{a30}$ is preferably a hydrogen atom or a $C_1$ to $C_4$ alkyl group, and more preferably a hydrogen atom, a methyl group or an ethyl group, and still more preferably a hydrogen atom or a methyl group.

Examples of the alkoxy group for $R^{a31}$ include methoxy, ethoxy, propoxy, butoxy, pentyloxy, and hexyloxy groups. $R^{a31}$ is preferably a $C_1$ to $C_4$ alkoxy group, more preferably a methoxy group or an ethoxy group, and still more preferably a methoxy group.

Examples of the acyl group include acetyl, propionyl and butyryl groups.

Examples of the acyloxy group include acetyloxy, propionyloxy and butyryloxy groups.

ma is preferably 0, 1 or 2, more preferably 0 or 1, still more preferably 0.

The structural unit (a2-0) having a phenolic hydroxy group is preferably a structural unit represented below.

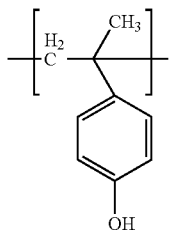
(a2-0-1)

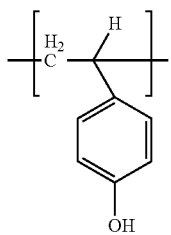
(a2-0-2)

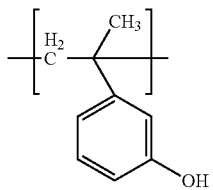
(a2-0-3)

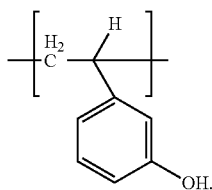
(a2-0-4)

Among these, a structural unit represented by formula (a2-0-1) and formula (a2-0-2) are preferred.

Examples of a monomer from which the structural unit (a2-0) is derived include monomers described in JP2010-204634A.

The resin (A1) which has the structural units (a2-0) having a phenolic hydroxy group can be produced, for example, by polymerizing a monomer where its phenolic hydroxy group has been protected with a suitable protecting group, followed by deprotection. The deprotection is carried in such a manner that an acid-labile group in the structural unit (a1) is significantly impaired. Examples of the protecting group for a phenolic hydroxy group include an acetyl group.

When the resin (A1) further has the structural unit (a2-0) having the phenolic hydroxy group, the proportion thereof is preferably 5% by mole to 95% by mole, more preferably 10% by mole to 80% by mole, and still more preferably 15% by mole to 80% by mole, with respect to the total structural units (100% by mole) constituting the resin (A1).

Examples of the structural unit (a2) having an alcoholic hydroxy group include the structural unit represented by formula (a2-1) (which is sometimes referred to as "structural unit (a2-1)").

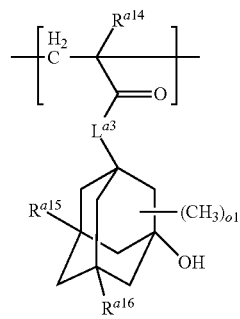
(a2-1)

In the formula (a2-1), $L^{a3}$ represents —O— or *—O—$(CH_2)_{k2}$—CO—O—, k2 represents an integer of 1 to 7,

* represents a binding site to —CO—, $R^{a14}$ represents a hydrogen atom or a methyl group, $R^{a15}$ and $R^{a16}$ each independently represent a hydrogen atom, a methyl group or a hydroxy group, and o1 represents an integer of 0 to 10.

In the formula (a2-1), $L^{a3}$ is preferably —O—, —O—$(CH_2)_{f1}$—CO—O—, here f1 represents an integer of 1 to 4, and more preferably —O—.

$R^{a14}$ is preferably a methyl group.

$R^{a15}$ is preferably a hydrogen atom.

$R^{a16}$ is preferably a hydrogen atom or a hydroxy group.

o1 is preferably an integer of 0 to 3, and more preferably an integer of 0 or 1.

Examples of the monomer from which the structural unit (a2-1) is derived include monomers described in JP 2010-204646A. Among these, the structural units (a2-1) are preferably structural units represented by formula (a2-1-1) to formula (a2-1-6), more preferably structural units represented by formula (a2-1-1) to formula (a2-1-4), and still more preferably structural units represented by formula (a2-1-1) and formula (a2-1-3).

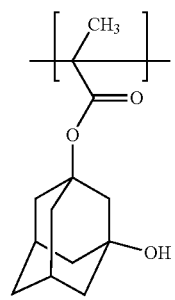
(a2-1-1)

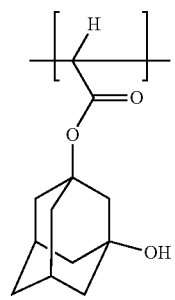
(a2-1-2)

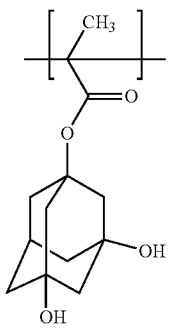 (a2-1-3)

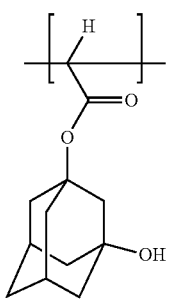 (a2-1-4)

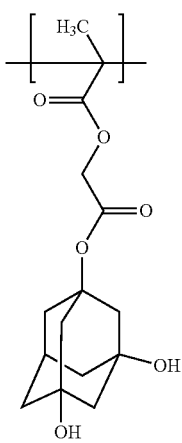 (a2-1-5)

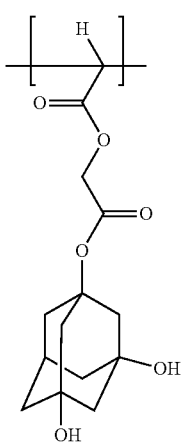 (a2-1-6)

When the resin (A1) has the structural unit (a2-1) having an alcoholic hydroxy group, the proportion thereof is generally 1% by mole to 45% by mole, preferably 1% by mole to 40% by mole, more preferably 1% by mole to 35% by mole, and still more preferably 2% by mole to 20% by mole, with respect to the total structural units (100% by mole) constituting the resin (A1).

<Structural Unit (a3)>

The lactone ring included in the structural unit (a3) may be a monocyclic ring such as β-propiolactone, γ-butyrolactone, δ-valerolactone, or a condensed ring of monocyclic lactone ring with another ring. Examples of the lactone ring preferably include γ-butyrolactone, adamantane lactone, or bridged ring with γ-butyrolactone.

Examples of the structural unit (a3) include structural units represented by any of formula (a3-1), formula (a3-2), formula (a3-3) and formula (a3-4). These structural units may be used as a single unit or as a combination of two or more units.

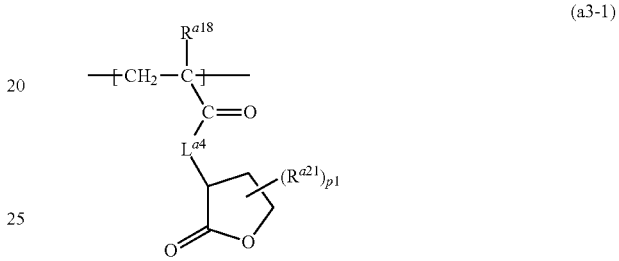 (a3-1)

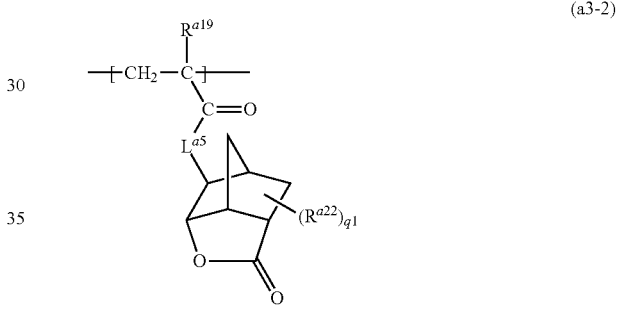 (a3-2)

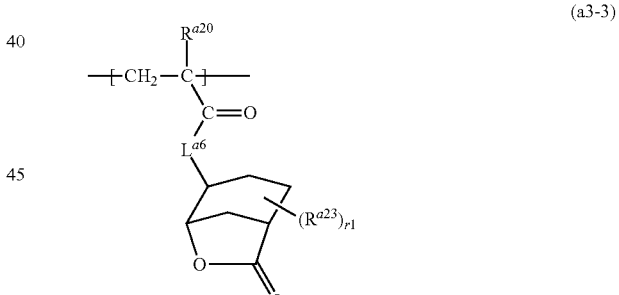 (a3-3)

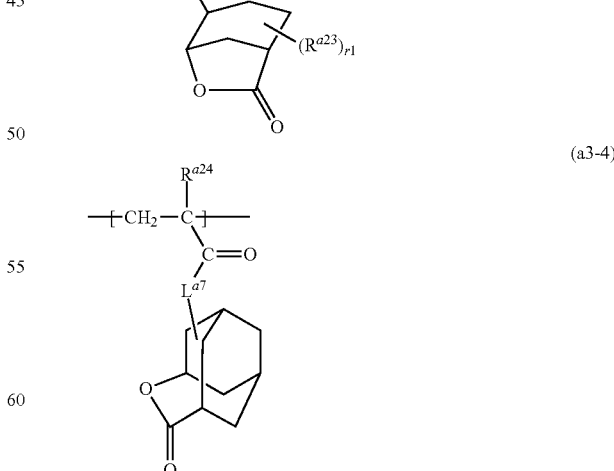 (a3-4)

In each formula, $L^{a4}$ represents *—O— or *—O—$(CH_2)_{k3}$—CO—O—, k3 represents an integer of 1 to 7, * represents a binding site to a carbonyl group, $R^{a18}$ represents a hydrogen atom or a methyl group, $R^{a21}$ in each occurrence represents a $C_1$ to $C_4$ aliphatic hydrocarbon group, and p1 represents an integer of 0 to 5, $L^{a5}$ represents *—O— or *—O—$(CH_2)_{k3}$—CO—O—, k3 represents an integer of 1 to 7, * represents a binding site to a carbonyl group, $R^{a19}$ represents a hydrogen atom or a methyl group, $R^{a22}$ in each occurrence represents a carboxy group, a cyano group or a $C_1$ to $C_4$ aliphatic hydrocarbon group, q1 represents an integer of 0 to 3, $L^{a6}$ represents *—O— or *—O—$(CH_2)_{k3}$—CO—O—, k3 represents an integer of 1 to 7, * represents a binding site to a carbonyl group, $R^{a20}$ represents a hydrogen atom or a methyl group, $R^{a23}$ in each occurrence represents a carboxy group, a cyano group or a $C_1$ to $C_4$ aliphatic hydrocarbon group, and r1 represents an integer of 0 to 3, $R^{a24}$ represents a hydrogen atom, a halogen atom or a $C_1$ to $C_6$ alkyl group that may have a halogen atom, $L^{a7}$ represents a single bond, *-$L^{a8}$-O—, *-$L^{a8}$-CO—O—, *-$L^{a8}$-CO—O-$L^{a9}$-CO—O—, or *-$L^{a8}$-O—CO-$L^{a9}$-O—; * represents a binding site to a carbonyl group, and $L^{a8}$ and $L^{a9}$ each independently represent a $C_1$ to $C_6$ alkanediyl group.

Examples of the aliphatic hydrocarbon group for $R^{a21}$, $R^{a2}$ and $R^{a23}$ include an alkyl group such as methyl, ethyl, n-propyl, isopropyl, n-butyl, sec-butyl and tert-butyl groups.

Examples of the halogen atom for $R^{a24}$ include fluorine, chlorine, bromine and iodine atoms;

Examples of the alkyl group for $R^{a24}$ include methyl, ethyl, n-propyl, isopropyl, n-butyl, sec-butyl, tert-butyl, n-pentyl and n-hexyl groups. The alkyl group is preferably a $C_1$ to $C_4$ alkyl group, more preferably a methyl group or an ethyl group.

Examples of the alkyl group having a halogen atom of $R^{a24}$ include trifluoromethyl, perfluoroethyl, perfluoropropyl, perfluoro-isopropyl, perfluorobutyl, perfluoro-sec-butyl, perfluoro-tert-butyl, perfluoropentyl, perfluorohexyl, trichloromethyl, tribromomethyl and triiodomethyl groups.

Examples of the alkanediyl group of $L^{a8}$ and $L^{a9}$ include methylene, ethylene, propane-1,3-diyl, propane-1,2-diyl, butane-1,4-diyl, pentane-1,5-diyl, hexane-1,6-diyl, butane-1,3-diyl, 2-methylpropane-1,3-diyl, 2-methylpropane-1,2-diyl, pentane-1,4-diyl and 2-methylbutane-1,4-diyl groups.

In the formulae (a3-1) to (a3-3), $L^{a4}$ to $L^{a6}$ is independently preferably —O—, *—O—$(CH_2)_{k3'}$—CO—O—, here k3' represents an integer of 1 to 4, more preferably —O— or *—O—$CH_2$—CO—O—, and still more preferably *—O—.

$R^{a18}$ to $R^{a21}$ is preferably a methyl group.

$R^{a22}$ and $R^{a23}$ are each independently preferably a carboxy group, a cyano group or a methyl group.

p1, q1 and r1 are independently preferably an integer of 0 to 2, and more preferably 0 or 1.

In the formula (a3-4), $R^{a24}$ is preferably a hydrogen atom or a $C_1$ to $C_4$ alkyl group, more preferably a hydrogen atom, a methyl group or an ethyl group, and still more preferably a hydrogen atom or a methyl group.

$L^{a7}$ is preferably a single bond or *-$L^{a8}$-CO—O—, and more preferably a single bond, —$CH_2$—CO—O— or —$C_2H_4$—CO—O—.

Examples of the monomer from which the structural unit (a3) is derived include monomers described in JP 2010-204646A, monomers described in JP2000-122294A and monomers described in JP2012-41274A. The structural units (a3) are preferably structural units represented by formula (a3-1-1) to formula (a3-1-4), formula (a3-2-1) to formula (a3-2-4), formula (a3-3-1) to formula (a3-3-4), formula (a3-4-1) to formula (a3-4-12), more preferably structural units represented by formula (a3-1-1), formula (a3-1-2), formula (a3-2-3), formula (a3-2-4), formula (a3-4-1) to formula (a3-4-12), still more preferably structural units represented by formula (a3-4-1) to formula (a 3-4-12), further still preferably formula (a3-4-1) to formula (a3-4-6) below.

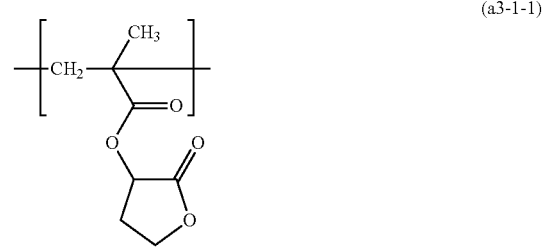
(a3-1-1)

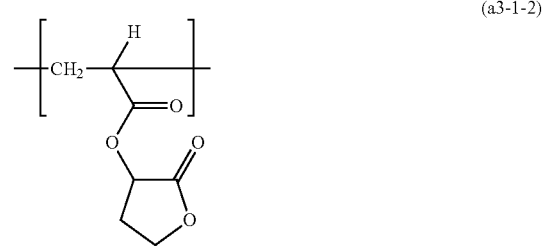
(a3-1-2)

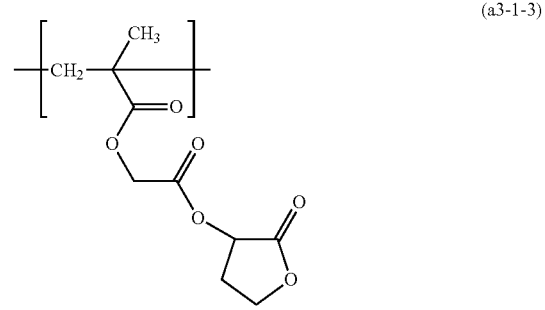
(a3-1-3)

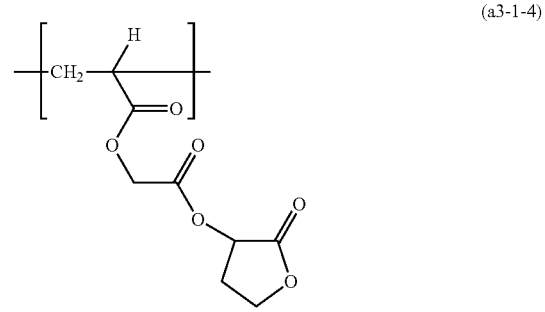
(a3-1-4)

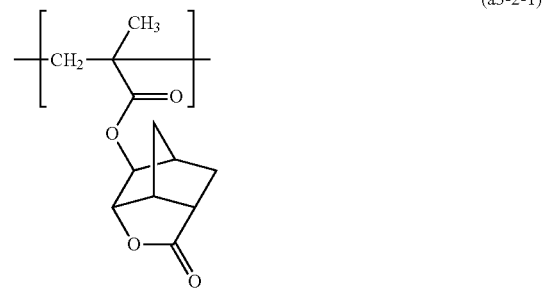
(a3-2-1)

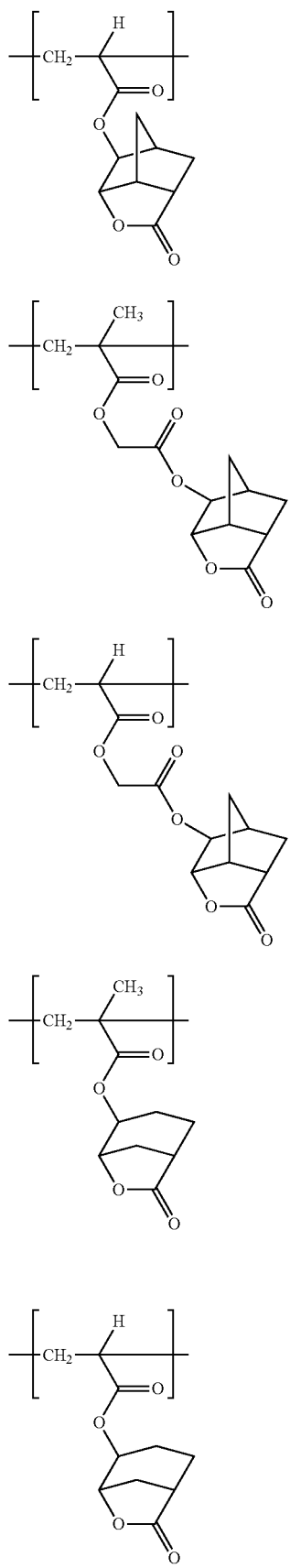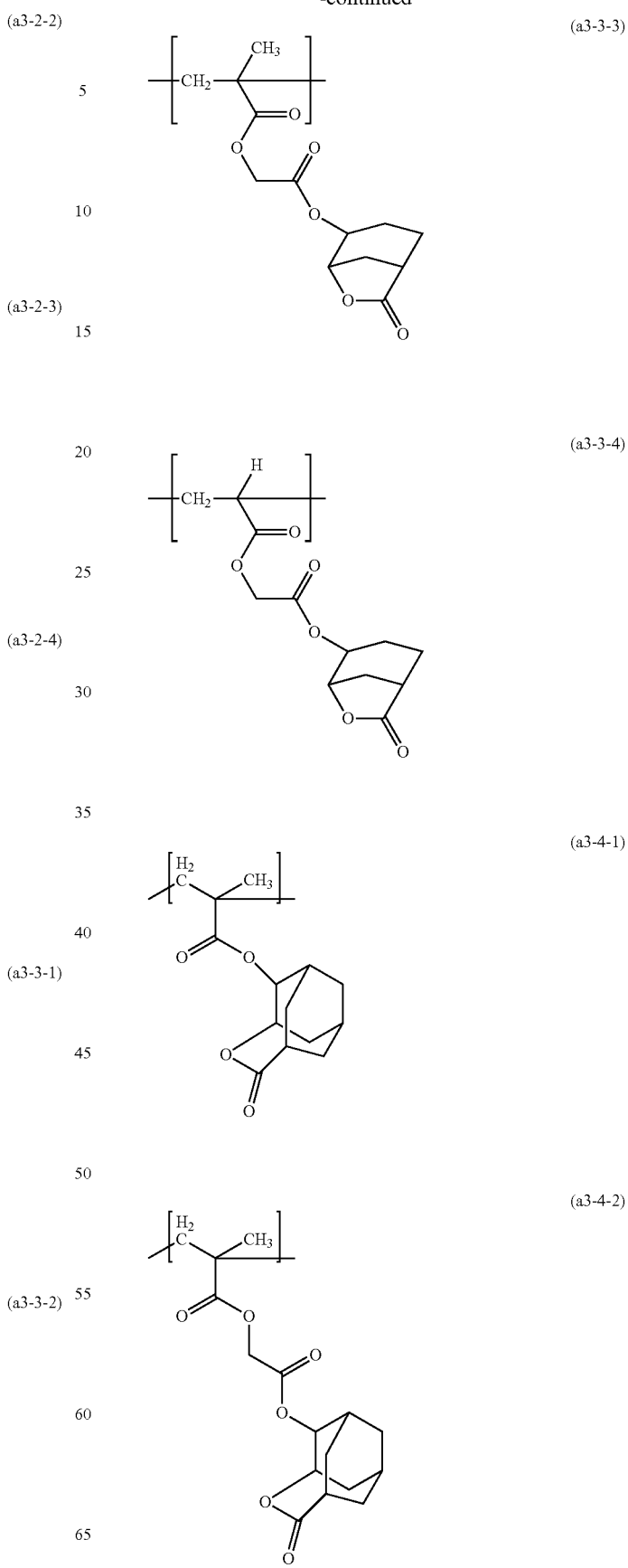

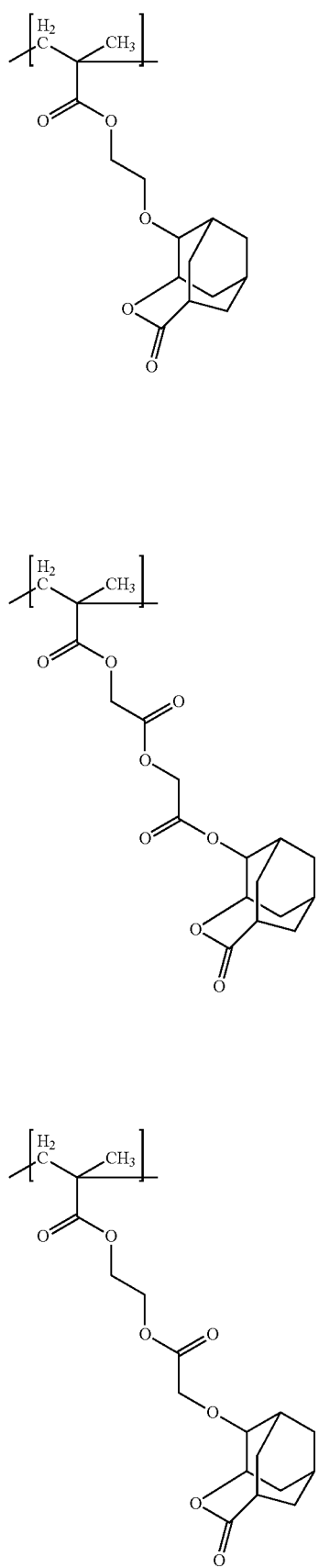
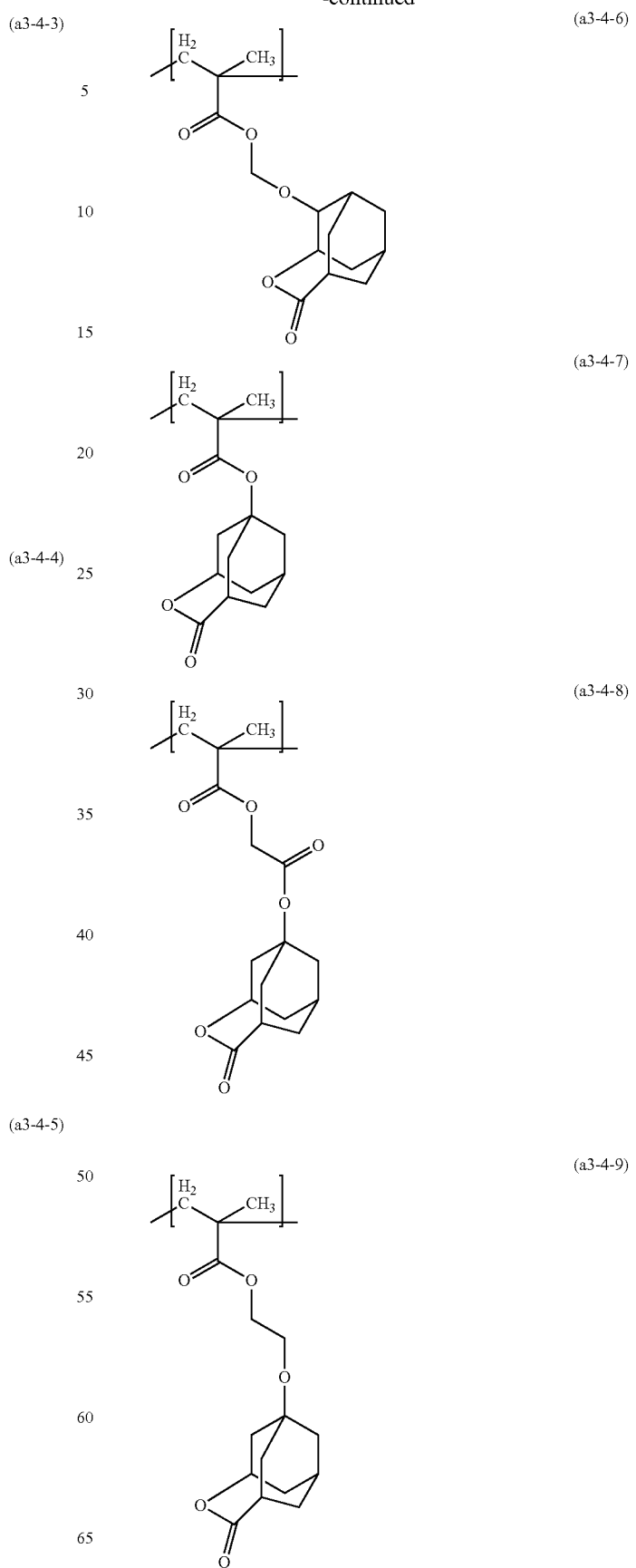

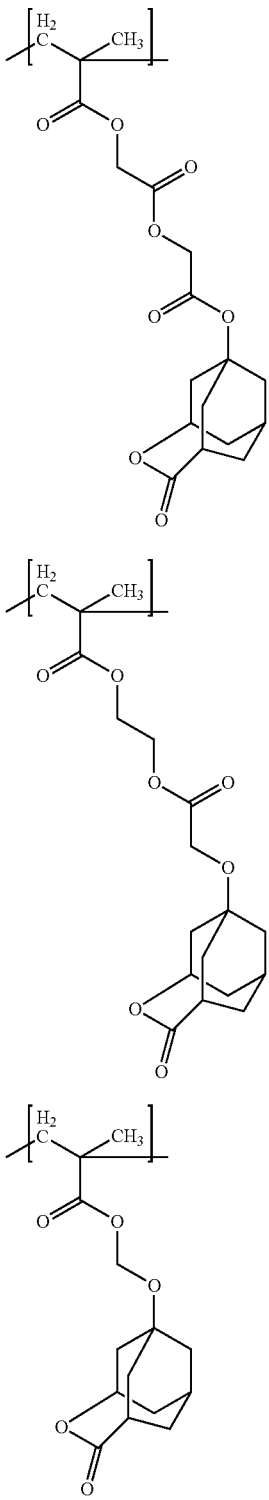

(a3-4-10)

(a3-4-11)

(a3-4-12)

Examples of the structural unit (a3) include the structural units represented by the formula (a3-4-1) to the formula (a3-4-12) in which a methyl group corresponding to $R^{a24}$ has been replaced by a hydrogen atom.

When the resin (A1) further has the structural units (a3), the total proportion thereof is preferably 5% by mole to 70% by mole, more preferably 10% by mole to 65% by mole, still more preferably 10% by mole to 60% by mole, with respect to the total structural units (100% by mole) constituting the resin (A1).

The proportion each of the formula (a3-1), the formula (a3-2), the formula (a3-3) and the formula (a3-4) is preferably 5% by mole to 60% by mole, more preferably 5% by mole to 50% by mole, still more preferably 10% by mole to 50% by mole, with respect to the total structural units (100% by mole) constituting the resin (A1).

<Other Structural Unit (t)>

The resin (A1) may further have a structural unit other than the structural unit (a1) and the structural unit (s) described above. Examples of the structural unit (t) include the structural unit (a4) and the structural unit (a5).

<Structural Unit (a4)>

Examples of the structural unit (a4) include a structural unit represented by formula (a4-0).

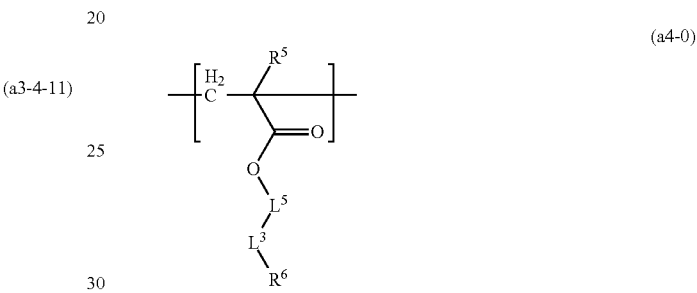

(a4-0)

In the formula (a4-0), $R^5$ represents a hydrogen atom or a methyl group, $L^5$ represents a single bond or a $C_1$ to $C_4$ saturated aliphatic hydrocarbon group, $L^3$ represents a $C_1$ to $C_8$ perfluoroalkanediyl group, a $C_3$ to $C_{12}$ perfluorocycloalkanediyl group or a perfluoroadamantanediyl group, and $R^6$ represents a hydrogen atom or a fluorine atom.

Examples of the saturated aliphatic hydrocarbon group for $L^5$ include $C_1$ to $C_4$ alkanediyl group, i.e., a liner alkanediyl group such as methylene, ethylene, propane-1,3-diyl, butane-1,4-diyl; and a branched alkanediyl group such as a group in which a liner alkanediyl group has a side chain of an alkyl group (e.g., methyl and ethyl groups), for example, ethane-1,1-diyl, propane-1,2-diyl, butane-1,3-diyl, 2-methylpropane-1,3-diyl and 2-methylpropane-1,2-diyl groups.

$L^5$ is preferably a single bond, methylene or ethylene group, and more preferably a single bond or methylene group.

Examples of the perfluoroalkanediyl group for $L^3$ include difluoromethylene, perfluoroethylene, perfluoroethyl fluoromethylene, perfluoropropane-1,3-diyl, a perfluoropropane-1,2-diyl, perfluoropropane-2,2-diyl, perfluorobutane-1,4-diyl, perfluorobutane-2,2-diyl, perfluorobutane-1,2-diyl, perfluoropentane-1,5-diyl, perfluoropentane-2,2-diyl, perfluoropentane-3,3-diyl, perfluorohexane-1,6-diyl, perfluorohexane-2,2-diyl, perfluorohexane-3,3-diyl, perfluoroheptane-1,7-diyl, perfluoroheptane-2,2-diyl, perfluoroheptane-3,4-diyl, perfluoroheptane-4,4-diyl, perfluorooctan-1,8-diyl, perfluorooctan-2,2-diyl, perfluorooctan-3,3-diyl and perfluorooctan-4,4-diyl groups.

Examples of the perfluoro cycloalkanediyl group for $L^3$ include perfluorocyclohexanediyl, perfluorocyclopentanediyl, perfluorocycloheptanediyl and perfluoroadamantanediyl groups.

$L^3$ is preferably a $C_1$ to $C_6$ perfluoroalkanediyl group, more preferably a $C_1$ to $C_3$ perfluoroalkanediyl group.
Examples of the structural unit (a4-0) include the following ones.
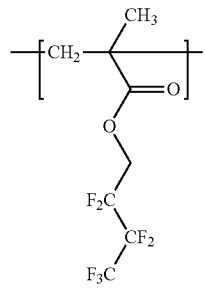
(a4-0-1)
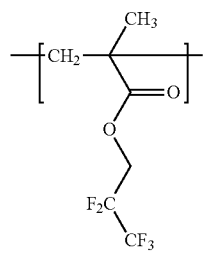
(a4-0-2)
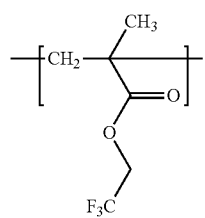
(a4-0-3)
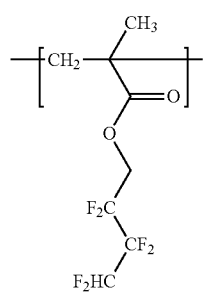
(a4-0-4)
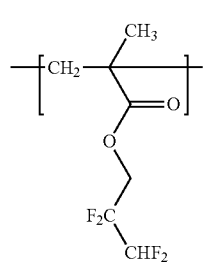
(a4-0-5)
-continued
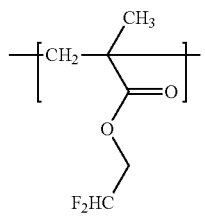
(a4-0-6)
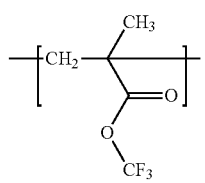
(a4-0-7)
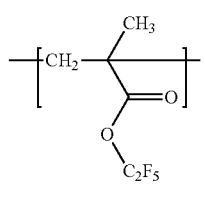
(a4-0-8)
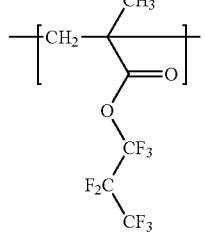
(a4-0-9)
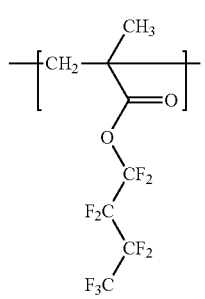
(a4-0-10)
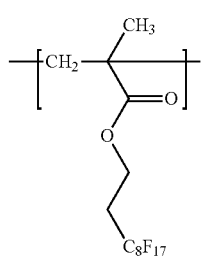
(a4-0-11)
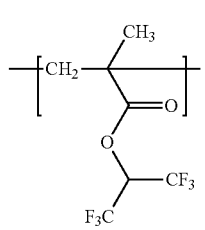
(a4-0-12)

-continued

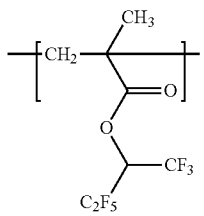
(a4-0-13)

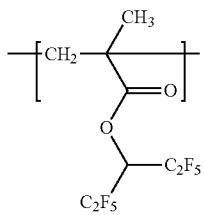
(a4-0-14)

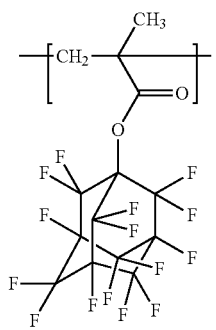
(a4-0-15)

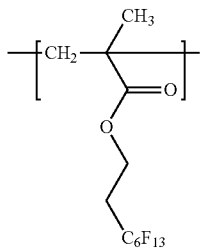
(a4-0-16)

Examples of the structural unit (a4-0) include the structural units represented by the above formulae in which a methyl group corresponding to $R^5$ has been replaced by a hydrogen atom.

Examples of the structural unit (a4) include the structural units represented by formula (a4-1):

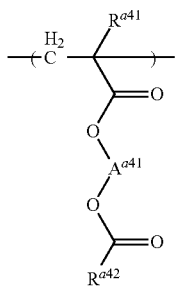
(a4-1)

wherein $R^{a41}$ represents a hydrogen atom or a methyl group, $R^{a42}$ represents an optionally substituted $C_1$ to $C_{20}$ hydrocarbon group where a methylene group may be replaced by an oxygen atom or a carbonyl group, and $A^{a41}$ represents an optionally substituted $C_1$ to $C_6$ alkanediyl group or a group represented by formula (a-g1), $$** \text{—} A^{a42} \text{—} (X^{a41} \text{—} A^{a43})_s \text{—} X^{a42} \text{—} A^{a44} \text{—} * \quad \text{(a-g1)}$$

wherein s represents 0 or 1, $A^{a42}$ and $A^{a44}$ each independently represent an optionally substituted $C_1$ to $C_5$ aliphatic hydrocarbon group, $A^{a43}$ represents a single bond or an optionally substituted $C_1$ to $C_5$ aliphatic hydrocarbon group, and $X^{a41}$ and $X^{a42}$ each independently represent —O—, —CO—, —CO—O— or —O—CO—, provided that the total carbon number contained in $A^{a42}$, $A^{a43}$, $A^{a44}$, $X^{a41}$ and $X^{a42}$ is 7 or less, at least one of $A^{a41}$ and $R^{a42}$ has a halogen atom as a substituent, and

* and ** represent a binding site, and * represents a binding site to —O—CO—$R^{a42}$.

The hydrocarbon group for $R^{a42}$ includes a chain and a cyclic aliphatic hydrocarbon groups, an aromatic hydrocarbon group and a combination thereof.

The chain and the cyclic aliphatic hydrocarbon group may have a carbon-carbon unsaturated bond, and is preferably a chain and a cyclic saturated aliphatic hydrocarbon group. Examples of the saturated aliphatic hydrocarbon group include a liner or branched alkyl group, a monocyclic or polycyclic alicyclic hydrocarbon group, and an aliphatic hydrocarbon group formed by combining the alkyl group and the alicyclic hydrocarbon group.

Examples of the chain aliphatic hydrocarbon group include an alkyl group such as methyl, ethyl, n-propyl, isopropyl, n-butyl, sec-butyl, tert-butyl, pentyl, hexyl, octyl, and 2-ethylhexyl groups, preferably include a $C_1$ to $C_4$ alkyl group, more preferably a methyl group or an ethyl group, and still more preferably a methyl group.

Examples of the alicyclic hydrocarbon group include a cycloalkyl group such as cyclopentyl, cyclohexyl, cycloheptyl, cyclooctyl groups; and polycyclic hydrocarbon groups such as decahydronaphtyl, adamantyl and norbornyl groups as well as groups below. * represents a binding site.

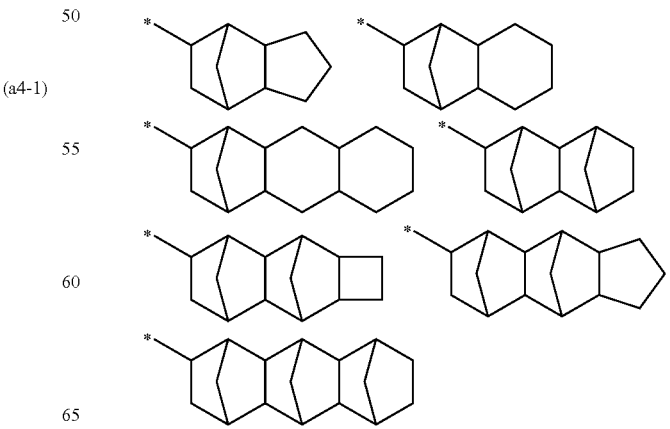

Examples of the aromatic hydrocarbon group include an aryl group such as phenyl, naphthyl, anthryl, biphenyl, phenanthryl and fluorenyl groups.

The hydrocarbon group for $R^{a42}$ is preferably a chain and a cyclic aliphatic hydrocarbon groups, and a combination thereof. The hydrocarbon group may have a carbon-carbon unsaturated bond, is preferably a chain and a cyclic saturated aliphatic hydrocarbon groups, and a combination thereof.

Examples of the substituent for $R^{a42}$ include a halogen atom or a group represented by formula (a-g3):

$$*-X^{a46}-A^{a45} \quad \text{(a-g3)}$$

wherein $X^{a43}$ represent an oxygen atom, a carbonyl group, a carbonyloxy group or an oxycarbonyl group, $A^{a45}$ represents a $C_1$ to $C_{17}$ aliphatic hydrocarbon group that has a halogen atom, and

* represents a binding site.

Examples of the halogen atom for the substituent include fluorine, chlorine, bromine or iodine atom, and preferably a fluorine atom.

Examples of the aliphatic hydrocarbon group for $A^{a45}$ include the same ones as those for $R^{a42}$.

$R^{a42}$ is preferably an aliphatic hydrocarbon group that may have a halogen atom, and more preferably an alkyl group having a halogen atom and/or an aliphatic hydrocarbon group having the group represented by the formula (a-g3).

When $R^{a42}$ is an aliphatic hydrocarbon group having a halogen atom, an aliphatic hydrocarbon group having a fluorine atom is preferred, a perfluoroalkyl group or a perfulorocycloalkyl group are more preferred, a $C_1$ to $C_6$ perfluoroalkyl group is still more preferred, a $C_1$ to $C_3$ perfluoroalkyl group is particularly preferred.

Examples of the perfluoroalkyl group include perfluoromethyl, perfluoroethyl, perfluoropropyl, perfluorobutyl, perfluoropentyl, perfluorohexyl, perfluoroheptyl and perfluorooctyl groups. Examples of the perfluorocycloalkyl group include perfluorocyclohexyl group.

When $R^{a42}$ is an aliphatic hydrocarbon group having the group represented by the formula (a-g3), the total carbon number contained in the aliphatic hydrocarbon group including the group represented by the formula (a-g3) is preferably 15 or less, more preferably 12 or less. The number of the group represented by the formula (a-g3) is preferably one when the group represented by the formula (a-g3) is the substituent.

The aliphatic hydrocarbon group having the group represented by the formula (a-g3) is more preferably a group represented by formula (a-g2):

$$*-A^{a46}-X^{a44}-A^{a47} \quad \text{(a-g2)}$$

wherein $A^{a46}$ represents a $C_1$ to $C_{17}$ aliphatic hydrocarbon group that may have a halogen atom, $X^{a44}$ represent a carbonyloxy group or an oxycarbonyl group, $A^{a47}$ represents a $C_1$ to $C_{17}$ aliphatic hydrocarbon group that may have a halogen atom, provided that the total carbon number contained in $A^{a46}$, $X^{a44}$ and $A^{a47}$ is 18 or less, at least one of $A^{a46}$ and $A^{a47}$ has a halogen atom, and
* represents a binding site to a carbonyl group.

The aliphatic hydrocarbon group for $A^{a46}$ has preferably 1 to 6 carbon atoms, more preferably 1 to 3, carbon atoms.

The he aliphatic hydrocarbon group for $A^{a47}$ has preferably 4 to 15 carbon atoms, more preferably 5 to 12 carbon atoms. $A^{a47}$ is more preferably a cyclohexyl group or an adamantyl group.

Preferred examples of $*-A^{a46}-X^{a44}-A^{a47}$ include the following ones.

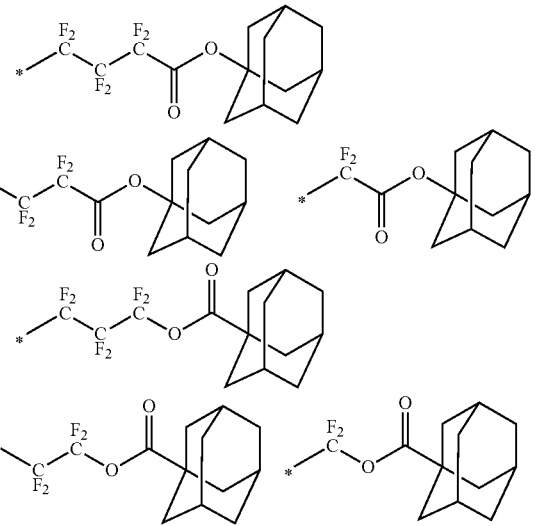

Examples of the alkanediyl group for $A^{a41}$ include a liner alkanediyl group such as methylene, ethylene, propane-1,3-diyl, butane-1,4-diyl, pentane-1,5-diyl and hexane-1,6-diyl groups;

a branched alkanediyl group such as propane-1,2-diyl, butan-1,3-diyl, 2-methylpropane-1,2-diyl, 1-methylbutane-1,4-diyl, 2-methylbutane-1,4-diyl groups.

Examples of the substituent on the alkanediyl group for $A^{a41}$ include a hydroxy group and a $C_1$ to $C_6$ alkoxy group.

Examples of the substituent on the alkanediyl for $A^{a41}$ include a hydroxy group and a $C_1$ to $C_6$ alkoxy group.

$A^{a41}$ is preferably a $C_1$ to $C_4$ alkanediyl group, more preferably a $C_2$ to $C_4$ alkanediyl group, and still more preferably ethylene group.

In the group represented by the formula (a-g1) (which is sometimes referred to as "group (a-g1)"), examples of the aliphatic hydrocarbon group for $A^{a42}$, $A^{a43}$ and $A^{a44}$ include methylene, ethylene, propane-1,3-diyl, propane-1,2-diyl, butane-1,4-diyl, 1-methylpropane-1,3-diyl, 2-methylpropane-1,3-diyl and 2-methylpropane-1,2-diyl groups.

Examples of the substituent in the aliphatic hydrocarbon group for $A^{a42}$, $A^{a43}$ and $A^{a44}$ include a hydroxy group and a $C_1$ to $C_6$ alkoxy group.

s is preferably 0.

Examples of the group (a-g1) in which $X^{a42}$ represents an oxygen atom include the following ones. In the formula, * and  each represent a binding site, and  represents a binding site to $-O-CO-R^{a42}$.

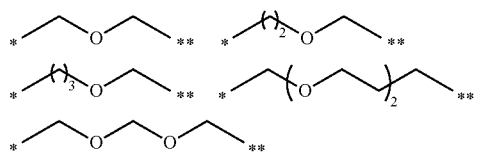

Examples of the group (a-g1) in which $X^{a42}$ represents a carbonyl group include the following ones.

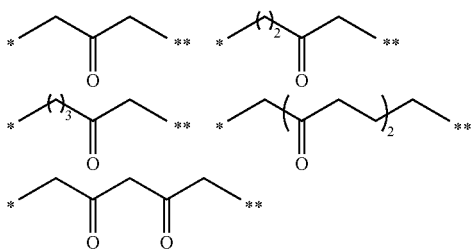

Examples of the group (a-g1) in which $X^{a42}$ represents a carbonyloxy group include the following ones.

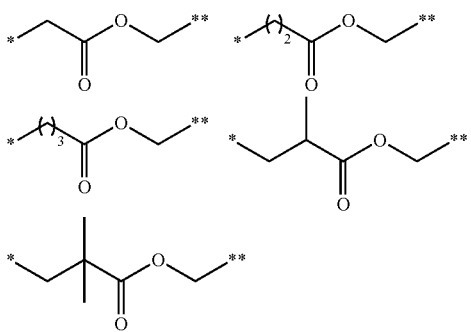

Examples of the group (a-g1) in which $X^{a42}$ represents an oxycarbonyl group include the following ones.

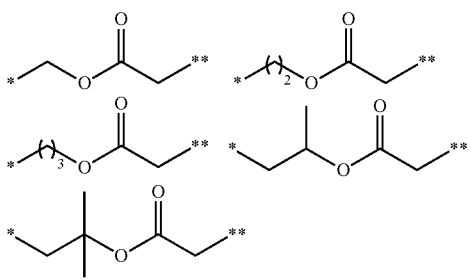

The structural unit represented by the formula (a4-1) is preferably structural units represented by formula (a4-2) and formula (a4-3):

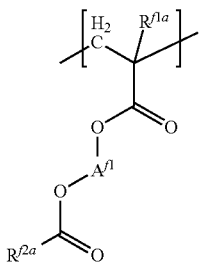

(a4-2)

wherein $R^{f1a}$ represents a hydrogen atom or a methyl group,
$A^{f1}$ represent a $C_1$ to $C_6$ alkanediyl group, and
$R^{f2a}$ represents a $C_1$ to $C_{10}$ hydrocarbon group that has a fluorine atom.

Examples of the alkanediyl group for $A^{f1}$ include a liner alkanediyl group such as methylene, ethylene, propane-1,3-diyl, propane-1,2-diyl, butane-1,4-diyl, pentane-1,5-diyl and hexane-1,6-diyl groups;
a branched alkanediyl group such as 1-methylpropane-1,3-diyl, 2-methylpropane-1,3-diyl, 2-methylpropane-1,2-diyl, 1-methylbutane-1,4-diyl and 2-methylbutane-1,4-diyl groups.

The hydrocarbon group for $R^{f2a}$ includes an aliphatic hydrocarbon group and an aromatic hydrocarbon group. The aliphatic hydrocarbon group includes a chain and cyclic groups, and a combination thereof. The aliphatic hydrocarbon group is preferably an alkyl group and a cyclic aliphatic hydrocarbon group.

Examples of the alkyl group include methyl, ethyl, n-propyl, isopropyl, n-butyl, sec-butyl, tert-butyl, n-pentyl, n-hexyl, n-heptyl, n-octyl and 2-ethylhexyl groups.

Examples of the cyclic aliphatic hydrocarbon group include any of a monocyclic group and a polycyclic group. Examples of the monocyclic alicyclic hydrocarbon group include a cycloalkyl group such as cyclopropyl, cyclobutyl, cyclopentyl, cyclohexyl, methylcyclohexyl, dimethylcyclohexyl, cycloheptyl, cyclooctyl, and cyclodecyl groups. Examples of the polycyclic hydrocarbon groups includes decahydronaphthyl, adamantyl, 2-alkyladamantane-2-yl, 1-(adamantane-1-yl)alkane-1-yl, norbornyl, methylnorbornyl and isobornyl groups.

Examples of the hydrocarbon group having a fluorine atom for $R^{f2a}$ include an alkyl group having a fluorine atom and an alicyclic hydrocarbon group having a fluorine atom.

Specific examples of an alkyl group having a fluorine atom include a fluorinated alkyl group such as difluoromethyl, trifluoromethyl, 1,1-difluoroethyl, 2,2-difluoroethyl, 2,2,2-trifluoroethyl, perfluoroethyl, 1,1,2,2-tetrafluoropropyl, 1,1,2,2,3,3-hexafluoropropyl, perfluoroethylmethyl, 1-(trifluoromethyl)-1,2,2,2-tetrafluoroethyl, perfluoropropyl, 1-(trifluoromethyl)-2,2,2-trifluoroethyl, perfluoropropyl, 1,1,2,2-tetrafluorobutyl, 1,1,2,2,3,3-hexafluorobutyl, 1,1,2,2,3,3,4,4-octafluorobutyl, perfluorobutyl, 1,1-bis(trifluoro)methyl-2,2,2-trifluoroethyl, 2-(perfluoropropyl)ethyl, 1,1,2,2,3,3,4,4-octafluoropentyl, perfluoropentyl, 1,1,2,2,3,3,4,4,5,5-decafluoropentyl, 1,1-bis(trifluoromethyl)2,2,3,3,3-pentafluoropropyl, 2-(perfluorobutyl)ethyl, 1,1,2,2,3,3,4,4,5,5-decafluorohexyl, 1,1,2,2,3,3,4,4,5,5,6,6-dodecafluorohexyl, perfluoropentylmethyl and perfluorohexyl groups.

Examples of the alicyclic hydrocarbon group having a fluorine atom include a fluorinated cycloalkyl group such as perfluorocyclohexyl and perfluoroadamantyl groups.

In the formula (a4-2), $A^n$ is preferably a $C_2$ to $C_4$ alkanediyl group, and more preferably an ethylene group.
$R^{f2a}$ is preferably a $C_1$ to $C_6$ fluorinated alkyl group.

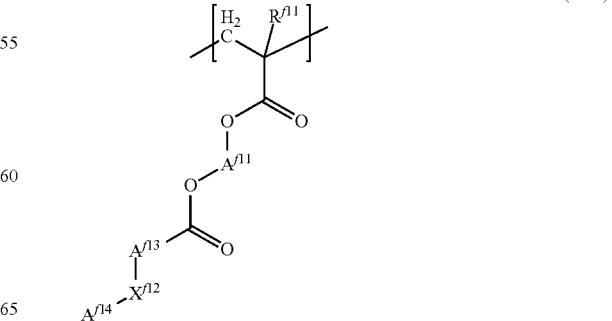

(a4-3)

In the formula (a4-3), $R^{f11}$ represents a hydrogen atom or a methyl group, $A^{f11}$ represent a $C_1$ to $C_6$ alkanediyl group, $A^{f13}$ represents a $C_1$ to $C_{18}$ aliphatic hydrocarbon group that may have a fluorine atom, $X^{f12}$ represents an oxycarbonyl group or a carbonyloxy group, $A^{f14}$ represents a $C_1$ to $C_{17}$ aliphatic hydrocarbon group that may have a fluorine atom, and provided that at least one of $A^{f13}$ and $A^{f14}$ represents an aliphatic hydrocarbon group having a fluorine atom.

Examples of the alkanediyl group for $A^{f11}$ include the same ones as those for $A^{f1}$.

Examples of the aliphatic hydrocarbon group for $A^{f13}$ include any of a divalent chain or cyclic aliphatic hydrocarbon group, or a divalent aliphatic hydrocarbon group formed by combination thereof. The aliphatic hydrocarbon group may have a carbon-carbon unsaturated bond, and is preferably a saturated aliphatic hydrocarbon group.

The aliphatic hydrocarbon group that may have a fluorine atom for $A^{f13}$ is preferably the saturated aliphatic hydrocarbon group that may have a fluorine atom, and more preferably a perfluoroalkandiyl group.

Examples of the divalent chain aliphatic hydrocarbon that may have a fluorine atom include an alkanediyl group such as methylene, ethylene, propanediyl, butanediyl and pentanediyl groups; a perfluoroalkanediyl group such as difluoromethylene, perfluoroethylene, perfluoropropanediyl, perfluorobutanediyl and perfluoropentanediyl groups.

The divalent cyclic aliphatic hydrocarbon group that may have a fluorine atom is any of monocyclic or polycyclic group.

Examples monocyclic aliphatic hydrocarbon group include cyclohexanediyl and perfluorocyclohexanediyl groups.

Examples polycyclic aliphatic hydrocarbon group include adamantanediyl, norbornanediyl, and perfluoroadamantanediyl groups.

Examples of the aliphatic hydrocarbon group for $A^{f14}$ include any of a chain or a cyclic aliphatic hydrocarbon group, or a combination thereof. The aliphatic hydrocarbon group may have a carbon-carbon unsaturated bond, and is preferably a saturated aliphatic hydrocarbon group.

The aliphatic hydrocarbon group that may have a fluorine atom of $A^{f14}$ is preferably the saturated aliphatic hydrocarbon group that may have a fluorine atom.

Examples of the chain aliphatic hydrocarbon group that may have a halogen atom include trifluoromethyl, difluoromethyl, methyl, perfluoromethyl, 1,1,1-trifluoroethyl, 1,1,2,2-tetrafluoroethyl, ethyl, perfluoropropyl, 1,1,1,2,2-pentafluoropropyl, propyl, perfluorobutyl, 1,1,2,2,3,3,4,4-octafluorobutyl, butyl, perfluoropentyl, 1,1,1,2,2,3,3,4,4-nonafluoropentyl, pentyl, hexyl, perfluorohexyl, hepthyl, perfluoroheptyl, octyl and perfluorooctyl groups.

The cyclic aliphatic hydrocarbon group that may have a fluorine atom may be any of a monocyclic group and a polycyclic group. Examples of the group containing the monocyclic aliphatic hydrocarbon group include cyclopropylmethyl, cyclopropyl, cyclobutylmethyl, cyclopentyl, cyclohexyl and perfluorocyclohexyl groups. Examples of the group containing the polycyclic aliphatic hydrocarbon group includes adamantyl, adamantylmethyl, norbornyl, norbornylmethyl, perfluoroadamantyl and perfluoroadamantylmethyl groups In the formula (a4-3), $A^{f11}$ is preferably an ethylene group.

The aliphatic hydrocarbon group for $A^{f13}$ is preferably a $C_1$ to $C_6$ aliphatic hydrocarbon group, more preferably a $C_2$ to $C_3$ aliphatic hydrocarbon group.

The aliphatic hydrocarbon group for $A^{f14}$ is preferably a $C_3$ to $C_{12}$ aliphatic hydrocarbon group, more preferably a $C_3$ to $C_{10}$ aliphatic hydrocarbon group. Among these, $A^{f14}$ is preferably a group containing a $C_3$ to $C_{12}$ alicyclic hydrocarbon group, more preferably cyclopropylmethyl, cyclopentyl, cyclohexyl, norbornyl and adamantyl groups.

Examples of the structural unit (a4-2) include structural units represented by formula (a4-1-1) to formula (a4-1-22).

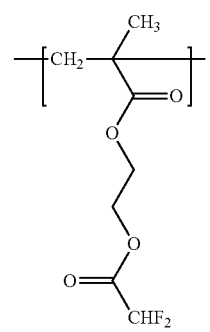

(a4-1-1)

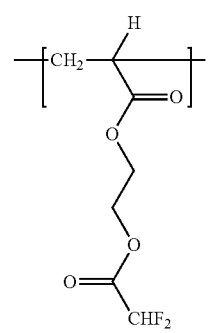

(a4-1-2)

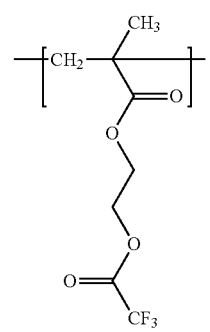

(a4-1-3)

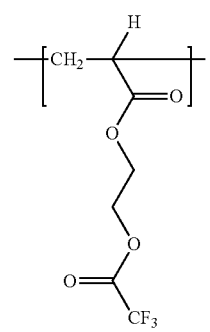

(a4-1-4)

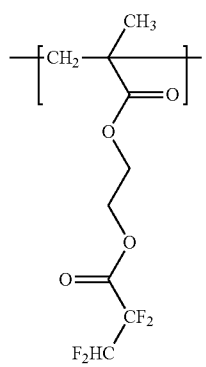 (a4-1-5)
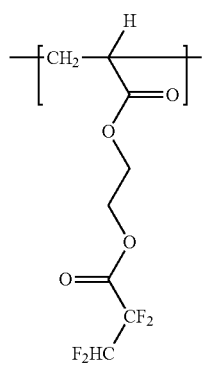 (a4-1-6)
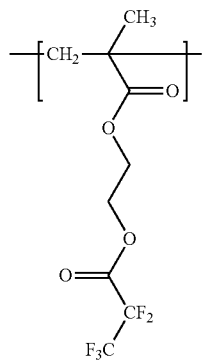 (a4-1-7)
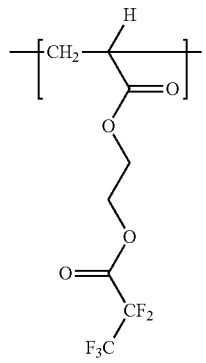 (a4-1-8)
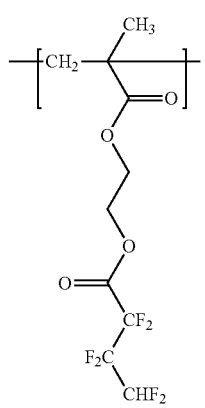 (a4-1-9)
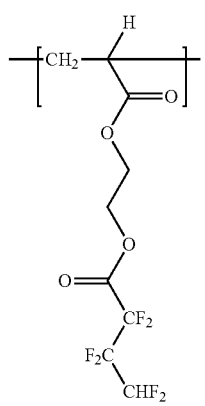 (a4-1-10)
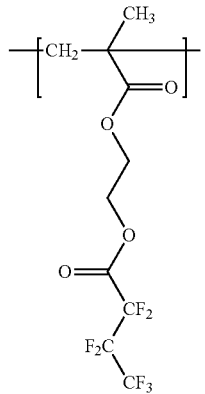 (a4-1-11)
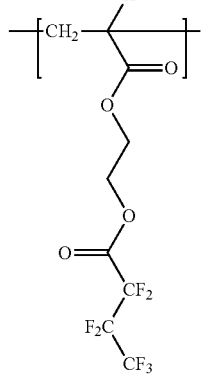 (a4-1-12)

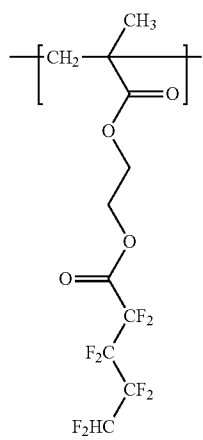
(a4-1-13)
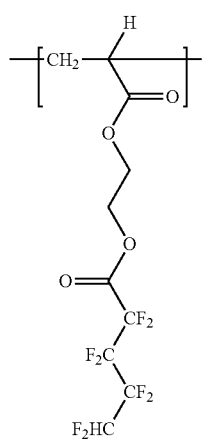
(a4-1-14)
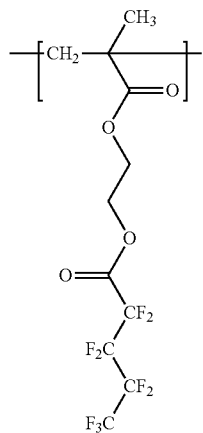
(a4-1-15)
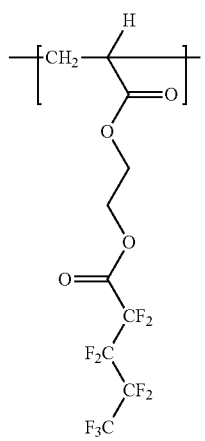
(a4-1-16)
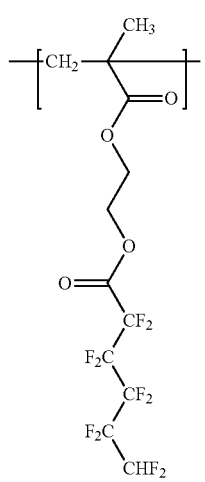
(a4-1-17)
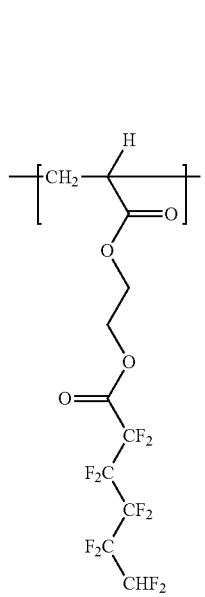
(a4-1-18)

(a4-1-19)
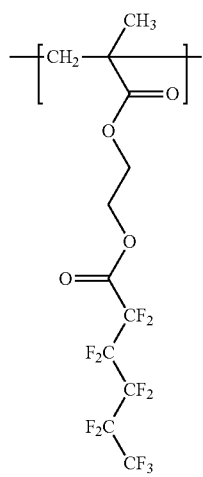
(a4-1-22)
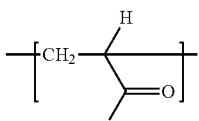
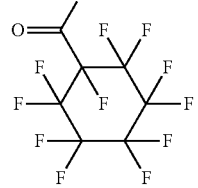
Examples of the structural unit (a4-3) include structural units presented by formula (a4-1'-1) to formula (A4-1'-22).
(a4-1-20)
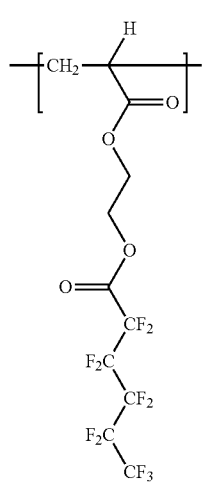
(a4-1'-1)
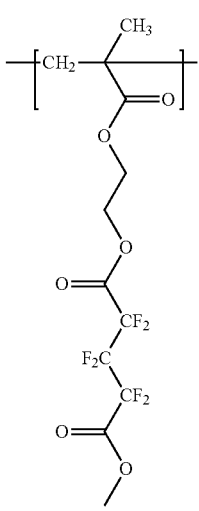
(a4-1-21)
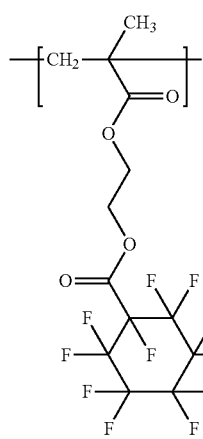
(a4-1'-2)
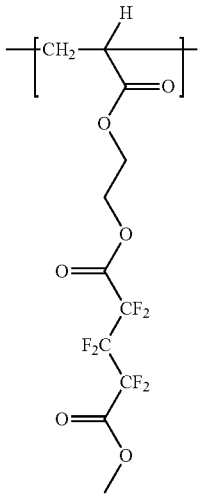

(a4-1'-3)
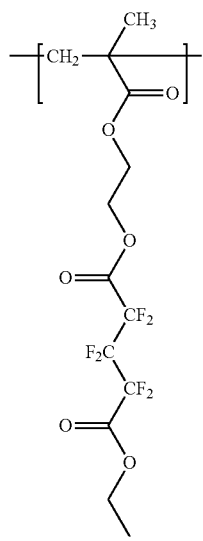
(a4-1'-4)
(a4-1'-5)
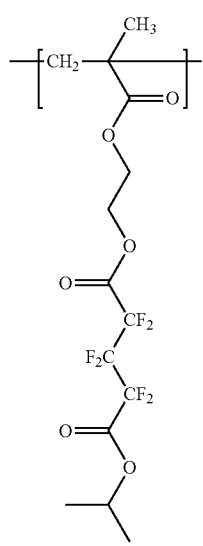
(a4-1'-6)
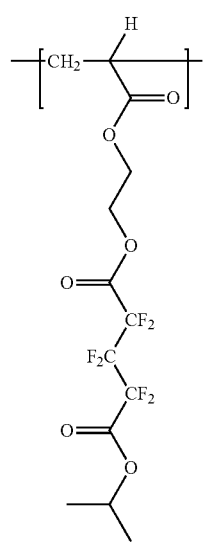
(a4-1'-7)

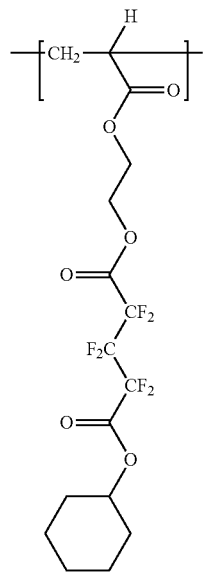
(a4-1'-8)
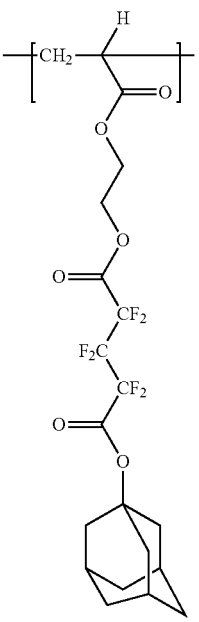
(a4-1'-10)
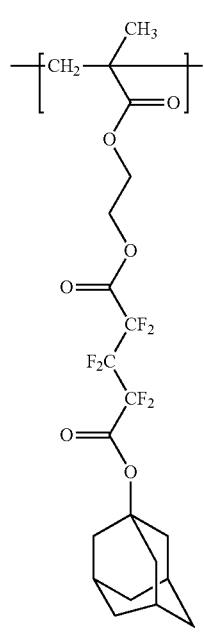
(a4-1'-9)
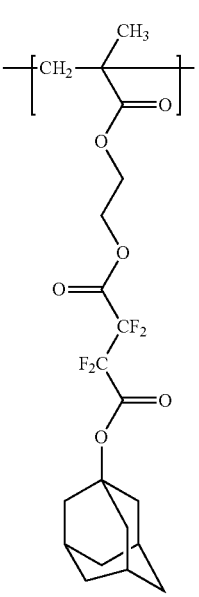
(a4-1'-11)

(a4-1'-12) 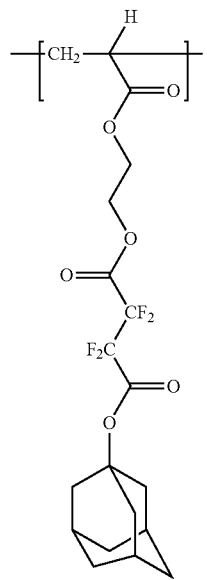
(a4-1'-13) 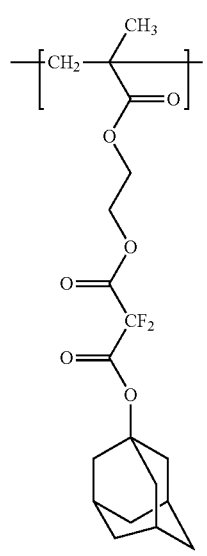
(a4-1'-14) 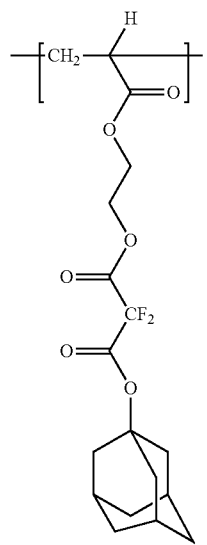
(a4-1'-15) 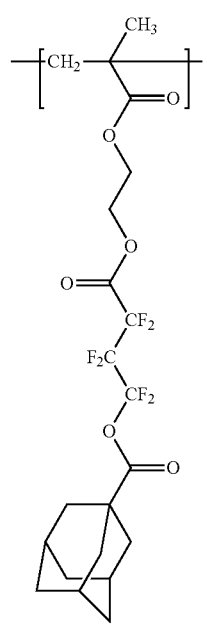
(a4-1'-16) 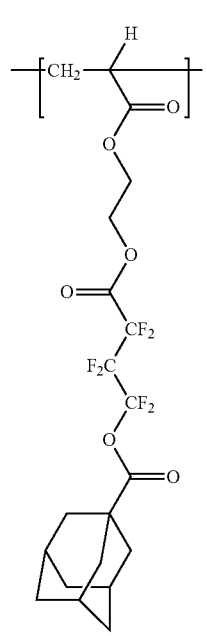

(a4-1'-17)
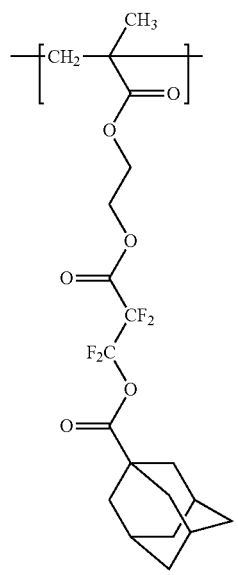
(a4-1'-18)
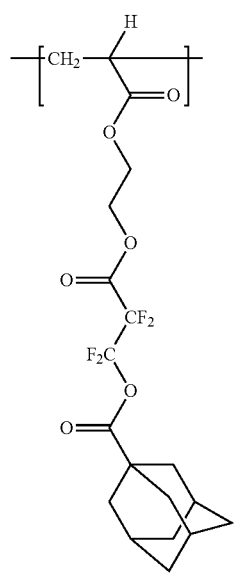
(a4-1'-19)
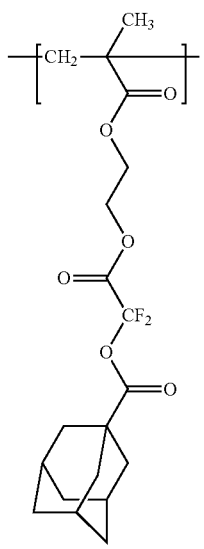
(a4-1'-20)
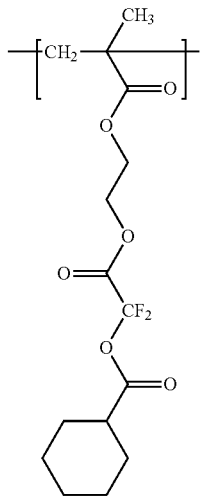
(a4-1'-21)

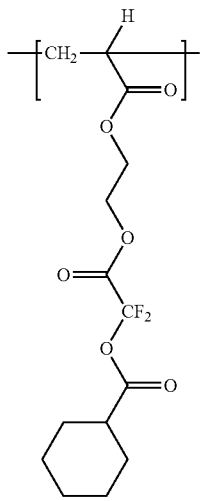

(a4-1'-22)

Examples of the structural unit (a4) include a structural unit presented by formula (a4-4):

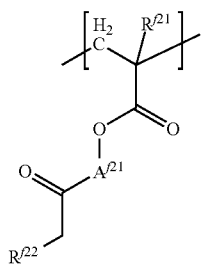

(a4-4)

wherein $R^{f21}$ represents a hydrogen atom or a methyl group, $A^{f21}$ represents *—$(CH_2)$*—$(CH_2)_{j2}$—O—$(CH_2)_{j3}$— or *—$(CH_2)_{j4}$—CO—O—$(CH_2)_{j5}$—, where * represents a binding site to an oxygen atom, j1 to j5 each independently represents an integer of 1 to 6, and $R^{f22}$ represents a $C_1$ to $C_{10}$ hydrocarbon group having a fluorine atom.

Examples of the hydrocarbon group having a fluorine atom for $R^{f22}$ include the same ones as those for $R^{f2}$ in the formula (a4-2). $R^{f22}$ is preferably a $C_1$ to $C_{10}$ alkyl group having a fluorine atom or a $C_3$ to $C_{10}$ alicyclic hydrocarbon group having a fluorine atom, more preferably a $C_1$ to $C_{10}$ alkyl group having a fluorine atom, and still more preferably a $C_1$ to $C_6$ alkyl group having a fluorine atom.

In the formula (a4-4), $A^{f21}$ is preferably —$(CH_2)_{j1}$—, more preferably a methylene group or an ethylene group, and still more preferably a methylene group.

Examples of the structural unit represented by the formula (a4-4) include the following ones.

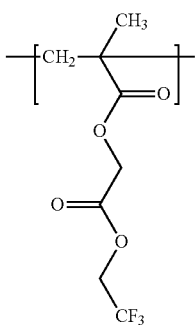

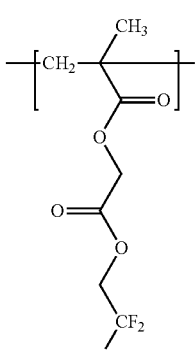

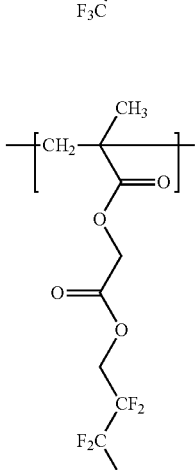

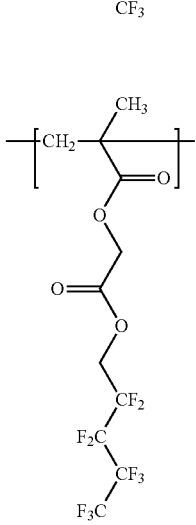

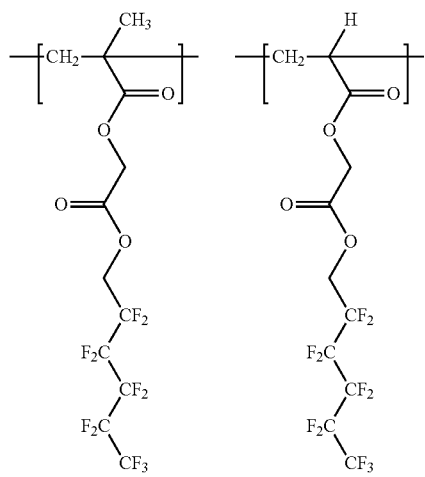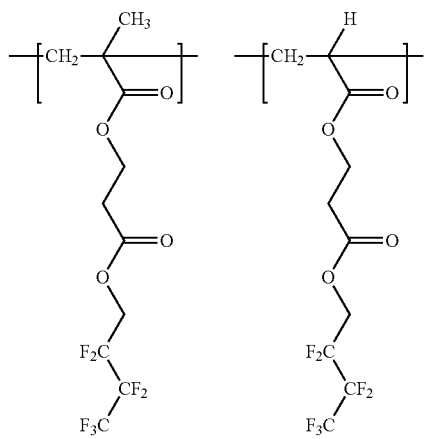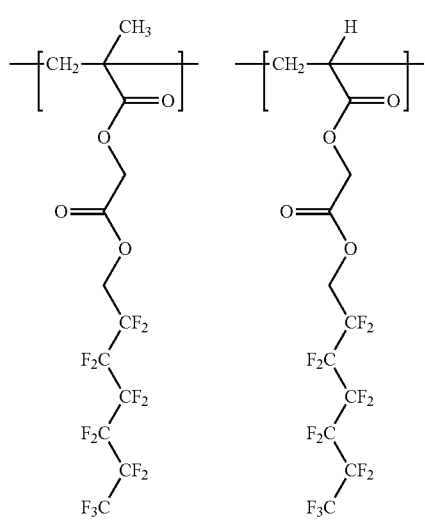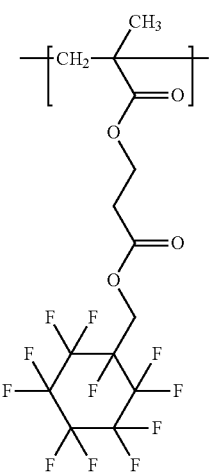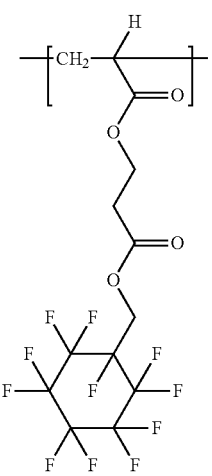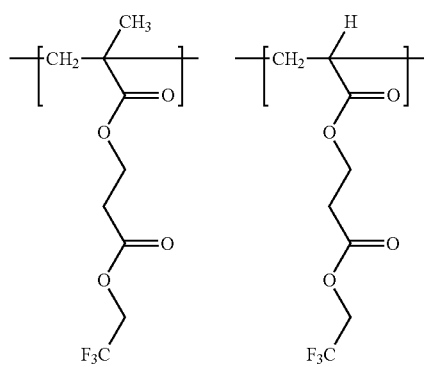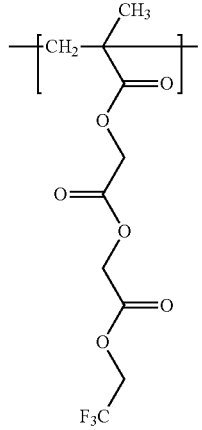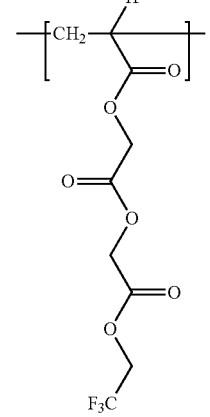

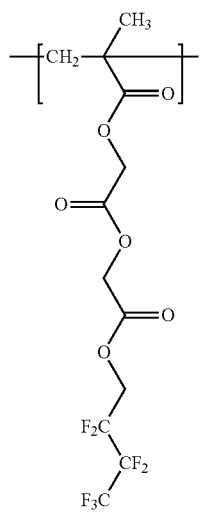 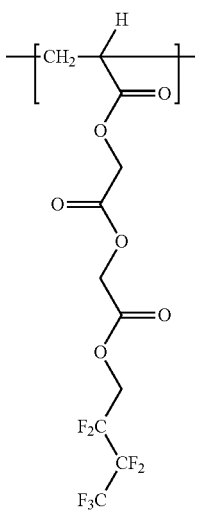 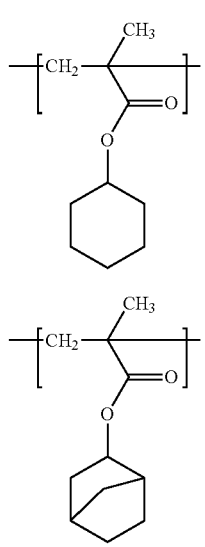
(a5-1-2)
(a5-1-3)
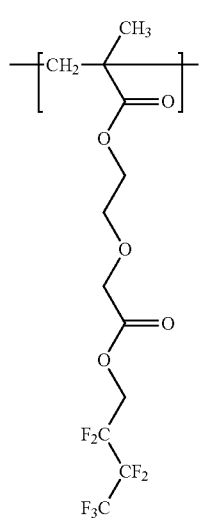 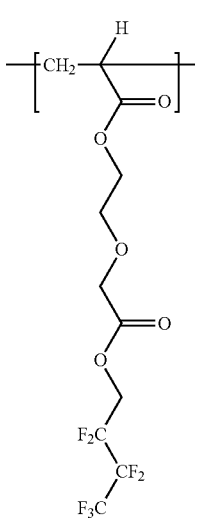
(a5-1-4)
<Structural Unit (a5)>
Examples of the non-leaving hydrocarbon group in the structural unit (a5) include a liner or branched, or a cyclic hydrocarbon group. Among these, the structural unit (a5) is preferably a structural unit containing an alicyclic hydrocarbon group.
Examples of the structural unit (a5) include the following ones.
(a5-1-5)
(a5-1-1)
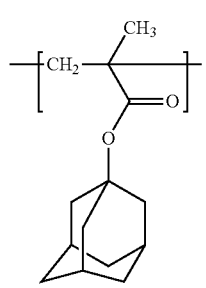
(a5-1-6)
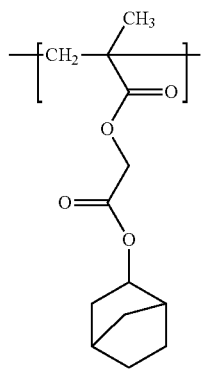

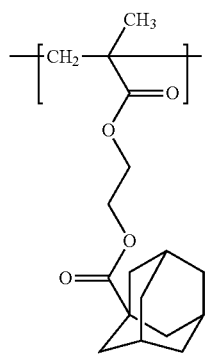
(a5-1-7)
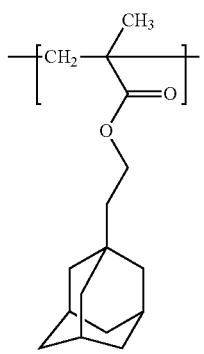
(a5-1-11)
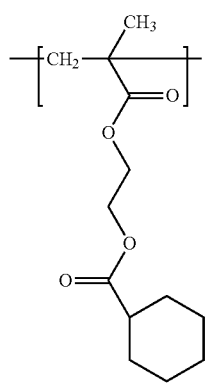
(a5-1-8)
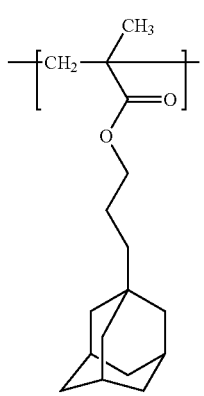
(a5-1-12)
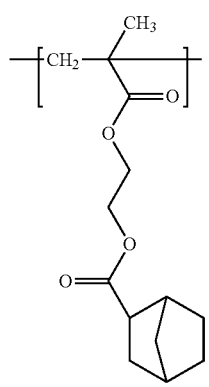
(a5-1-9)
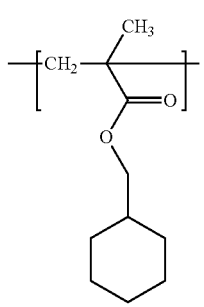
(a5-1-13)
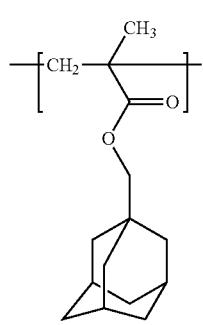
(a5-1-10)
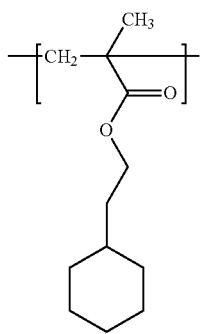
(a5-1-14)

-continued (a5-1-15)
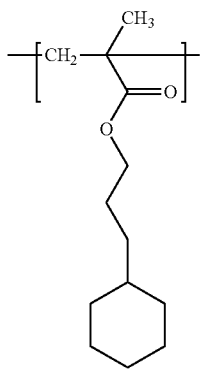

(a5-1-16)
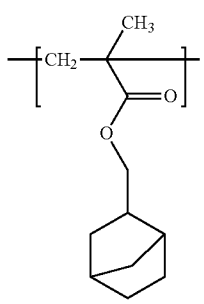

(a5-1-17)
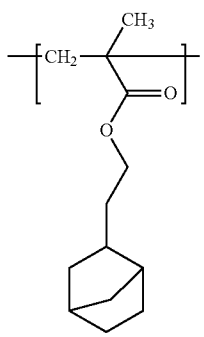

(a5-1-18)
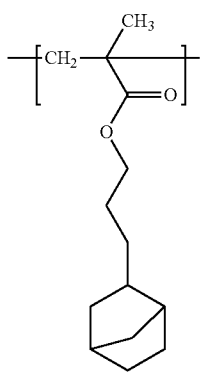

Examples of the structural units (a5) include structural units represented by the above formulae in which a methyl group corresponding to, for example, $R'^{21}$ in the formula (a4-4) has been replaced by a hydrogen atom.

When the resin (A1) has the structural unit (a4), the proportion thereof is generally 1 to 20% by mole, preferably 2 to 15% by mole, more preferably 3 to 10% by mole, with respect to the total structural units (100% by mole) of the resin (A1).

When the resin (A1) has the structural unit (a5), the proportion thereof is preferably 10 to 30% by mole, more preferably 2 to 20% by mole, still more preferably 3 to 15% by mole, with respect to the total structural units (100% by mole) of the resin (A1).

The resin (A1) is preferably a resin having the structural unit (a1) and the structural unit (s), that is, a copolymer of the monomer (a1) and the monomer (s). In this copolymer, the structural unit (a1) is preferably at least one of the structural unit (a1-0), the structural unit (a1-1), the structural unit (a1-2) (preferably the structural unit having a cyclohexyl group or a cyclopentyl group) and the structural unit (a1-5), and more preferably is the structural unit (a1-1) or the structural unit (a1-2) (preferably the structural unit having a cyclohexyl group or a cyclopentyl group).

The structural unit (s) is preferably at least one of the structural unit (a2) and the structural unit (a3). The structural unit (a2) is preferably the structural unit represented by the formula (a2-1). The structural unit (a3) is preferably the structural unit having at least one of a γ-butyrolactone ring, a bridged ring including a γ-butyrolactone ring or an adamantane lactone ring.

The proportion of the structural unit derived from the monomer having an adamantyl group (in particular, the structural unit (a1-1)) in the resin (A1) is preferably 15% by mole or more with respect to the structural units (a1). As the mole ratio of the structural unit derived from the monomer having an adamantyl group increases within this range, the dry etching resistance of the resulting resist improves.

The resin (A1) can be produced by a known polymerization method, for example, radical polymerization method, using one or more species of monomers inducing the structural units as described above. The proportion of the structural unit in the resin (A1) can be adjusted by changing the amount of a monomer used in polymerization.

The weight average molecular weight of the resin (A1) is preferably 2,000 or more (more preferably 2,500 or more, and still more preferably 3,000 or more), and 50,000 or less (more preferably 30,000 or less, and still more preferably 15,000 or less). In the present specification, the weight average molecular weight is a value determined by gel permeation chromatography using polystyrene as the standard product. The detailed condition of this analysis is described in Examples.

<Resin (A2)>

The resin (A2) includes a structural unit represented by the formula (I) (which is sometimes referred to as "structural unit (I)").

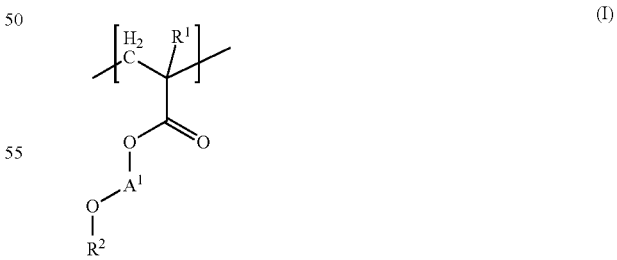
(I)

In the formula, $R^1$ represents a hydrogen atom, a halogen atom or a $C_1$ to $C_6$ alkyl group in which a hydrogen atom can be replaced by a halogen atom, $R^2$ represents a $C_1$ to $C_{12}$ fluorinated saturated hydrocarbon group, $A^1$ represents a $C_2$ to $C_6$ alkanediyl group or *-$A^2$-$X^1$-$(A^3$-$X^2)_a$-$A^4$-, \* represents a binding site to an oxygen atom in —O—CO—, $A^2$, $A^3$ and $A^4$ each independently represent a $C_1$ to $C_6$ alkanediyl group, $X^1$ and $X^2$ each independently represent —O—, —CO—O— or —O—CO—, and a represents 0 or 1.

Examples of the alkyl group for $R^1$ include methyl, ethyl, n-propyl, isopropyl, n-butyl, sec-butyl, tert-butyl, n-pentyl and n-hexyl groups, the alkyl group is preferably a $C_1$ to $C_4$ alkyl group, and more preferably a methyl group or an ethyl group.

Examples of the halogen atom for $R^1$ include fluorine, chlorine, bromine or iodine atom.

Examples of an alkyl group that has a halogen atom include trifluoromethyl, perfluoroethyl, perfluoropropyl, perfluoroisopropyl, perfluorobutyl, perfluoro sec-butyl, perfluoro tert-butyl, perfluoropentyl, perfluorohexyl, perchloromethyl, perbromomethyl and periodomethyl groups.

$R^1$ is preferably a hydrogen atom or a methyl group.

Examples of the fluorinated saturated hydrocarbon group for $R^2$ include difluoromethyl, trifluoromethyl, 1,1-difluoroethyl, 2,2-difluoroethyl, 2,2,2-trifluoroethyl, perfluoroethyl, 1,1,2,2-tetrafluoropropyl, 1,1,2,2,3,3-hexafluoropropyl, perfluoroethylmethyl, 1-(trifluoromethyl)-2,2,2-trifluoroethyl, 1-(trifluoromethyl)-2,2,3,3,3-pentafluoropropyl, 1-(perfluoropropyl)ethyl-2,2,3,3,3-pentafluoropropyl, 1-(trifluoromethyl)-2,2,2-trifluoroethyl, 1-(trifluoromethyl)-1,2,2,2-tetrafluoroethyl, perfluoropropyl, 1,1,2,2-tetrafluorobutyl, 1,1,2,2,3,3-hexafluorobutyl, 1,1,2,2,3,3,4,4-octafluorobutyl, perfluorobutyl, 1,1-bis(trifluoro)methyl-2,2,2-trifluoroethyl, 2-(perfluoropropyl)ethyl, 1,1,2,2,3,3,4,4-octafluoropentyl, perfluoropentyl, 1,1,2,2,3,3,4,4,5,5-decafluoropentyl, 1,1-bis(trifluoromethyl)2,2,3,3,3-pentafluoropropyl, 2-(perfluorobutyl)ethyl, 1,1,2,2,3,3,4,4,5,5-decafluorohexyl, 1,1,2,2,3,3,4,4,5,5,6,6-dodeca fluorohexyl, perfluoropentylmethyl, perfluorohexyl, perfluorocyclohexyl and perfluoroamdamantyl groups.

Among these, $R^2$ is preferably a $C_1$ to $C_{12}$ fluorinated alkyl group, more preferably —$(CH_2)_n$-$R^f$ or —$CH(R^{f1})(R^{f2})$, and still more preferably —$CH(R^{f1})(R^{f2})$.

n represents an integer of 0 to 6, preferably an integer of 0 to 4, more preferably an integer of 0 to 2, still more preferably 0 or 1, and further still more preferably 1.

$R^f$ represents a $C_1$ to $C_6$ perfluoroalkyl group, preferably a $C_1$ to $C_4$ perfluoroalkyl group, more preferably a $C_2$ to $C_4$ perfluoroalkyl group, and still more preferably a $C_3$ to $C_4$ perfluoroalkyl group.

$R^{f1}$ and $R^{f2}$ each independently represent a $C_1$ to $C_6$ perfluoroalkyl group, preferably a $C_1$ to $C_4$ perfluoroalkyl group, more preferably a $C_1$ to $C_3$ perfluoroalkyl group, and still more preferably a $C_1$ to $C_2$ perfluoroalkyl group.

$R_2$ is preferably —$CH_2$—$R^f$ or *—$CHCF_3CF_3$.

Examples of the alkanediyl group for $A^1$ include a liner alkanediyl group such as ethylene, propane-1,3-diyl, butane-1,4-diyl, pentane-1,5-diyl and hexane-1,6-diyl groups;

a branched alkanediyl group such as a group in which a liner alkanediyl group has, as a side chain, an alkyl group (e.g., a $C_1$ to $C_4$ alkyl group, i.e., methyl, ethyl, n-propyl, isopropyl, n-butyl, sec-butyl, tert-butyl groups), for example, ethane-1,1-diyl, propane-1,2-diyl, butane-1,3-diyl, 2-methylpropane-1,3-diyl, 2-methylpropane-1,2-diyl, pentane-1,4-diyl and 2-methylbutane-1,4-diyl groups.

Examples of the alkanediyl group for $A^2$, $A^3$ and $A^4$ include a liner alkanediyl group such as methylene, ethylene, propane-1,3-diyl, butane-1,4-diyl, pentane-1,5-diyl and hexane-1,6-diyl groups;

a branched alkanediyl group such as a group in which a liner alkanediyl group has a side chain of an alkyl group (e.g., a $C_1$ to $C_4$ alkyl group, i.e., methyl, ethyl, n-propyl, isopropyl, n-butyl, sec-butyl, tert-butyl groups), for example, ethane-1,1-diyl, propane-1,2-diyl, butane-1,3-diyl, 2-methylpropane-1,3-diyl, 2-methylpropane-1,2-diyl, pentane-1,4-diyl and 2-methylbutane-1,4-diyl groups.

Examples of *-$A^2$-$X^1$-$(A^3$-$X^2)_a$-$A^4$- include *-$A^2$-CO—O-$A^4$-, *-$A^2$-O-$A^4$-, *-$A^2$-O—CO-$A^4$-, *-$A^2$-CO—O-$A^3$-CO—O-$A^4$-, *-$A^2$-O-$A^3$-CO—O-$A^4$-, *-$A^2$-CO—O-$A^3$-O-$A^4$-. Among these, *-$A^2$-CO—O-$A^4$- and *-$A^2$-O-$A^4$- are preferred. * represents a binding site to an oxygen atom in —O—CO—.

$A^2$, $A^3$ and $A^4$ are preferably a $C_1$ to $C_4$ alkanediyl group.

$A^1$ is preferably a $C_2$ to $C_6$ alkanediyl group, *-$A^2$-CO—O-$A^4$- or *-$A^2$-O-$A^4$-, more preferably a $C_2$ to $C_6$ alkanediyl group, and still more preferably an ethylene group or a propanediyl group.

Examples of the structural unit (I) include the following ones.

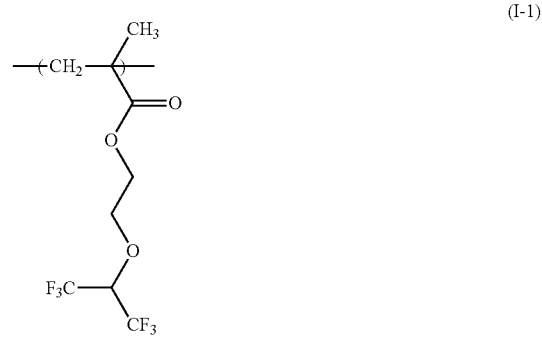

(I-1)

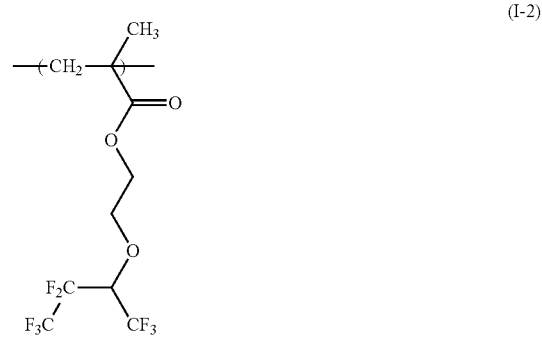

(I-2)

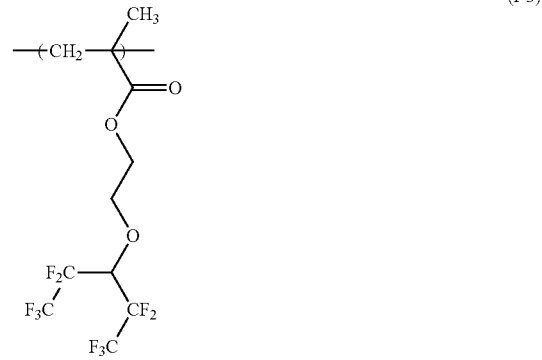

(I-3)

(I-4) 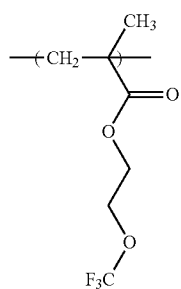
(I-5) 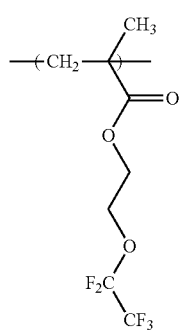
(I-6) 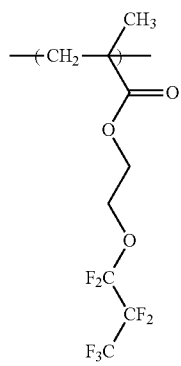
(I-7) 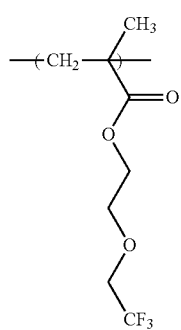
(I-8) 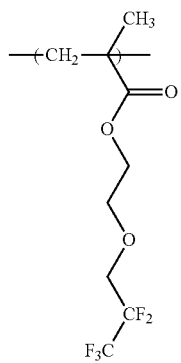
(I-9) 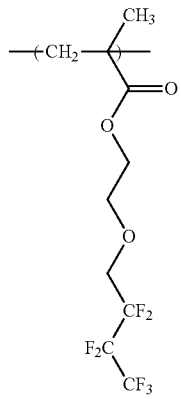
(I-10) 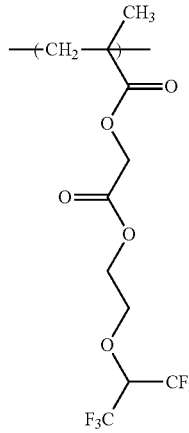
(I-11) 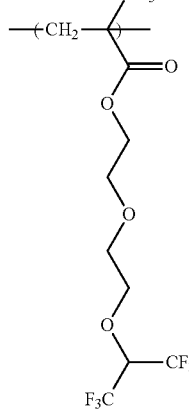

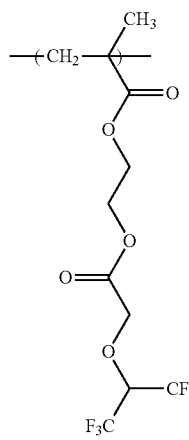
(I-12)

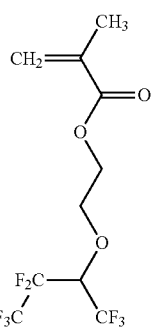
(I'-2)

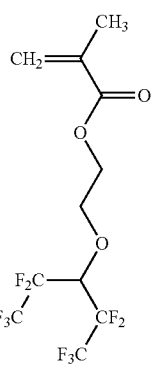
(I'-3)

Examples of the structural units (1) include structural units represented by the above formulae in which a methyl group corresponding to $R^1$ has been replaced by a hydrogen atom.

The structural unit (I) is derived from a compound represented by formula (I') (which is sometimes referred to as "compound (I')"):

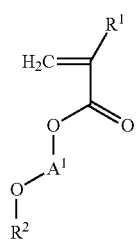
(I')

in which $R^1$, $R^2$ and $A^1$ are as defined above.

Examples of the compound (I') include the following ones.

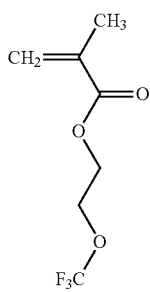
(I'-4)

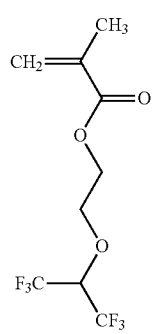
(I'-1)

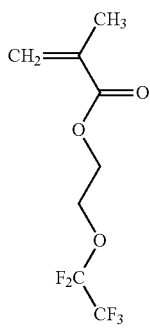
(I'-5)

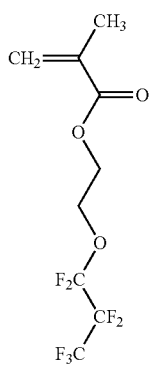 (I'-6)
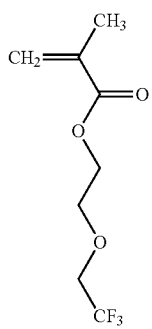 (I'-7)
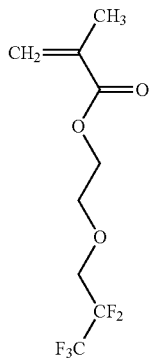 (I'-8)
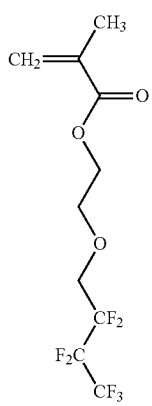 (I'-9)
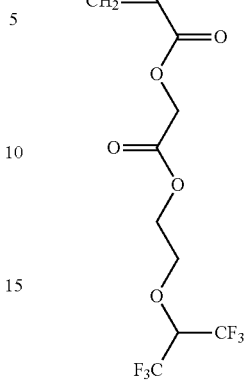 (I'-10)
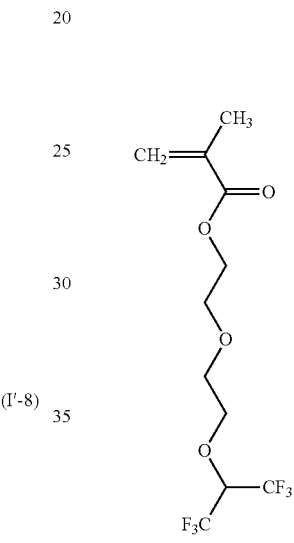 (I'-11)
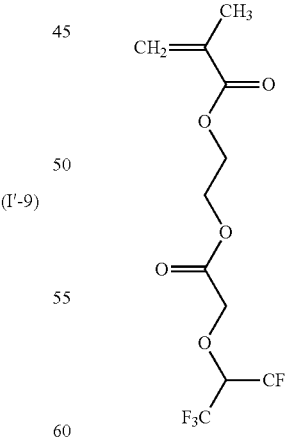 (I'-12)
Examples of the compounds (I') include compounds represented by the above formulae in which a methyl group corresponding to $R^1$ has been replaced by a hydrogen atom.
The compound (I') is preferably a compound represented by formula (Ia) below.

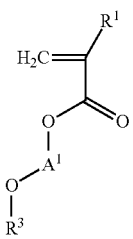
(Ia)

wherein $R^1$ represents a fluorine atom, a hydrogen atom, or a $C_1$ to $C_6$ alkyl group in which a hydrogen atom can be replaced by a fluorine atom, $R^3$ represents —CH($R^{f1}$)($R^{f2}$), $R^{f1}$ and $R^{f2}$ each independently represent a $C_1$ to $C_6$ perfluoroalkyl group, $A^1$ represents a $C_2$ to $C_6$ alkanediyl group or *-$A^2$-$X^1$-($A^3$-$X^2$)$_a$-$A^4$-,

* represents a binding site to an oxygen atom in —O—CO—, $A^2$, $A^3$ and $A^4$ each independently represent a $C_1$ to $C_6$ alkanediyl group, $X^1$ and $X^2$ each independently represent —O—, —CO—O— or —O—CO—, and "a" represents 0 or 1.

<Method for Producing the Compound (I')>

The compound (I') for example, can be obtained by reacting a compound represented by formula (Ia-a) with a compound represented by formula (Ia-b) in presence of a basic catalyst in a solvent:

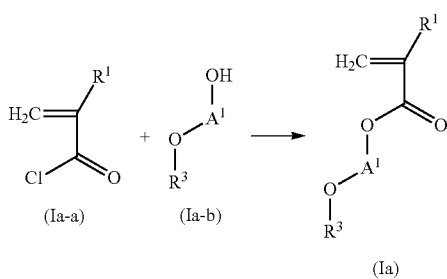

in which $R^1$, $R^3$ and $A^1$ are as defined above.

Preferred examples of the solvent include tetrahydrofuran and n-heptane.

Preferred examples of the basic catalyst include N-methylpyrrolidine, trimethylamine, pyridine and dimethylaminopyridine.

Examples of the compound represented by the formula (Ia-a) include a compound represented by formula below which is available on the market.

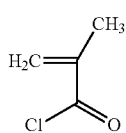

The compound (Ia-b) can be obtained by reacting a compound represented by formula (Ia-c) with a compound represented by formula (Ia-d) in presence of a basic catalyst in a solvent:

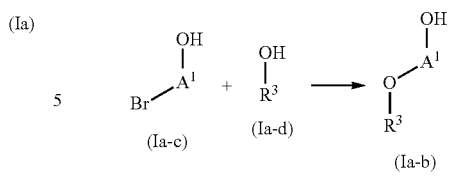

in which $R^3$ and $A^1$ are as defined above.

Preferred examples of the solvent include methyl ethyl ketone.

Preferred examples of the catalyst include potassium hydroxide.

Examples of the compound represented by the formula (Ia-c) include compound represented by formula below which is available on the market.

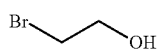

Examples of the compound represented by the formula (Ia-d) include compound represented by formula below which is available on the market.

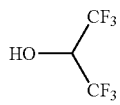

The resin (A2) may include one kind of the structural units (1), or two or more kinds of them.

The resin (A2) preferably has the structural unit derived from the compound (Ia) among the structural unit (1).

The proportion of the structural unit (I) is preferably 10 to 100% by mole, more preferably 50 to 100% by mole, still more preferably 80 to 100% by mole, particularly preferably 100% by mole with respect to the total structural units (100% by mole) of the resin (A2).

The resin (A2) may further have the structural unit (a4), the structural unit (a5), the structural unit (a1), the structural unit (s) and the structural unit (t) as well as the structural unit derived from the known monomer in the art.

The resin (A2) is preferably a resin that further has the structural unit (a4) and/or the structural unit (a5), while it is preferably a resin that has no structural unit (a1).

When the resin (A2) further has the structural unit (a4), the proportion of the structural unit (a4) is preferably 10 to 90% by mole, more preferably 10 to 80% by mole, still more preferably 10 to 70% by mole, still more preferably 10 to 50% by mole, particularly preferably 10 to 25% by mole with respect to the total structural units (100% by mole) of the resin (A2).

When the resin (A2) further has the structural unit (a5), the proportion of the structural unit (a4) is preferably 10 to 90% by mole, more preferably 10 to 80% by mole, still more preferably 10 to 70% by mole, still more preferably 10 to 50% by mole, particularly preferably 10 to 25% by mole with respect to the total structural units (100% by mole) of the resin (A2).

The resin (A2) can be produced by a known polymerization method, for example, radical polymerization method, using one or more species of monomers inducing the structural units as described above. The proportion of the structural unit in the resin (A2) can be adjusted by changing the amount of a monomer used in polymerization.

The weight average molecular weight of the resin (A2) is preferably 8,000 or more (more preferably 10,000 or more), and 80,000 or less (more preferably 60,000 or less). The method of measuring of the weight average molecular weight of the resin (A2) is the same as the resin (A1).

In the resist composition, the proportion of the resin (A2) is preferably 0.5 to 60 parts by mass, more preferably 1 to 60 parts by mass, still more preferably 1 to 50 parts by mass, still more preferably 1 to 40 parts by mass, still more preferably 1 to 30 parts by mass, still more preferably 2 to 25 parts by mass, still more preferably 2 to 10 parts by mass, particularly preferably 2 to 8 parts by mass with respect to the resin (A1) (100 parts by mass).

The total proportion of the resin (A1) and the resin (A2) is preferably 80% by mass to 99% by mass, more preferably 90% by mass to 99% by mass, with respect to the total amount of solid components of the resist composition.

The proportion of the solid components in the resist composition and that of the resins in the solid components can be measured with a known analytical method such as liquid chromatography and gas chromatography.

<Resin (X)>

The resist composition of the disclosure may further contain a resin (X) other than the resin (A1) and the resin (A2). Examples of the resin (X) include a resin consisting of the structural unit (s) such as the structural unit (a2) and the structural unit (a3), and a resin including the structural unit (a4).

The resin (X) is preferably a resin that has the structural unit (a4). When the resin (X) has the structural unit (a4), the proportion thereof is preferably 40% by mole or more, more preferably 45% by mole or more, and still more preferably 50% by mole or more with respect to the total structural unit of the resin (X). The resin (X) may further have the structural unit (a2), the structural unit (a3) and the structural unit derived from the known monomer in the art.

The resin (X) can be produced by a known polymerization method, for example, radical polymerization method, using one or more species of monomers inducing the structural units as described above. The proportion of the structural unit in the resin (X) can be adjusted by changing the amount of a monomer used in polymerization.

The weight average molecular weight of the resin (X) is preferably 8,000 or more (more preferably 10,000 or more), and 80,000 or less (more preferably 60,000 or less). The method of measuring of the weight average molecular weight of the resin (X) is the same as the resin (A1).

When the resist composition includes the resin (X), the proportion thereof is preferably 1 to 60 parts by mass, more preferably 1 to 50 parts by mass, and still more preferably 1 to 40 parts by mass, in particular preferably 2 to 30 parts by mass, with respect to total amount of the resin (A1) and the resin (A2) (100 parts by mass).

The total proportion of the resin (A1), the resin (A2) and the resin (X) is preferably 80% by mass to 99% by mass, more preferably 90% by mass to 99% by mass, with respect to the total amount of solid components of the resist composition.

<Acid Generator (B)>

The acid generator (B) may be an ionic acid generator or a non-ionic acid generator. The acid generator (B) may be used any an ionic acid generator and a non-ionic acid generator. Examples of the nonionic compounds for the acid generator include organic halogenated compounds; sulfonate esters, e.g. 2-nitrobenzylester, aromatic sulfonates, oximesulfonate, N-sulfonyloxyimide, sulfonyloxyketone, and diazonaphtoquione 4-sulfonate; sulfones, e.g., disulfone, ketosulfone, and sulfonium diazomethane. The ionic compounds for the acid generator include onium salts having an onium cation, e.g., diazonium salts, phosphonium salts, sulfonium salts and iodonium salts. Examples of the anions of onium salt include a sulfonic acid anion, a sulfonylimide anion, sulfonylmethide anion.

As the acid generator, the compounds giving an acid by radiation can be used, which are mentioned in JPS63-26653A1, JPS55-164824A1, JPS62-69263A1, JPS63-146038A1, JPS63-163452A1, JPS62-153853A1, JPS63-146029A1, U.S. Pat. No. 3,779,778B1, U.S. Pat. No. 3,849,137B1, DE3914407 and EP126,712A1. The acid generator for the photoresist composition can be produced by the method described in the above-mentioned documents.

In the resist composition of the disclosure, the acid generator (B) may be used as a single salt or as a combination of two or more of salts.

The acid generator (B) is preferably a fluorine-containing compound, more preferably a salt represented by formula (B1) (which is sometimes referred to as "acid generator (B1)"):

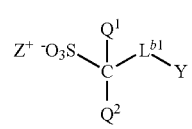

(B1)

wherein $Q^1$ and $Q^2$ each respectively represent a fluorine atom or a $C_1$ to $C_6$ perfluoroalkyl group, $L^{b1}$ represents a $C_1$ to $C_{24}$ divalent saturated hydrocarbon group where a methylene group may be replaced by an oxygen atom or a carbonyl group and a hydrogen atom may be replaced by a hydroxyl group or fluorine atom, and Y represents an optionally substituted methyl group or an optionally substituted $C_3$ to $C_{18}$ alicyclic hydrocarbon group, and a methylene group contained in the alicyclic hydrocarbon group may be replaced by an oxygen atom, a carbonyl group or a sulfonyl group, and $Z^+$ represents an organic cation.

Examples of the perfluoroalkyl group of $Q^1$ and $Q^2$ include trifluoromethyl, perfluoroethyl, perfluoropropyl, perfluoro-isopropyl, perfluorobutyl, perfluoro-sec-butyl, perfluoro-tert-butyl, perfluoropentyl and perfluorohexyl groups.

$Q^1$ and $Q^2$ independently are preferably a trifluoromethyl group or a fluorine atom, and both of $Q^1$ and $Q^2$ are more preferably a fluorine atom.

Examples of the divalent saturated hydrocarbon group for $L^{b1}$ include any of a chain or a branched alkanediyl group, a divalent saturated monocyclic- or a polycyclic alicyclic hydrocarbon group, and a combination thereof.

Specific examples of the chain alkanediyl group include methylene, ethylene, propane-1,3-diyl, propane-1,2-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, heptadecane-1,17-diyl groups.

Specific examples of the branched chain alkanediyl group include ethane-1,1-diyl, propane-1,1-diyl, propane-1,2-diyl, propane-2,2-diyl, pentane-1,4-diyl, pentane-2,4-diyl, 2-methylpropane-1,3-diyl, 2-methylpropane-1,2-diyl and 2-methylbutane-1,4-diyl groups.

Specific examples of the saturated monocyclic alicyclic hydrocarbon group include a cycloalkanediyl group such as cyclobutan-1,3-diyl, cyclopentan-1,3-diyl, cyclohexane-1,4-diyl and cyclooctan-1,5-diyl groups.

Specific examples of the saturated polycyclic alicyclic hydrocarbon group include norbornane-1,4-diyl, norbornane-2,5-diyl, adamantane-1,5-diyl and adamantane-2,6-diyl groups.

Examples of the divalent saturated hydrocarbon group for $L^{b1}$ in which a methylene group has been replaced by oxygen atom or a carbonyl group include the following groups represented by formula (b1-1) to formula (b1-3):

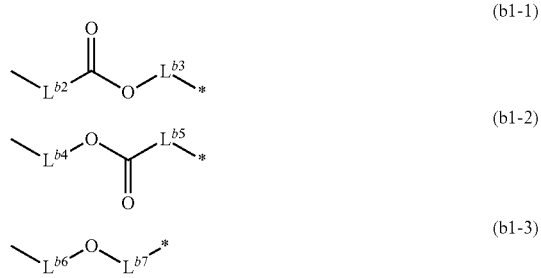

wherein $L^{b2}$ represents a single bond or a $C_1$ to $C_{22}$ divalent saturated hydrocarbon group where a hydrogen atom may be replaced by a fluorine atom;

$L^{b3}$ represents a single bond or a $C_1$ to $C_{22}$ divalent saturated hydrocarbon group where a hydrogen atom may be replaced by a fluorine atom or a hydroxy group, and a methylene group may be replaced by an oxygen atom or a carbonyl group;

provided that the total carbon number contained in the group of $L^{b2}$ and $L^{b3}$ is 22 or less;

$L^{b4}$ represents a single bond or a $C_1$ to $C_{22}$ divalent saturated hydrocarbon group where a hydrogen atom may be replaced by a fluorine atom;

$L^{b5}$ represents a single bond or a $C_1$ to $C_{22}$ divalent saturated hydrocarbon group where a hydrogen atom may be replaced by a fluorine atom or a hydroxy group, and a methylene group may be replaced by an oxygen atom or a carbonyl group;

provided that the total carbon number contained in the group of $L^{b4}$ and $L^{b5}$ is 22 or less;

$L^{b6}$ represents a single bond or a $C_1$ to $C_{23}$ divalent saturated hydrocarbon group where a hydrogen atom may be replaced by a fluorine atom or a hydroxy group;

$L^{b7}$ represents a single bond or a $C_1$ to $C_{23}$ divalent saturated hydrocarbon group where a hydrogen atom may be replaced by a fluorine atom or a hydroxy group, and a methylene group may be replaced by an oxygen atom or a carbonyl group;

provided that the total carbon number contained in the group of $L^{b6}$ and $L^{b7}$ is 23 or less, and

* represents a binding site to Y.

In formula (b1-1) to formula (b1-3), when a methylene group has been replaced by an oxygen atom or a carbonyl group, the carbon number of the saturated hydrocarbon group corresponds to the number of the carbon atom before replacement.

Examples of the divalent saturated hydrocarbon group are the same examples as the divalent saturated hydrocarbon group of $L^{b1}$.

$L^{b2}$ is preferably a single bond.

$L^{b3}$ is preferably a $C_1$ to $C_4$ divalent saturated hydrocarbon group.

$L^{b4}$ is preferably a $C_1$ to $C_8$ divalent saturated hydrocarbon group where a hydrogen atom may be replaced by a fluorine atom.

$L^{b5}$ is preferably a single bond or a $C_1$ to $C_8$ divalent saturated hydrocarbon group.

$L^{b6}$ is preferably a single bond or a $C_1$ to $C_4$ divalent saturated hydrocarbon group where a hydrogen atom may be replaced by a fluorine atom.

$L^{b7}$ is preferably a single bond or a $C_1$ to $C_{18}$ divalent saturated hydrocarbon group where a hydrogen atom may be replaced by a fluorine atom or a hydroxy group, and where a methylene group may be replaced by an oxygen atom or a carbonyl group.

Among these, the group represented by the formula (b1-1) or the formula (b1-3) is preferred.

Examples of the divalent group represented by the formula (b1-1) include the following groups represented by formula (b1-4) to formula (b1-8):

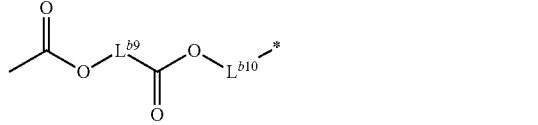

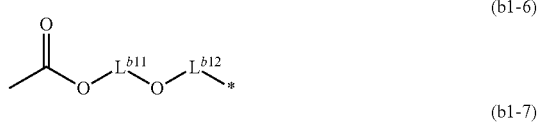

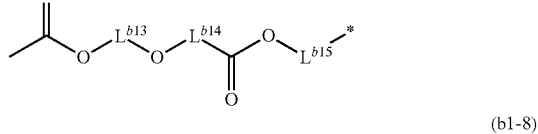

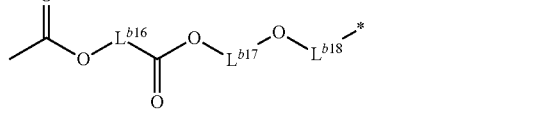

wherein $L^{b8}$ represents a single bond or a $C_1$ to $C_{22}$ divalent saturated hydrocarbon group where a hydrogen atom may be replaced by a fluorine atom or a hydroxy group;

$L^{b9}$ represents a $C_1$ to $C_{20}$ divalent saturated hydrocarbon group;

$L^{b10}$ represents a single bond or a $C_1$ to $C_{19}$ divalent saturated hydrocarbon group where a hydrogen atom may be replaced by a fluorine atom or a hydroxy group;

provided that the total carbon number contained in the group of $L^{b9}$ and $L^{b10}$ is 20 or less;

$L^{b11}$ represents a $C_1$ to $C_{21}$ divalent saturated hydrocarbon group;

$L^{b12}$ represents a single bond or a $C_1$ to $C_{20}$ divalent saturated hydrocarbon group where a hydrogen atom may be replaced by a fluorine atom or a hydroxy group; provided that the total carbon number contained in the group of $L^{b11}$ and $L^{b12}$ is 21 or less;

$L^{b13}$ represents a $C_1$ to $C_{19}$ divalent saturated hydrocarbon group;

$L^{b14}$ represents a single bond or a $C_1$ to $C_{18}$ divalent saturated hydrocarbon group;

$L^{b15}$ represents a single bond or a $C_1$ to $C_{18}$ divalent saturated hydrocarbon group where a hydrogen atom may be replaced by a fluorine atom or a hydroxy group;

provided that the total carbon number contained in the group of $L^{b13}$, $L^{b14}$ and $L^{b15}$ is 19 or less;

$L^{b16}$ represents a $C_1$ to $C_{18}$ divalent saturated hydrocarbon group;

$L^{b17}$ represents a $C_1$ to $C_{18}$ divalent saturated hydrocarbon group;

$L^{b18}$ represents a single bond or a $C_1$ to $C_{17}$ divalent saturated hydrocarbon group where a hydrogen atom may be replaced by a fluorine atom or a hydroxy group; provided that the total carbon number contained in the group of $L^{b16}$, $L^{b17}$ and $L^{b18}$ is 19 or less.

$L^{b8}$ is preferably a $C_1$ to $C_4$ divalent saturated hydrocarbon group.

$L^{b9}$ is preferably a $C_1$ to $C_8$ divalent saturated hydrocarbon group.

$L^{b10}$ is preferably a single bond or a $C_1$ to $C_{19}$ divalent saturated hydrocarbon group, and more preferably a single bond or a $C_1$ to $C_8$ divalent saturated hydrocarbon group.

$L^{b11}$ is preferably a $C_1$ to $C_8$ divalent saturated hydrocarbon group.

$L^{b12}$ is preferably a single bond or a $C_1$ to $C_8$ divalent saturated hydrocarbon group.

$L^{b13}$ is preferably a $C_1$ to $C_{12}$ divalent saturated hydrocarbon group.

$L^{b14}$ is preferably a single bond or a $C_1$ to $C_6$ divalent saturated hydrocarbon group.

$L^{b15}$ is preferably a single bond or a $C_1$ to $C_{18}$ divalent saturated hydrocarbon group, and more preferably a single bond or a $C_1$ to $C_8$ divalent saturated hydrocarbon group.

$L^{b16}$ is preferably a $C_1$ to $C_{12}$ divalent saturated hydrocarbon group.

$L^{b17}$ is preferably a $C_1$ to $C_6$ divalent saturated hydrocarbon group.

$L^{b18}$ is preferably a single bond or a $C_1$ to $C_{17}$ divalent saturated hydrocarbon group, and more preferably a single bond or a $C_1$ to $C_4$ divalent saturated hydrocarbon group.

Examples of the divalent group represented by the formula (b1-3) include the following groups represented by formula (b1-9) to formula (b1-11):

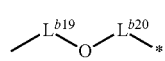

(b1-9)

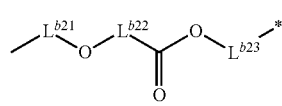

(b1-10)

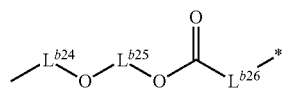

(b1-11)

wherein $L^{b19}$ represents a single bond or a $C_1$ to $C_{23}$ divalent saturated hydrocarbon group where a hydrogen atom may be replaced by a fluorine atom;

$L^{b20}$ represent a single bond or a $C_1$ to $C_{23}$ divalent saturated hydrocarbon group where a hydrogen atom may be replaced by a fluorine atom, a hydroxy group or an acyloxy group, and a methylene group contained in an acyloxy group may be replaced by an oxygen atom or a carbonyl group, and a hydrogen atom contained in an acyloxy group may be replaced by a hydroxy group, provided that the total carbon number contained in the group of $L^{b19}$ and $L^{b20}$ is 23 or less;

$L^{b21}$ represents a single bond or a $C_1$ to $C_{21}$ divalent saturated hydrocarbon group where a hydrogen atom may be replaced by a fluorine atom;

$L^{b22}$ represents a single bond or a $C_1$ to $C_{21}$ divalent saturated hydrocarbon group;

$L^{b23}$ represents a single bond or a $C_1$ to $C_{21}$ divalent saturated hydrocarbon group where a hydrogen atom may be replaced by a fluorine atom, a hydroxy group or an acyloxy group, and a methylene group contained in an acyloxy group may be replaced by an oxygen atom or a carbonyl group, and a hydrogen atom contained in an acyloxy group may be replaced by a hydroxy group, provided that the total carbon number contained in the group of $L^{b21}$, $L^{b22}$ and $L^{b23}$ is 21 or less;

$L^{b24}$ represents a single bond or a $C_1$ to $C_{20}$ divalent saturated hydrocarbon group where a hydrogen atom may be replaced by a fluorine atom;

$L^{b25}$ represents a single bond or a $C_1$ to $C_{21}$ divalent saturated hydrocarbon group;

$L^{b26}$ represents a single bond or a $C_1$ to $C_{20}$ divalent saturated hydrocarbon group where a hydrogen atom may be replaced by a fluorine atom, a hydroxy group or an acyloxy group, and a methylene group contained in an acyloxy group may be replaced by an oxygen atom or a carbonyl group, and a hydrogen atom contained in an acyloxy group may be replaced by a hydroxy group, provided that the total carbon number contained in the group of $L^{b24}$, $L^{b25}$ and $L^{b26}$ is 21 or less.

In formula (b1-9) to formula (b1-11), when a hydrogen atom has been replaced by an acyloxy group, the carbon number of the saturated hydrocarbon group corresponds to the number of the carbon atom, CO and O in addition to the carbon number of the saturated hydrocarbon group.

Examples of the acyloxy group include acetyloxy, propionyloxy, butyryloxy, cyclohexyl carbonyloxy and adamantyl carbonyloxy groups.

Examples of the acyloxy group having a substituent include oxoadamantyl carbonyloxy, hydroxyadamantyl carbonyloxy, oxocyclohexyl carbonyloxy and hydroxycyclohexyl carbonyloxy groups.

Examples of the group represented by the formula (b1-4) include the following ones.

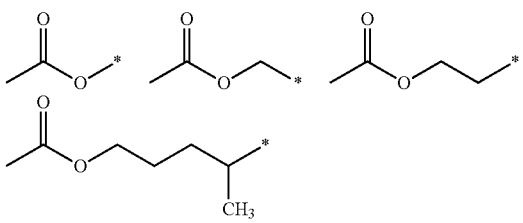

Examples of the group represented by the formula (b1-5) include the following ones.
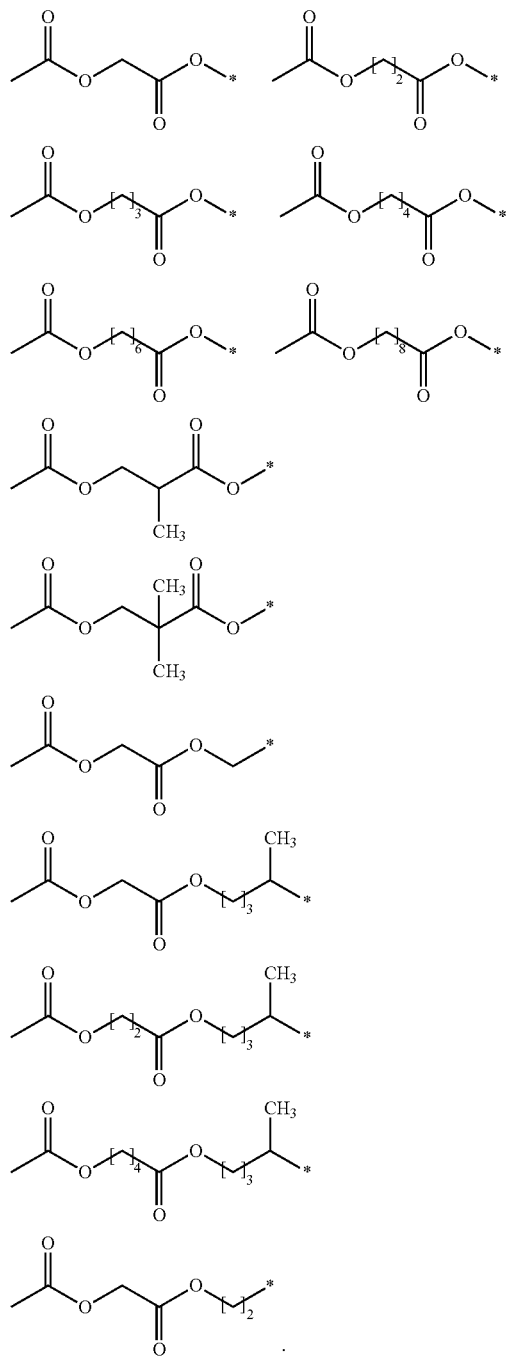
Examples of the group represented by the formula (b1-6) include the following ones.
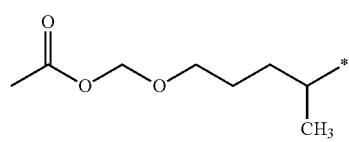
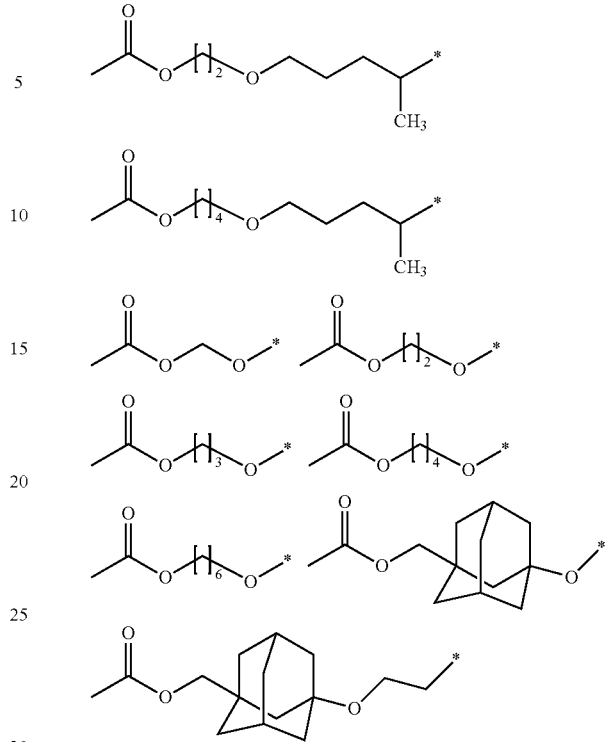
Examples of the group represented by the formula (b1-7) include the following ones.
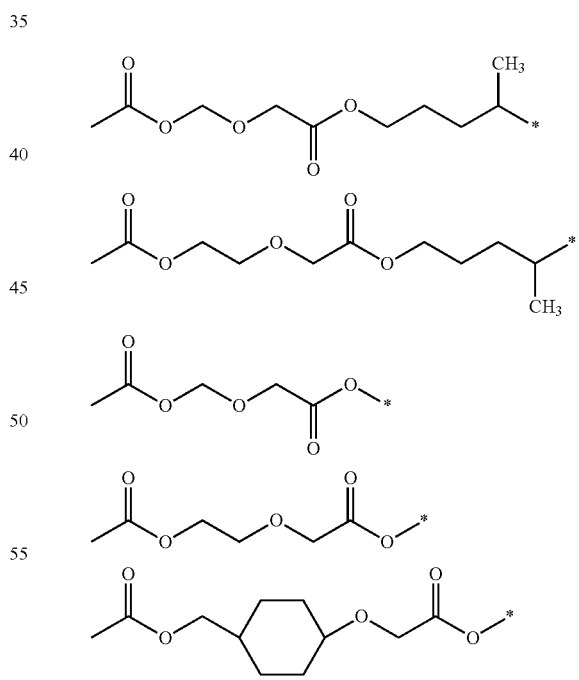
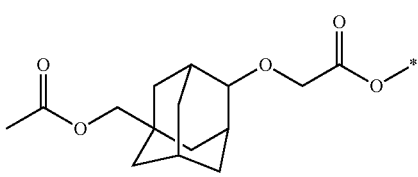

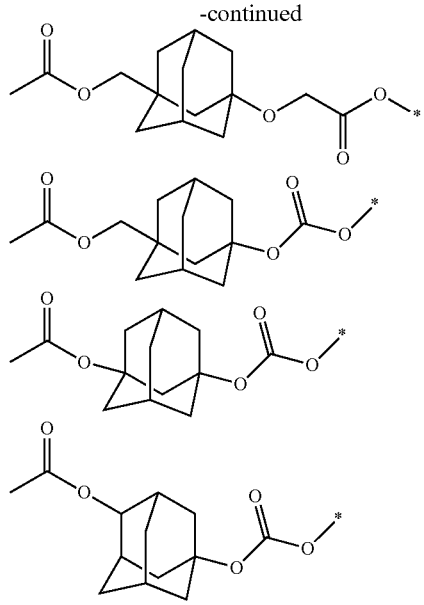
Examples of the group represented by the formula (b1-8) include the following ones.
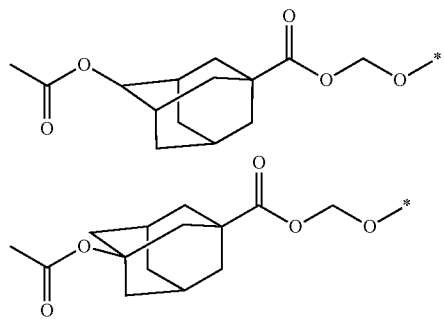
Examples of the group represented by the formula (b1-2) include the following ones.
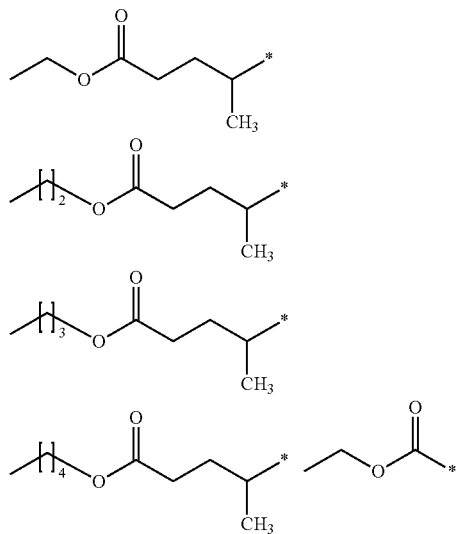
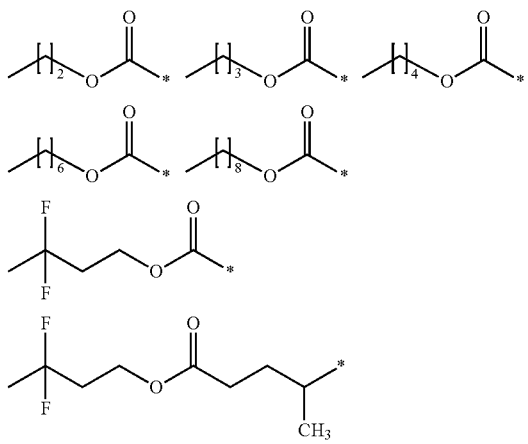
Examples of the group represented by the formula (b1-9) include the following ones.
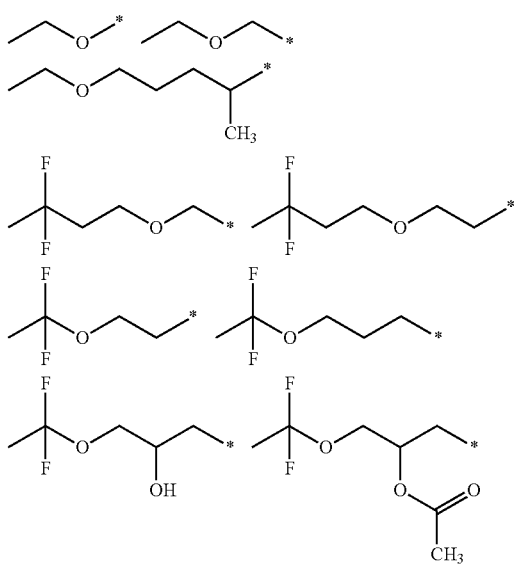
Examples of the group represented by the formula (b1-10) include the following ones.
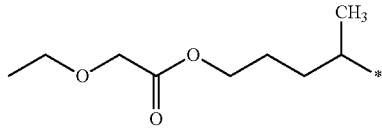

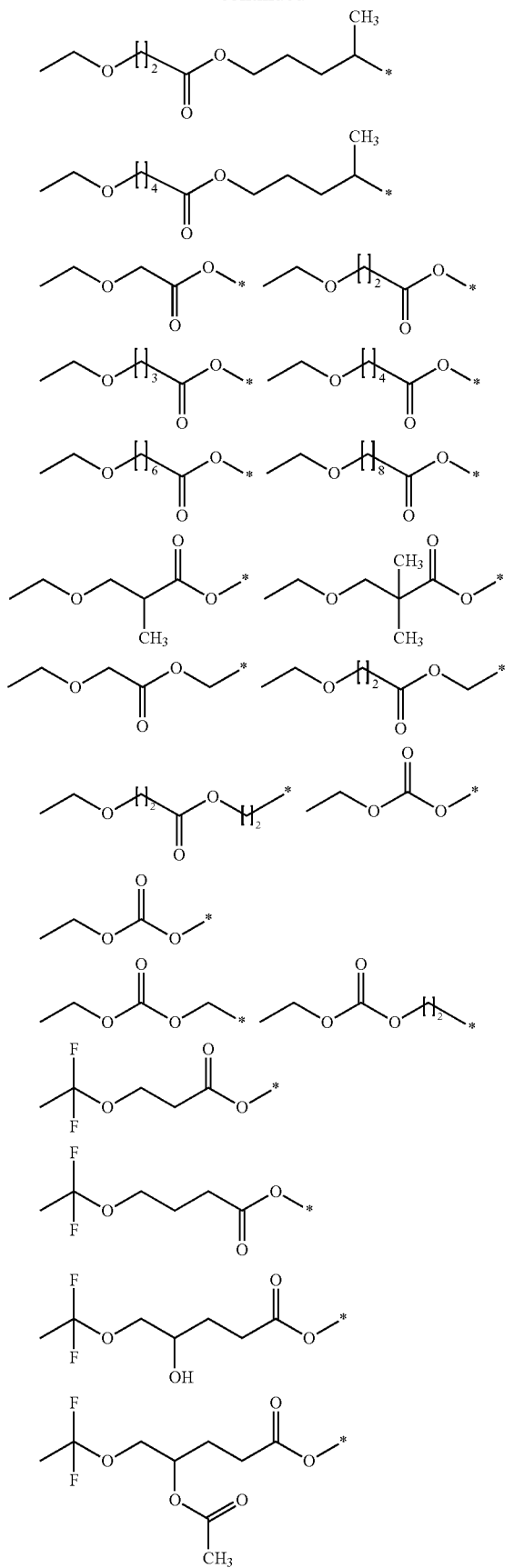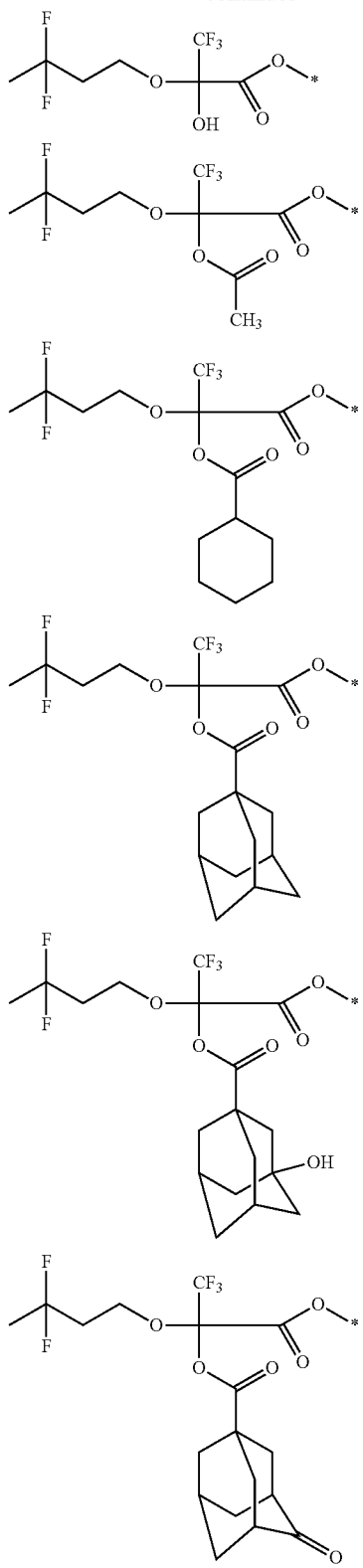
Examples of the group represented by the formula (b1-11) include the following

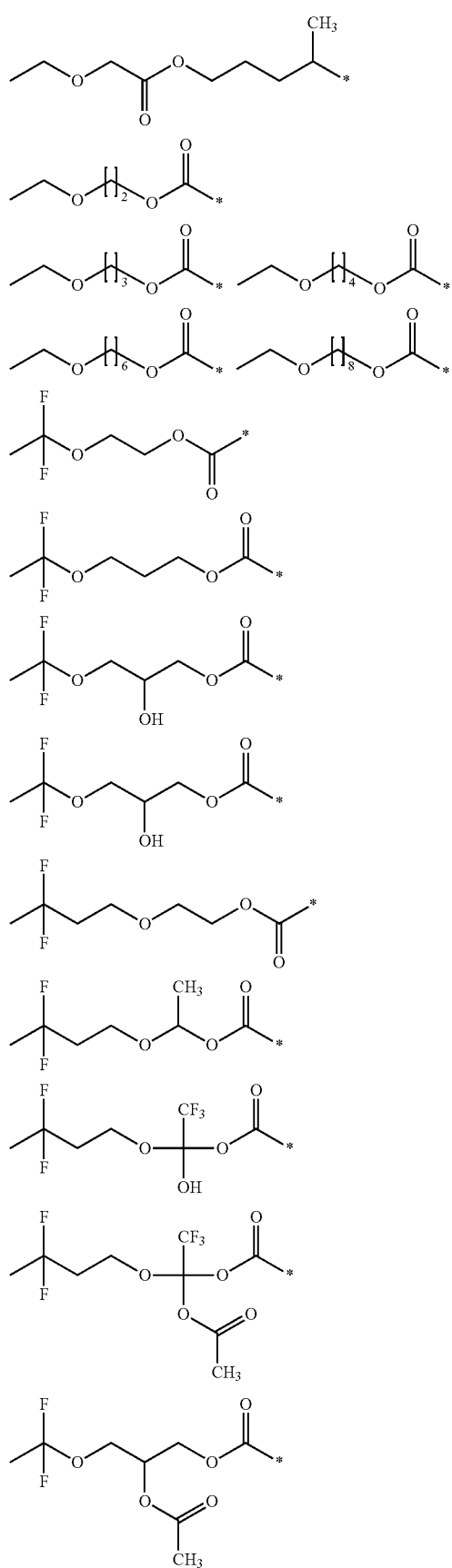
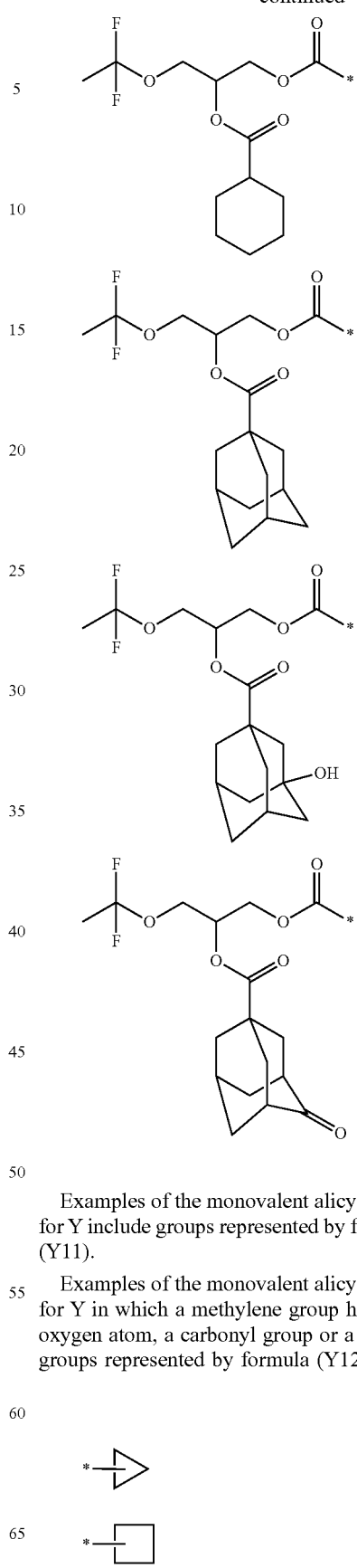
Examples of the monovalent alicyclic hydrocarbon group for Y include groups represented by formula (Y1) to formula (Y11).
Examples of the monovalent alicyclic hydrocarbon group for Y in which a methylene group has been replaced by an oxygen atom, a carbonyl group or a sulfonyl group include groups represented by formula (Y12) to formula (Y27).
 (Y1)
 (Y2)

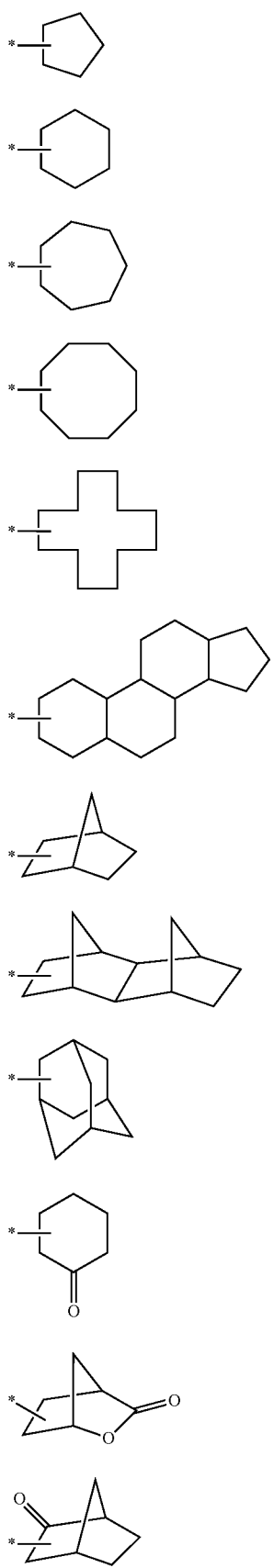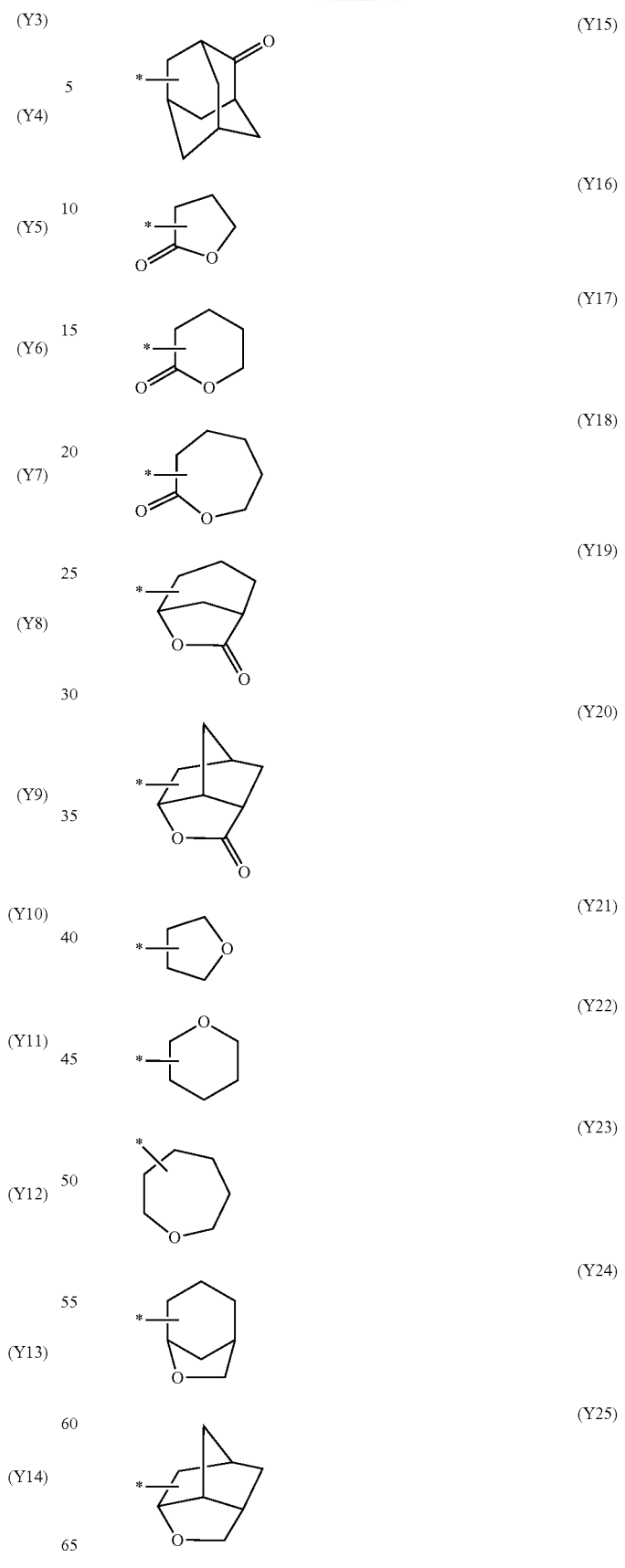

-continued

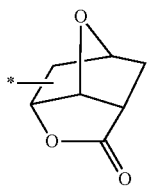
(Y26)

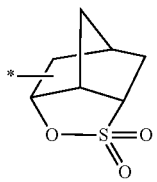
(Y27)

Among these, the alicyclic hydrocarbon group is preferably any one of groups represented by the formula (Y1) to the formula (Y20), more preferably any one of groups represented by the formula (Y11), (Y15), (Y16) or (Y20), and still more preferably group represented by the formula (Y11) or (Y15).

Examples of the substituent of methyl group for Y include a halogen atom, a hydroxyl group, a $C_3$ to $C_{16}$ monovalent alicyclic hydrocarbon group, a $C_6$ to $C_{18}$ monovalent aromatic hydrocarbon group, a glycidyloxy group and —$(CH_2)_{j2}$—O—CO—$R^{b1}$—, in which $R^{b1}$ represents an $C_1$ to $C_{16}$ alkyl group, a $C_3$ to $C_{16}$ monovalent alicyclic hydrocarbon group, or a $C_6$ to $C_{18}$ monovalent aromatic hydrocarbon group, and j2 represents an integer of 0 to 4.

Examples of the substituent of the alicyclic group for Y include a halogen atom, a hydroxyl group, a $C_1$ to $C_{12}$ alkyl group, a hydroxy group-containing $C_1$ to $C_{12}$ alkyl group, a $C_3$ to $C_{16}$ monovalent alicyclic hydrocarbon group, a $C_1$ to $C_{12}$ alkoxy group, a $C_6$ to $C_{18}$ monovalent aromatic hydrocarbon group, a $C_7$ to $C_{21}$ aralkyl group, a $C_2$ to $C_4$ acyl group, a glycidyloxy group and —$(CH_2)_{j2}$—O—CO—$R^{b1}$—, in which $R^{b1}$ represents an $C_1$ to $C_{16}$ alkyl group, a $C_3$ to $C_{16}$ monovalent alicyclic hydrocarbon group, or a $C_6$ to $C_{18}$ monovalent aromatic hydrocarbon group, and j2 represents an integer of 0 to 4.

Examples of the hydroxy group-containing alkyl group include hydroxymethyl and hydroxyethyl groups Examples of the alkoxyl group include methoxy, ethoxy, propoxy, butoxy, pentyloxy, hexyloxy, heptyloxy, octyloxy, decyloxy and dodecyloxy groups.

Examples of the monovalent aromatic hydrocarbon group include an aryl group such as phenyl, naphthyl, anthryl, p-methylphenyl, p-tert-butylphenyl, p-adamantylphenyl, tolyl, xylyl, cumenyl, mesityl, biphenyl, phenanthryl, 2,6-diethylphenyl and 2-methyl-6-ethylphenyl groups.

Examples of the aralkyl group include benzyl, phenethyl, phenylpropyl, naphthylmethyl and naphthylethyl groups.

Examples of the acyl group include acetyl, propionyl and butyryl groups.

Examples of the halogen atom include fluorine, chlorine, bromine and iodine atoms.

Examples of Y include the groups below. * represents a binding site to $L^{b1}$.

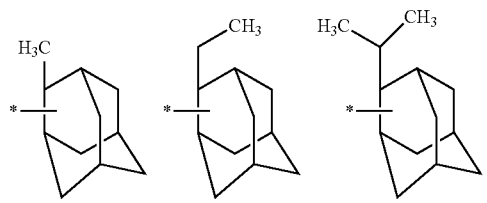
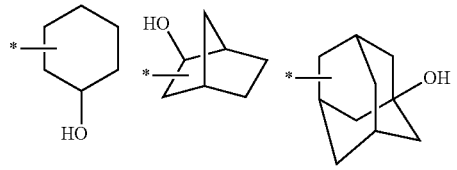
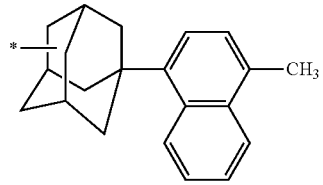
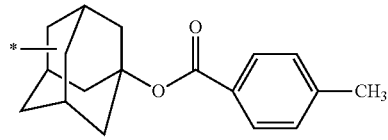
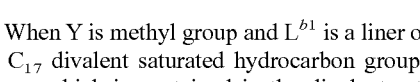

When Y is methyl group and $L^{b1}$ is a liner or branched $C_1$ to $C_{17}$ divalent saturated hydrocarbon group, a methylene group which is contained in the divalent saturated hydrocarbon group and is positioned at a binding site of Y preferably replaces with —O— or —CO—.

Y is preferably a $C_3$ to $C_{18}$ monovalent alicyclic hydrocarbon group which may have a substituent, more preferably an adamantyl group which may have a substituent and one or more methylene group contained in the adamantyl group may be replaced with an oxygen atom, a carbonyl group or a sulfonyl group, and still more preferably an adamantyl group, a hydroxyadamantyl group or an oxoadamantyl group.

The sulfonic acid anion in the salt represented by the formula (B1) is preferably an anions represented by formula (B1-A-1) to formula (B1-A-33), and more preferably an anions represented by formula (B1-A-1) to formula (B1-A-4), formula (B1-A-9), formula (B1-A-10), formula (B1-A-24) to formula (B1-A-33), below.

In formula (B1-A-1) to formula (B1-A-33), $R^{i2}$ to $R^{i7}$ each independently represent a $C_1$ to $C_4$ alkyl group, and preferably a methyl group or an ethyl group, $R^{i8}$ represent a $C_1$ to $C_{12}$ aliphatic hydrocarbon group, preferably a $C_1$ to $C_4$ alkyl group, a $C_5$ to $C_{12}$ monovalent alicyclic hydrocarbon group or a group formed by a combination thereof, more preferably a methyl group, an ethyl group, a cyclohexyl group or an adamantyl group. $L^{44}$ represents a single bond or a $C_1$ to $C_4$ alkanediyl group. $Q^1$ and $Q^2$ represent the same meaning as defined above.

Specific examples of the sulfonic acid anion in the salt represented by the formula (BI) include anions mentioned in JP2010-204646A1.

(B1-A-1) 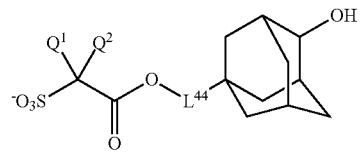
(B1-A-2) 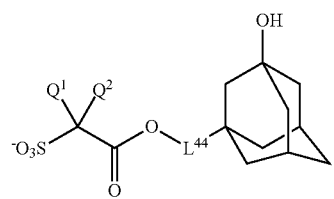
(B1-A-3) 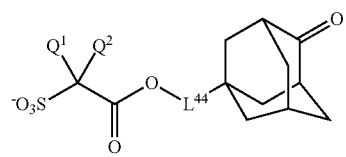
(B1-A-4) 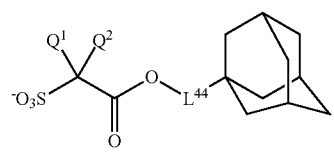
(B1-A-5) 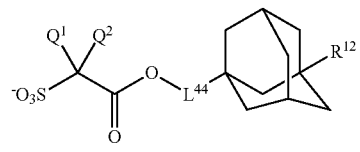
(B1-A-6) 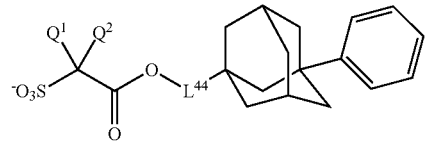
(B1-A-7) 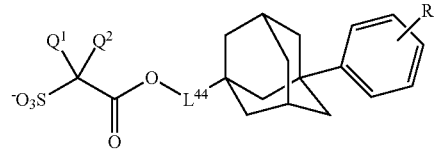
(B1-A-8) 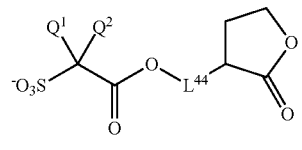
(B1-A-9) 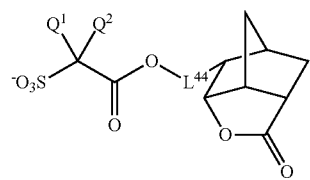
-continued
(B1-A-10) 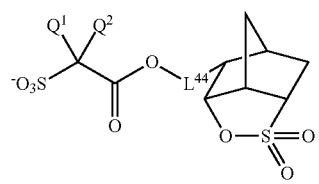
(B1-A-11) 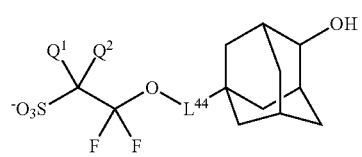
(B1-A-12) 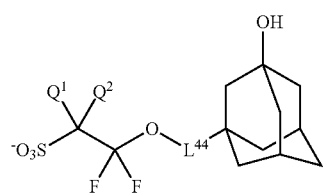
(B1-A-13) 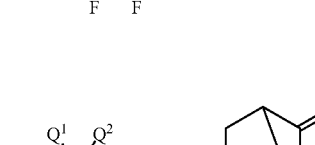
(B1-A-14) 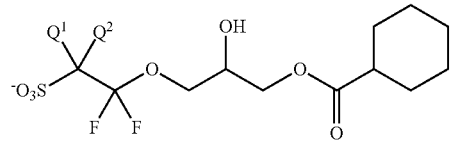
(B1-A-15) 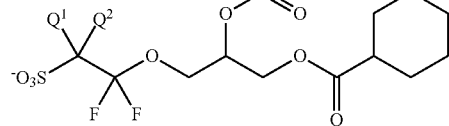
(B1-A-16) 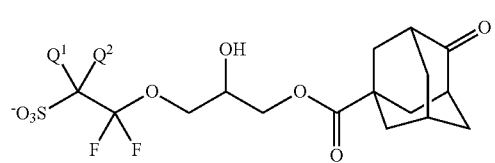

(B1-A-17)
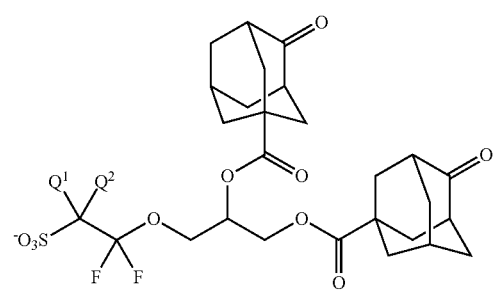
(B1-A-18)
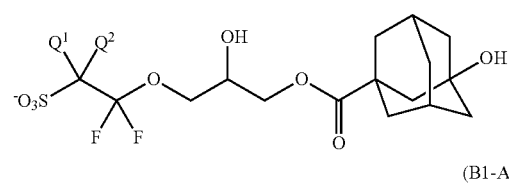
(B1-A-19)
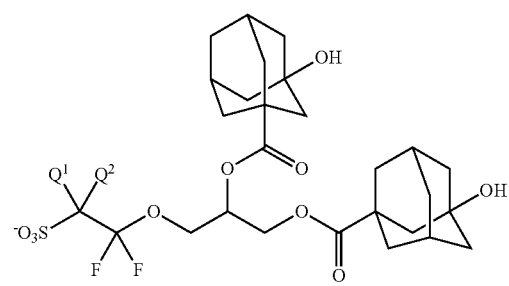
(B1-A-20)
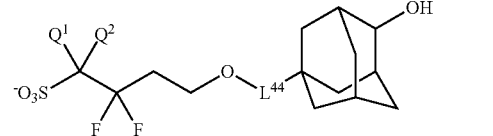
(B1-A-21)
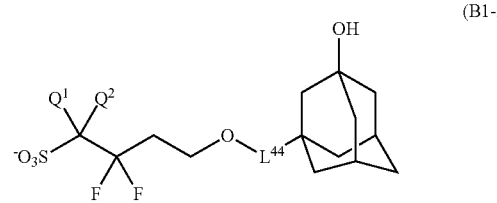
(B1-A-22)
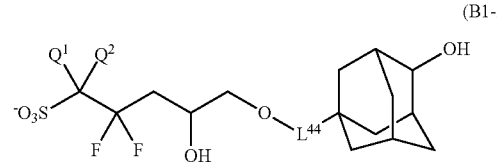
(B1-A-23)
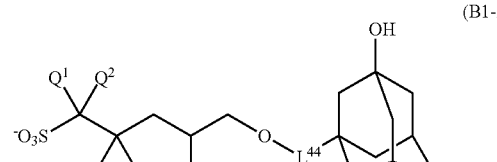
(B1-A-24)
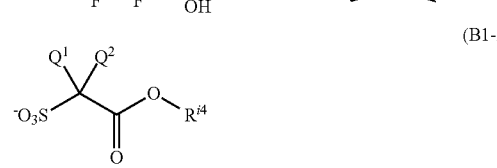
(B1-A-25)
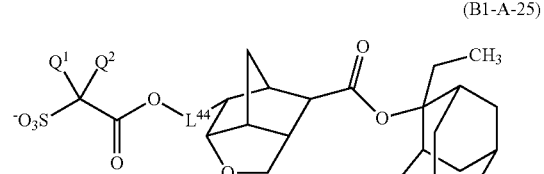
(B1-A-26)
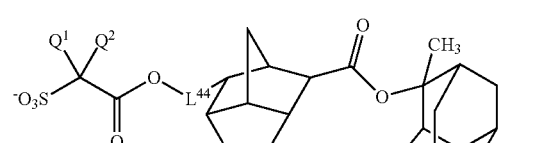
(B1-A-27)
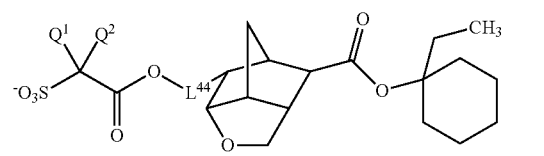
(B1-A-28)
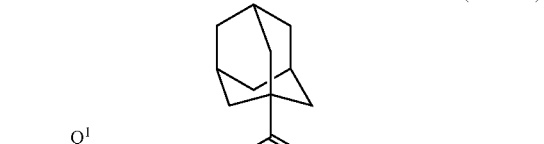
(B1-A-29)
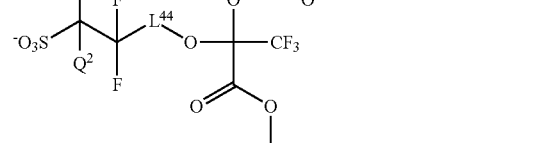
(B1-A-30)
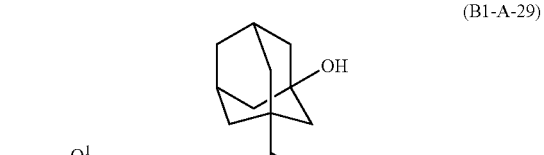
(B1-A-31)

(B1-A-32)
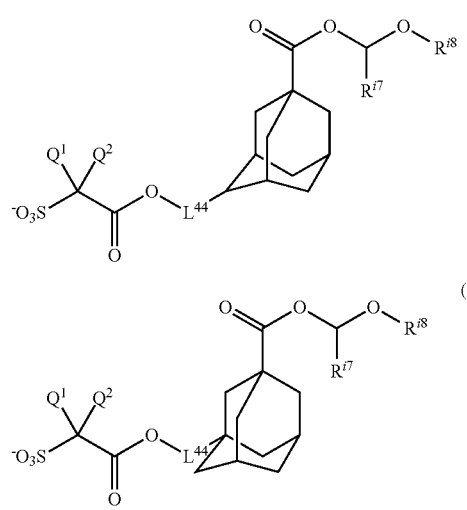
(B1-A-33)
Among these, preferred examples of the sulfonic acid anion for the salt represented by the formula (B1) include anions represented by formulae (B1a-1) to (B1a-15).
(B1a-1)
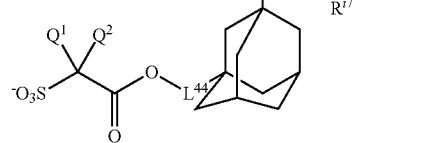
(B1a-2)
(B1a-3)
(B1a-4)
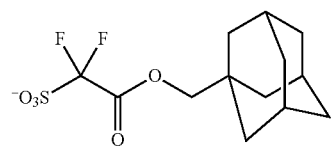
(B1a-5)
(B1a-6)
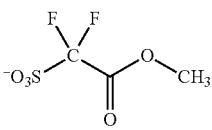
(B1a-7)
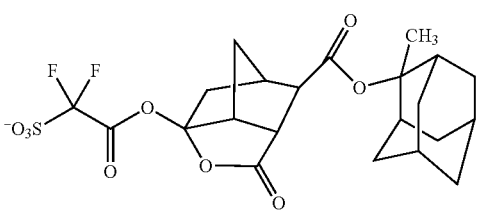
(B1a-8)
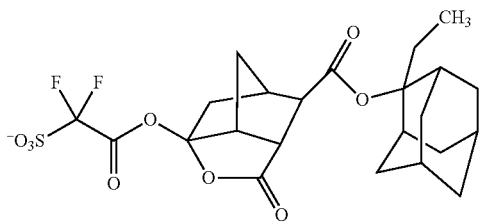
(B1a-8)
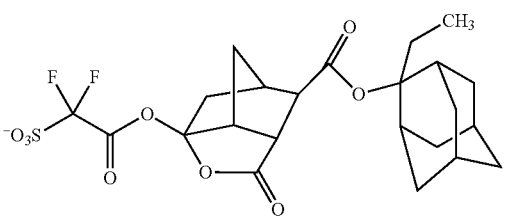
(B1a-9)
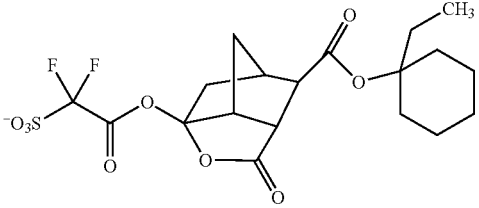
(B1a-10)
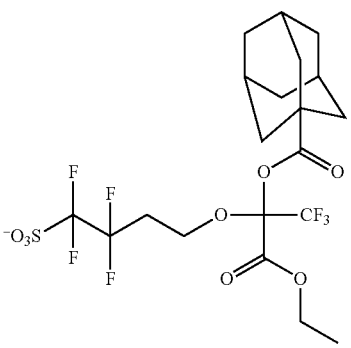

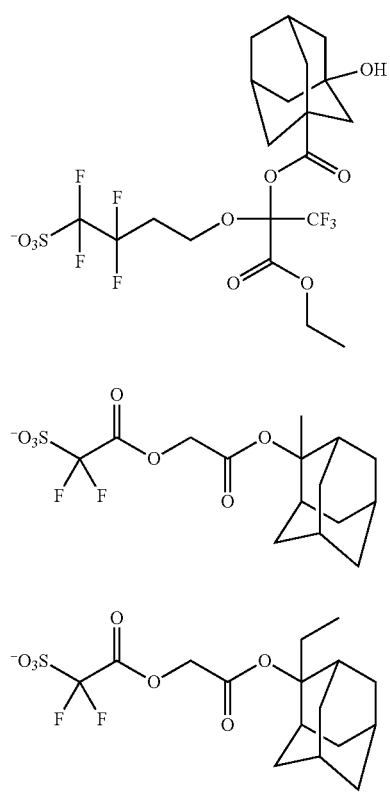

(Bla-11)

(Bla-12)

(Bla-13)

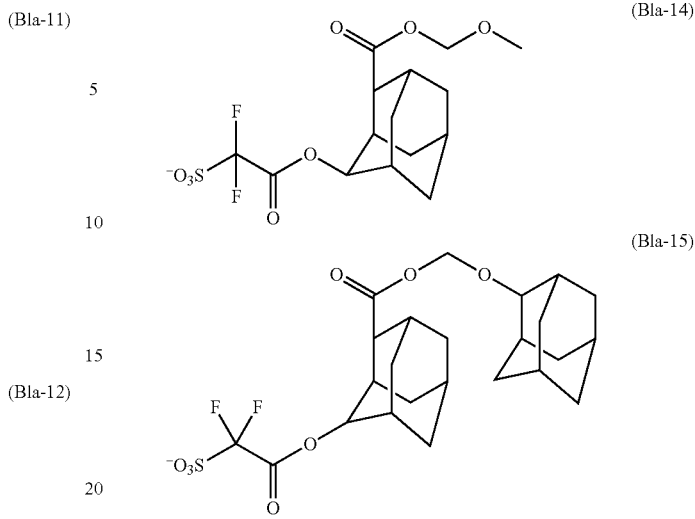

(Bla-14)

(Bla-15)

Preferred examples of the sulfonic acid anion include anions represented by the formulae (B1a-1) to (B1a-3) and (B1a-7) to (B1a-15).

Examples of the organic cation represented by Z include an organic onium cation such as an organic sulfonium cation, an organic iodonium cation, an organic ammonium cation, a benzothiazolium cation and an organic phosphonium cation.

An organic sulfonium cation and an organic iodonium cation are preferred, and an arylsulfonium cation is more preferred.

Z+ of the formula (B1) is preferably represented by any of formula (b2-1) to formula (b2-4):

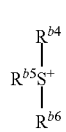

(b2-1)

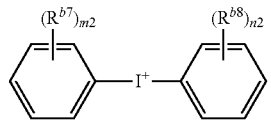

(b2-2)

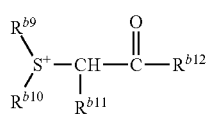

(b2-3)

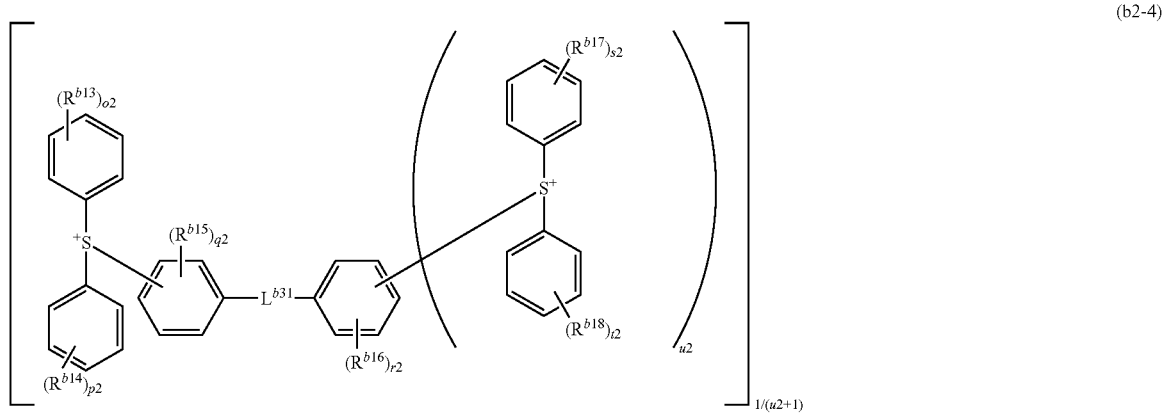

(b2-4)

wherein $R^{b4}$, $R^{b5}$ and $R^{b6}$ each independently represent a $C_1$ to $C_{30}$ aliphatic hydrocarbon group, a $C_3$ to $C_{36}$ alicyclic hydrocarbon group or a $C_6$ to $C_{36}$ aromatic hydrocarbon group, a hydrogen atom contained in the aliphatic hydrocarbon group may be replaced by a hydroxy group, a $C_1$ to $C_{12}$ alkoxy group, a $C_3$ to $C_{12}$ alicyclic hydrocarbon group or a $C_6$ to $C_{18}$ aromatic hydrocarbon group, a hydrogen atom contained in the alicyclic hydrocarbon group may be replaced by a halogen atom, a $C_1$ to $C_{18}$ aliphatic hydrocarbon group, a $C_2$ to $C_4$ acyl group or a glycidyloxy group, a hydrogen atom contained in the aromatic hydrocarbon group may be replaced by a halogen atom, a hydroxy group or a $C_1$ to $C_{12}$ alkoxy group, or $R^{b4}$ and $R^{b5}$ may be bonded together with a sulfur atom bonded thereto to form a sulfur-containing ring, a methylene group contained in the ring may be replaced by an oxygen atom, a —SO— or a carbonyl group;

$R^{b7}$ and $R^{b8}$ in each occurrence independently represent a hydroxy group, a $C_1$ to $C_{12}$ aliphatic hydrocarbon group or a $C_1$ to $C_{12}$ alkoxy group, m2 and n2 each independently represent an integer of 0 to 5;

$R^{b9}$ and $R^{b10}$ each independently represent a $C_1$ to $C_{36}$ aliphatic hydrocarbon group or a $C_3$ to $C_{36}$ alicyclic hydrocarbon group, or $R^{b9}$ and $R^{b10}$ may be bonded together with a sulfur atom bonded thereto to form a sulfur-containing ring, and a methylene group contained in the ring may be replaced by an oxygen atom, a —SO— or a carbonyl group;

$R^{b11}$ represents a hydrogen atom, a $C_1$ to $C_{36}$ aliphatic hydrocarbon group, a $C_3$ to $C_{36}$ alicyclic hydrocarbon group or a $C_6$ to $C_{18}$ aromatic hydrocarbon group;

$R^{b12}$ represents a $C_1$ to $C_{12}$ aliphatic hydrocarbon group, a $C_3$ to $C_{18}$ alicyclic hydrocarbon group and a $C_6$ to $C_{18}$ aromatic hydrocarbon group, a hydrogen atom contained in the aliphatic hydrocarbon group may be replaced by a $C_6$ to $C_{18}$ aromatic hydrocarbon group, and a hydrogen atom contained in the aromatic hydrocarbon group may be replaced by a $C_1$ to $C_{12}$ alkoxy group or a $C_1$ to $C_{12}$ alkyl carbonyloxy group;

$R^{b11}$ and $R^{b12}$ may be bonded together with —CH—CO— bonded thereto to form a ring, and a methylene group contained in the ring may be replaced by an oxygen atom, a —SO— or a carbonyl group;

$R^{b13}$, $R^{b14}$, $R^{b15}$, $R^{b16}$, $R^{b17}$ and $R^{b18}$ in each occurrence independently represent a hydroxy group, a $C_1$ to $C_{12}$ aliphatic hydrocarbon group or a $C_1$ to $C_{12}$ alkoxy group;

$L^{b31}$ represents —S— or —O—;

o2, p2, s2 and t2 independently represent an integer of 0 to 5;

q2 or r2 independently represent an integer of 0 to 4; and u2 represents an integer of 0 or 1.

Examples of the aliphatic group include an alkyl group such as methyl, ethyl, n-propyl, isopropyl, n-butyl, sec-butyl, tert-butyl, n-pentyl, n-hexyl, n-octyl and 2-ethylhexyl groups. Among these, the aliphatic hydrocarbon group for $R^{b9}$ to $R^{b12}$ is preferably a $C_1$ to $C_{12}$ aliphatic hydrocarbon group.

Examples of the alicyclic hydrocarbon group include monocyclic groups such as a cycloalkyl group, i.e., cyclopropyl, cyclobutyl, cyclopentyl, cyclohexyl, cycloheptyl, cyclooctyl, cyclodecyl groups; and polycyclic groups such as decahydronaphtyl, adamantyl and norbornyl groups as well as the following groups. * represents a binding site.

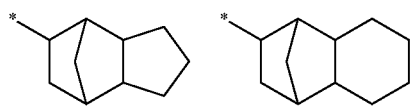

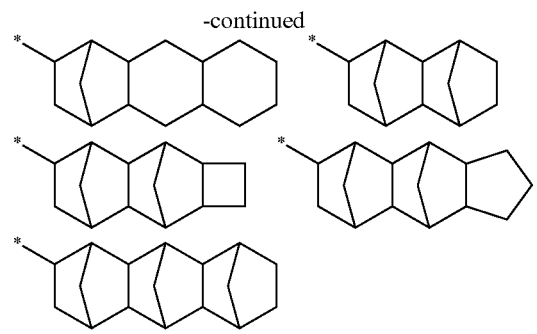

Among these, the alicyclic hydrocarbon group for $R^{b9}$ to $R^{b12}$ is preferably a $C_3$ to $C_{18}$ alicyclic hydrocarbon group, and more preferably a $C_4$ to $C_{12}$ alicyclic hydrocarbon group.

Examples of the alicyclic hydrocarbon group where a hydrogen atom may be replaced by an aliphatic hydrocarbon group include methylcyclohexyl, dimethylcyclohexyl, 2-alkyladamantane-2-yl, methylnorbornyl and isobornyl groups. In the alicyclic hydrocarbon group where a hydrogen atom may be replaced by an aliphatic hydrocarbon group, the total carbon number of the alicyclic hydrocarbon group and the aliphatic hydrocarbon group is preferably 20 or less.

Examples of the aromatic hydrocarbon group include an aryl group such as phenyl, tolyl, xylyl, cumenyl, mesityl, p-ethylphenyl, p-tert-butylphenyl, p-cyclohexylphenyl, p-adamantylphenyl, biphenyl, naphthyl, phenanthryl, 2,6-diethylphenyl and 2-methyl-6-ethylphenyl groups.

When the aromatic hydrocarbon includes an aliphatic hydrocarbon group or an alicyclic hydrocarbon group, a $C_1$ to $C_{18}$ aliphatic hydrocarbon group or a $C_3$ to $C_{18}$ alicyclic hydrocarbon group is preferred.

Examples of the aromatic hydrocarbon group where a hydrogen atom may be replaced by an alkoxy group include a p-methoxyphenyl group.

Examples of the aliphatic hydrocarbon group where a hydrogen atom may be replaced by an aromatic hydrocarbon group include an aralkyl group such as benzyl, phenethyl phenylpropyl, trityl, naphthylmethyl and naphthylethyl groups.

Examples of the alkoxy group include methoxy, ethoxy, propoxy, butoxy, pentyloxy, hexyloxy, heptyloxy, octyloxy, decyloxy and dodecyloxy groups.

Examples of the acyl group include acetyl, propionyl and butyryl groups.

Examples of the halogen atom include fluorine, chlorine, bromine and iodine atoms.

Examples of the alkylcarbonyloxy group include methylcarbonyloxy, ethylcarbonyloxy, n-propylcarbonyloxy, isopropylcarbonyloxy, n-butylcarbonyloxy, sec-butylcarbonyloxy, tert-butyl carbonyloxy, pentylcarbonyloxy, hexylcarbonyloxy, octylcarbonyloxy and 2-ethylhexylcarbonyloxy groups.

The sulfur atom-containing ring which is formed by $R^{b4}$ and $R^{b5}$ may be a monocyclic or polycyclic group, which may be an aromatic or non-aromatic group, and which may be a saturated or unsaturated group. The ring is preferably a ring having 3 to 18 carbon atoms, and more preferably a ring having 4 to 18 carbon atoms. Examples of the sulfur atom-containing ring include a 3- to 12-membered ring, preferably a 3- to 7-membered ring, examples thereof include the following rings.

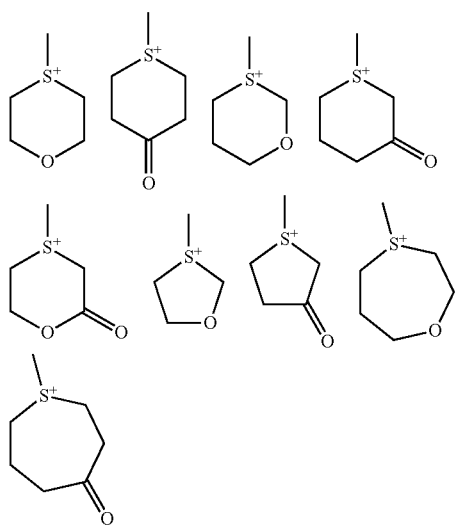

The sulfur atom-containing ring which is formed by $R^{b9}$ and $R^{b10}$ may be any of monocyclic, polycyclic, aromatic, non-aromatic, saturated and unsaturated rings. The ring may be a 3- to 12-membered ring, preferably a 3- to 7-membered ring. Examples of the ring include thiolane-1-ium ring (tetrahydrothiophenium ring), thian-1-ium ring and 1,4-oxathian-4-ium ring.

Examples of the ring formed by $R^{b11}$ and $R^{b12}$ may be any of monocyclic, polycyclic, aromatic, non-aromatic, saturated and unsaturated rings. The ring may be a 3- to 12-membered ring, preferably a 3- to 7-membered ring. Examples of the ring include oxocycloheptane ring, oxocyclohexane ring, oxonorbornane ring and oxoadamantane ring.

Among the cations represented by the formula (b2-1) to the formula (b2-4), the cation represented by the formula (b2-1) is preferred.

Examples of the cation (b2-1) include the following ones.

(b2-c-1)

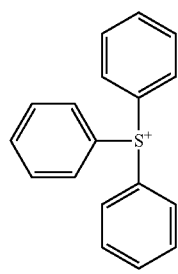

(b2-c-2)

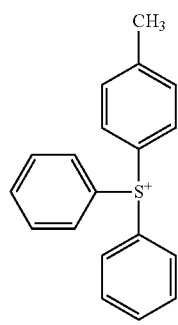

(b2-c-3)

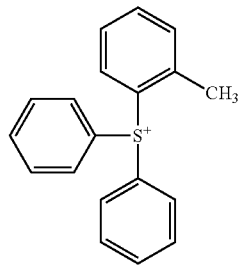

(b2-c-4)

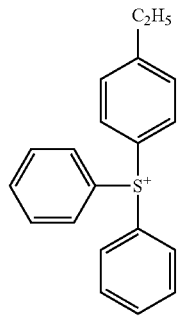

(b2-c-5)

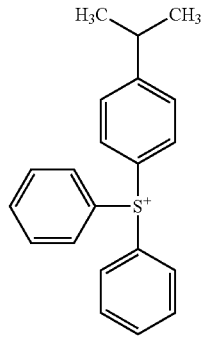

(b2-c-6)

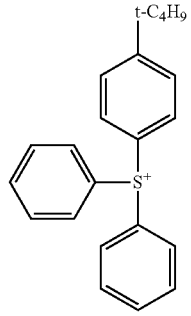

(b2-c-7)

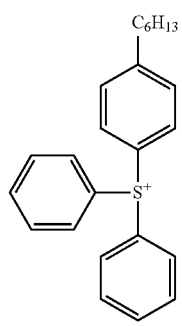

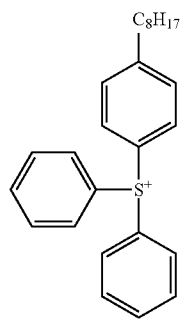 (b2-c-8)
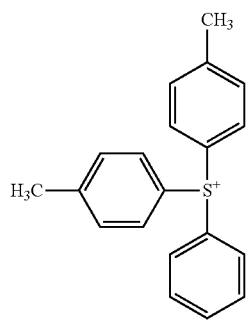 (b2-c-9)
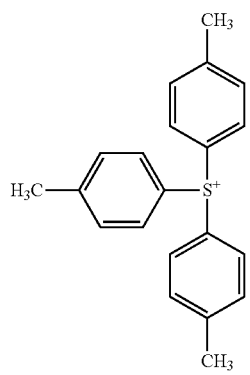 (b2-c-10)
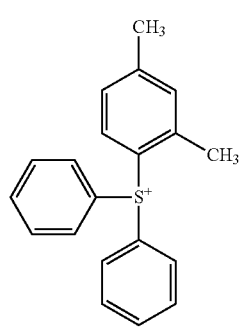 (b2-c-11)
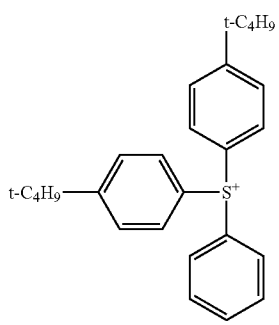 (b2-c-12)
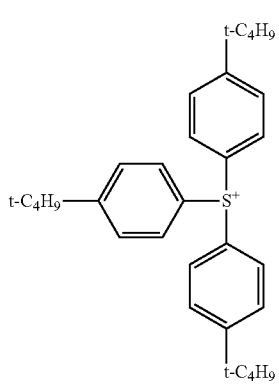 (b2-c-13)
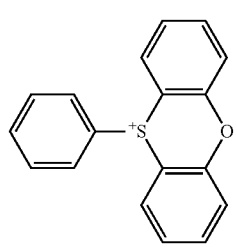 (b2-c-14)
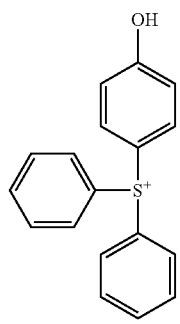 (b2-c-15)
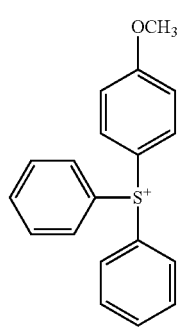 (b2-c-16)

-continued
(b2-c-17)
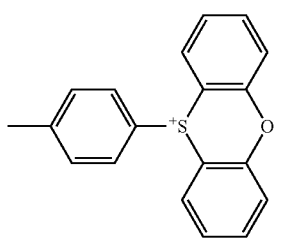
(b2-c-18)
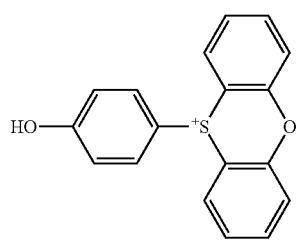
(b2-c-19)
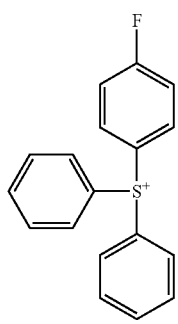
(b2-c-20)
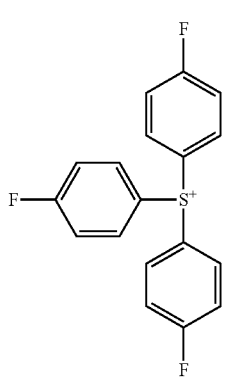
(b2-c-21)
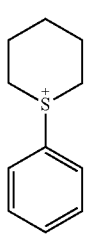
(b2-c-22)
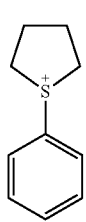
-continued
(b2-c-23)
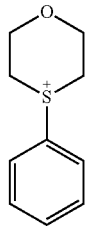
(b2-c-24)
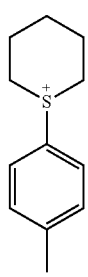
(b2-c-25)
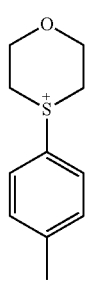
(b2-c-26)
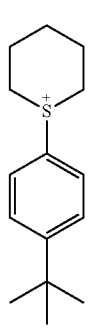
(b2-c-27)
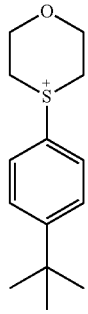
Examples of the cation (b2-2) include the following ones.
(b2-c-28)
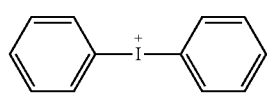

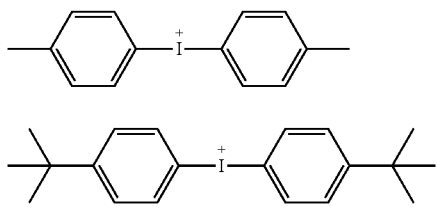
(b2-c-29)
(b2-c-30)
Examples of the cation (b2-3) include the following ones.
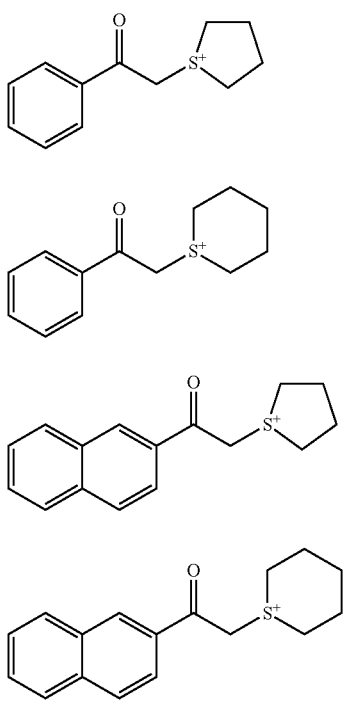
(b2-c-31)
(b2-c-32)
(b2-c-33)
(b2-c-34)
Examples of the cation (b2-4) include the following ones.
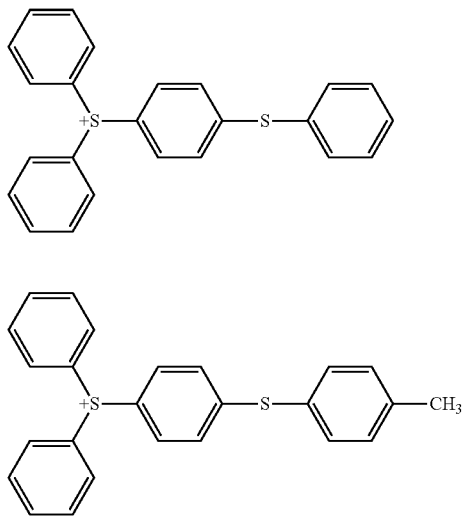
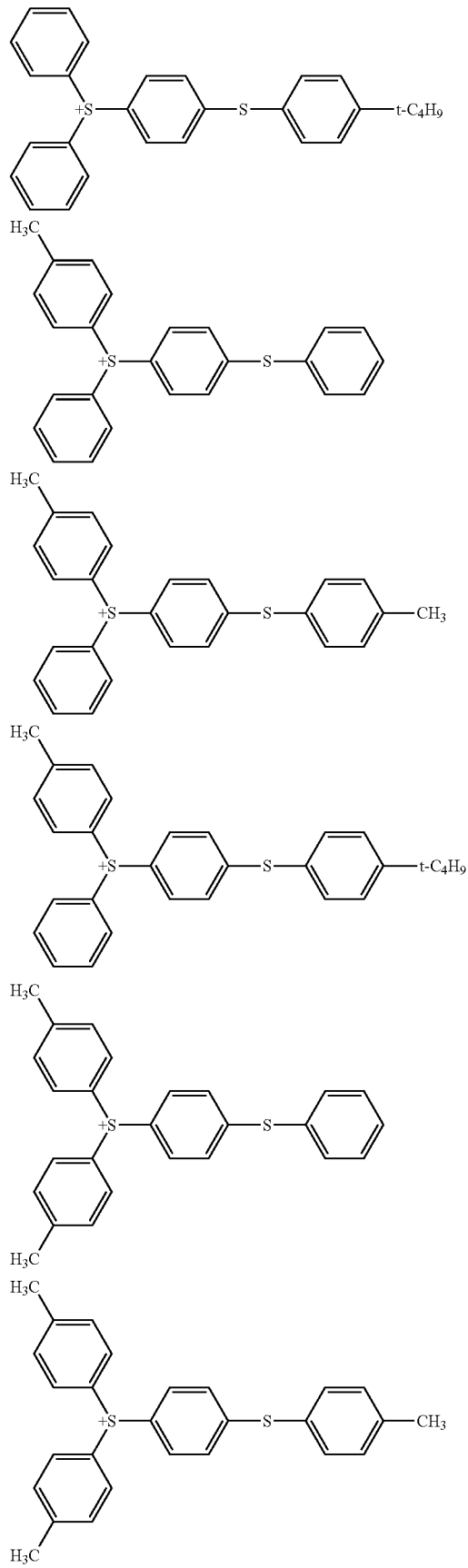

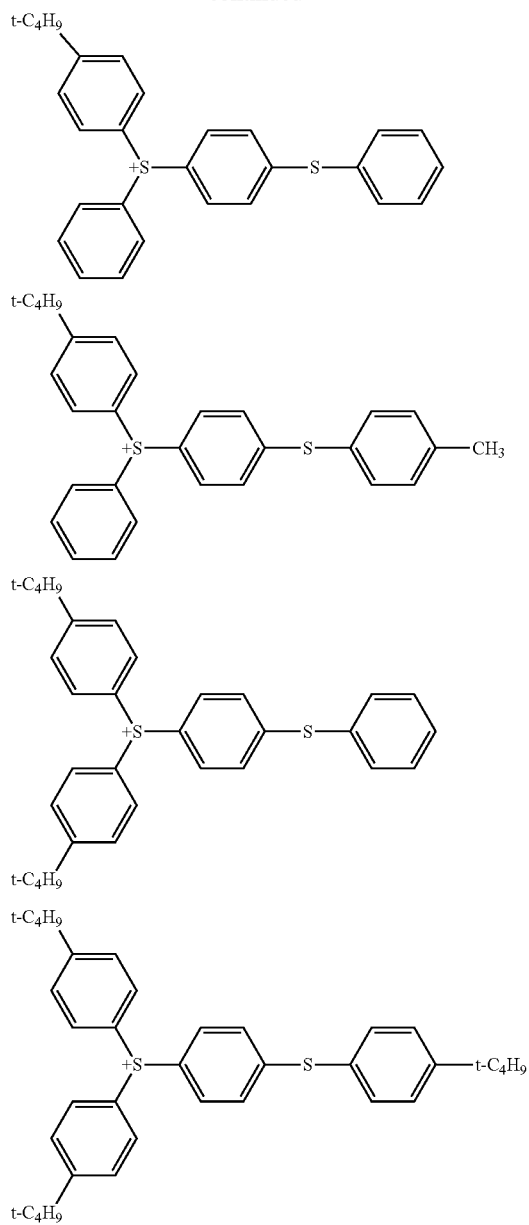

The acid generator (B1) is generally a compound which consists of the above sulfonate anion with an organic cation. The above sulfonic acid anion and the organic cation may optionally be combined. Preferred combination is a combination of any of the anion represented by the formula (B1a-1) to the formula (B1a-3), the formula (B1a-7) to the formula (B1a-15) and the cation represented by the formula (b2-1) or the formula (b2-3).

Preferred acid generators (B1) are represented by formula (B1-1) to formula (B1-30). Among these, formulae (B1-1), (B1-2), (B1-3), (B1-5), (B1-6), (B1-7), (B1-11), (B1-12), (B1-13), (B1-14), (B1-17), (B1-20), (B1-21), (B1-23), (B1-24), (B1-25), (B1-26) and (B1-29) which contain arylsulfonium cation are preferred.

-continued
(B1-5)
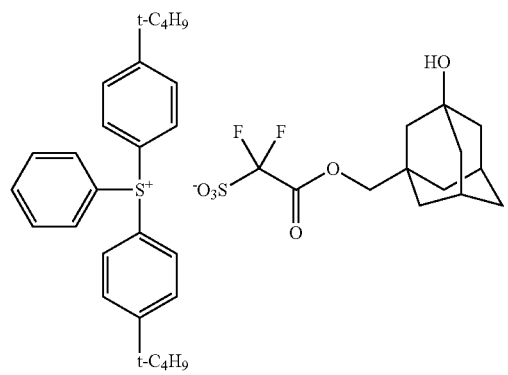
(B1-6)
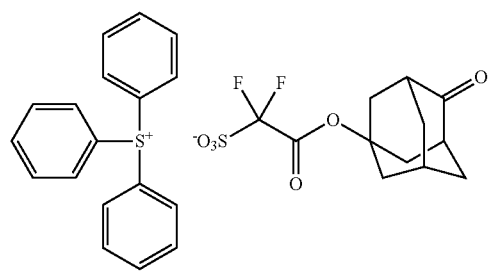
(B1-7)
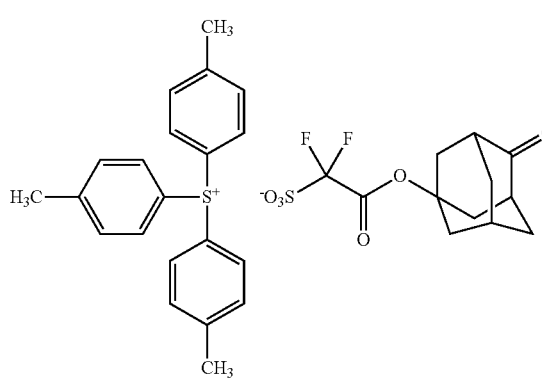
(B1-8)
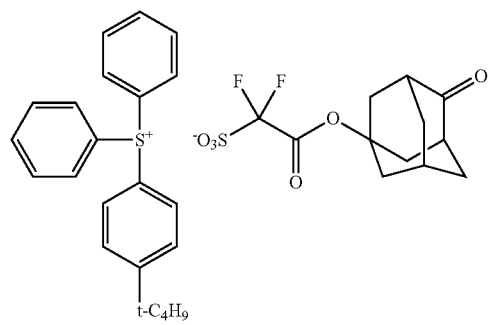
-continued
(B1-9)
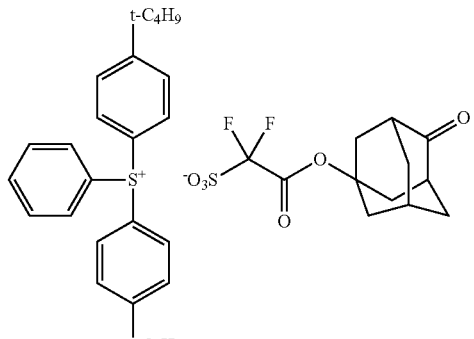
(B1-10)
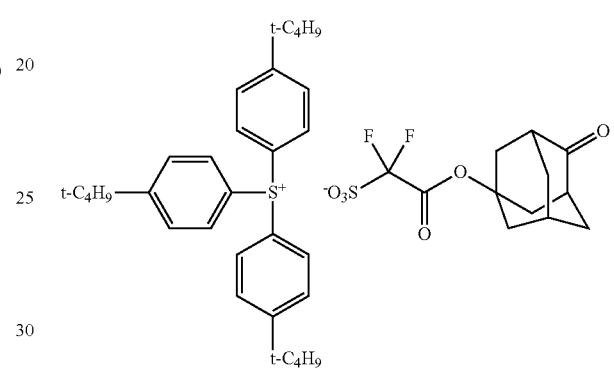
(B1-11)
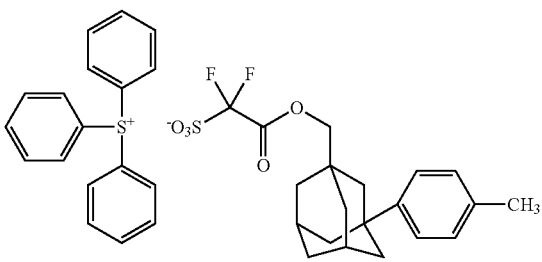
(B1-12)
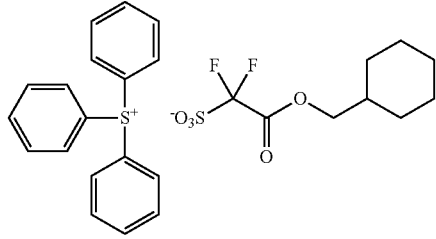
(B1-13)
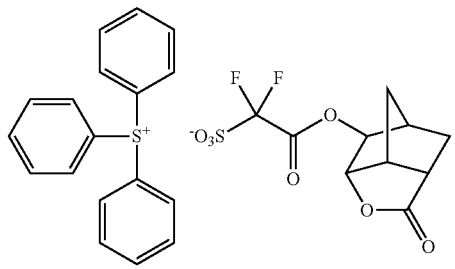

(B1-14)
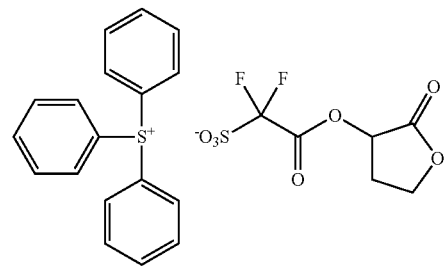
(B1-15)
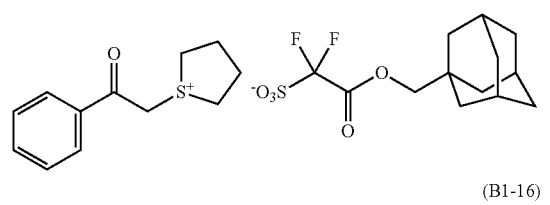
(B1-16)
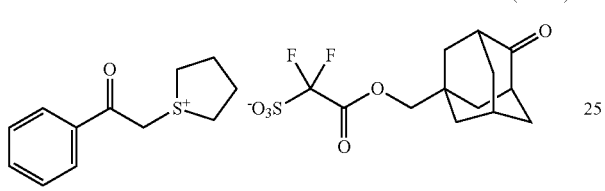
(B1-17)
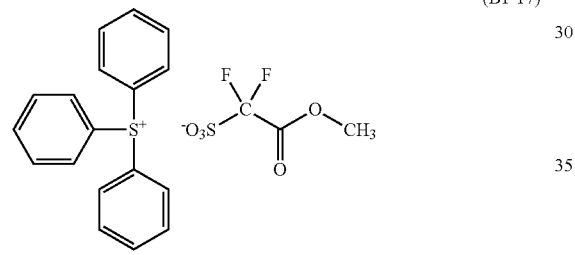
(B1-18)
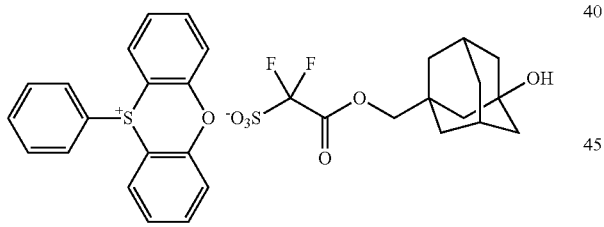
(B1-19)
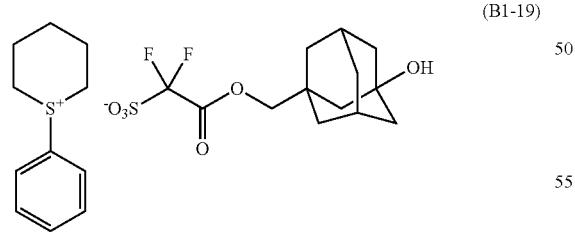
(B1-20)
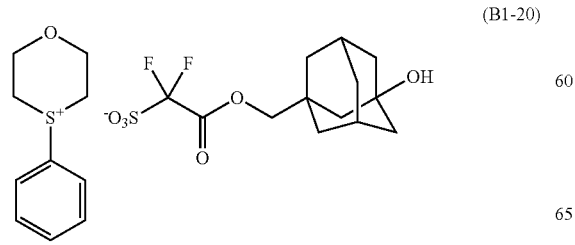
(B1-21)
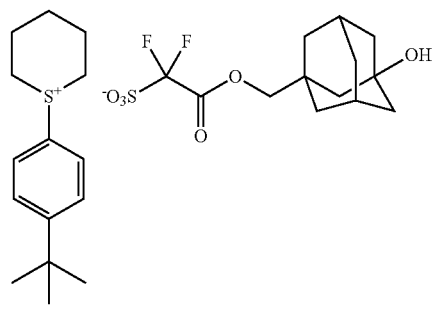
(B1-22)
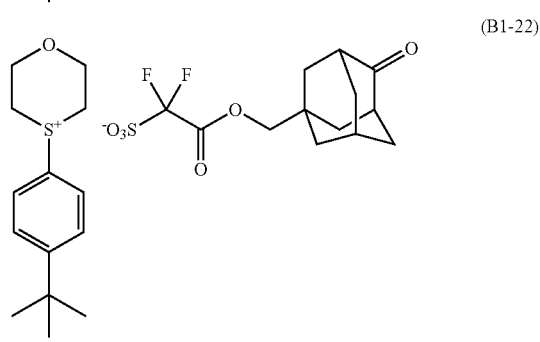
(B1-23)
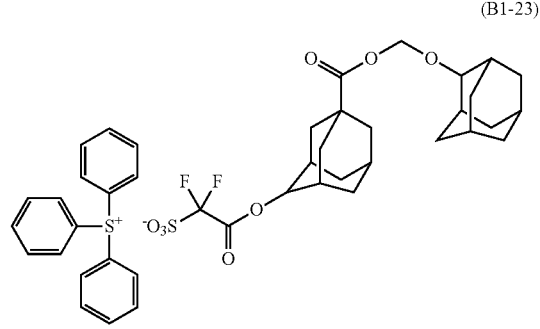
(B1-24)
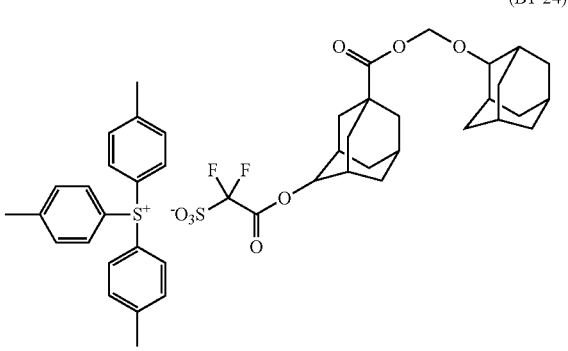
(B1-25)
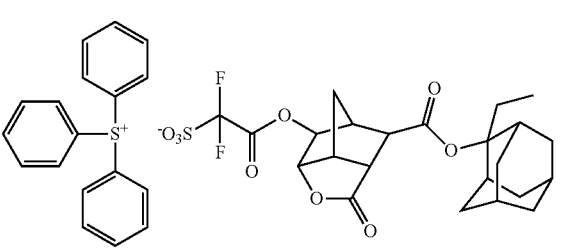

-continued (B1-26)
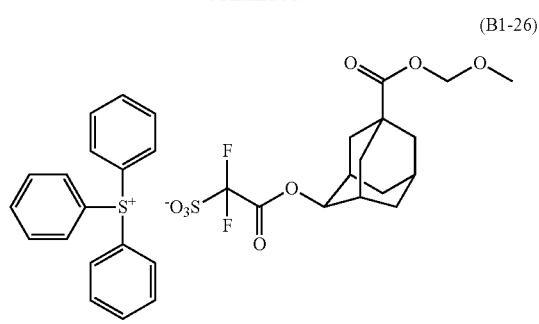

(B1-27)

(B1-28)
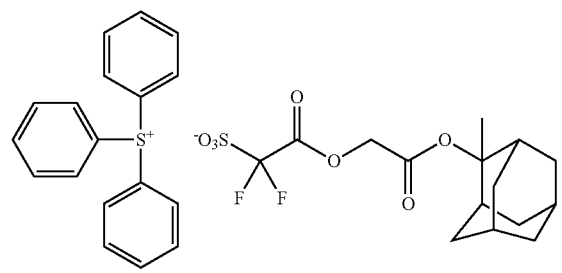

(B1-29)
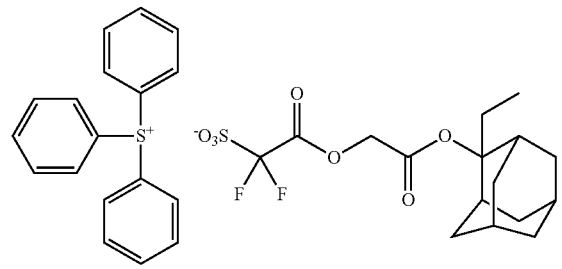

-continued (B1-30)
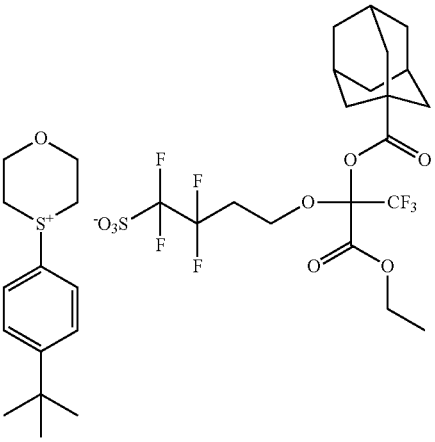

The proportion of the acid generator (B1) is preferably 30% by mass or more, and 100% by mass or less, more preferably 50% by mass or more, and 100% by mass or less, and still more preferably substantially 100% by weight with respect to 100% by mass of total acid generator (B).

In the resist composition of the disclosure, the proportion of the acid generator (B) is preferably 1 parts by mass or more and more preferably 3 parts by mass or more, and preferably 30 parts by mass or less and more preferably 25 parts by mass or less with respect to 100 parts by mass of the resin (A1).

<Solvent (E)>

The proportion of a solvent (E) is generally 90% by mass or more, preferably 92% by mass or more, and more preferably 94% by mass or more, and also preferably 99% by mass or less, and more preferably 99.9% by mass or less. The proportion of the solvent (E) can be measured with a known analytical method such as liquid chromatography and gas chromatography.

Examples of the solvent (E) include glycol ether esters such as ethylcellosolve acetate, methylcellosolve acetate and propyleneglycolmonomethylether acetate; glycol ethers such as propyleneglycolmonomethylether; esters such as ethyl lactate, butyl acetate, amyl acetate and ethyl pyruvate; ketones such as acetone, methyl isobutyl ketone, 2-heptanone and cyclohexanone; and cyclic esters such as γ-butyrolactone. These solvents may be used as a single solvent or as a mixture of two or more solvents.

<Quencher (C)>

The resist composition of the disclosure may further contain a quencher such as a basic nitrogen-containing organic compound and a salt which generates an acid weaker in acidity than an acid generated from the acid generator.

Examples of the quencher include a basic nitrogen-containing organic compound and a salt which generates an acid weaker in acidity than an acid generated from the acid generator (B).

<Basic Nitrogen-Containing Organic Compound>

Examples of the basic nitrogen-containing organic compound include an amine and ammonium salts.

Examples of the amine include an aliphatic amine and an aromatic amine. Examples of the aliphatic amine include a primary amine, secondary amine and tertiary amine. Specific examples of the amine include 1-naphtylamine, 2-naphtylamine, aniline, diisopropylaniline, 2-, 3- or 4-methylaniline, 4-nitroaniline, N-methylaniline, N,N-dimethylaniline, diphenylamine, hexylamine, heptylamine, octylamine, nonylamine, decylamine, dibutylamine, dipentylamine, dihexylamine, diheptylamine, dioctylamine, dinonylamine, didecylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecylamine, dicyclohexylmethylamine, tris[2-(2-methoxyethoxy)ethyl]amine, triisopropanolamine, ethylene diamine, tetramethylene diamine, hexamethylene diamine, 4,4'-diamino-1,2-diphenylethane, 4,4'-diamino-3,3'-dimethyldiphenylmnethane, 4,4'-diamino-3,3'-diethyldiphenylmethane, 2,2'-methylenebisaniline, imidazole, 4-methylimidazole, pyridine, 4-methylpyridine, 1,2-di(2-pyridyl)ethane, 1,2-di(4-pyridyl)ethane, 1,2-di(2-pyridyl)ethene, 1,2-di(4-pyridyl)ethene, 1,3-di(4-pyridyl) propane, 1,2-di(4-pyridyloxy)ethane, di(2-pyridyl)ketone, 4,4'-dipyridyl sulfide, 4,4'-dipyridyl disulfide, 2,2'-dipyridylamine, 2,2'-dipicolylamine and bipyridine. Among these, diisopropylaniline is preferred, particularly 2,6-diisopropylaniline is more preferred.

Specific examples of the ammonium salt include tetramethylammonium hydroxide, tetraisopropylammonium hydroxide, tetrabutylammonium hydroxide, tetrahexylammonium hydroxide, tetraoctylammonium hydroxide, phenyltrimethyl ammonium hydroxide, 3-(trifluoromethyl)phenyltrimethylammonium hydroxide, tetra-n-butyl ammonium salicylate and choline.

<Weak Acid Salt>

The salt generating an acid which is lower in acidity than an acid generated from the acid generator (B) is sometimes referred to as "weak acid salt". The "acidity" can be represented by acid dissociation constant, pKa, of an acid generated from a weak acid salt. Examples of the weak acid salt include a salt generating an acid of pKa represents generally more than −3, preferably −1 to 7, and more preferably 0 to 5.

Specific examples of the weak acid salt include the following salts, the salt of formula (D), and salts as disclosed in JP2012-229206A1, JP2012-6908A1, JP2012-72109A1, JP2011-39502A1 and JP2011-191745A1.

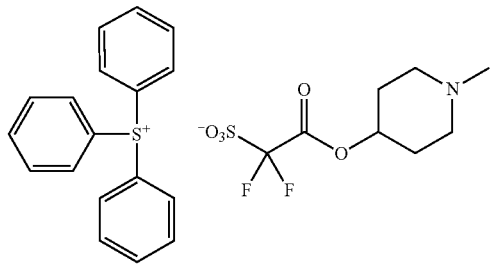

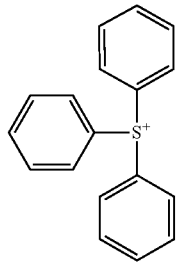

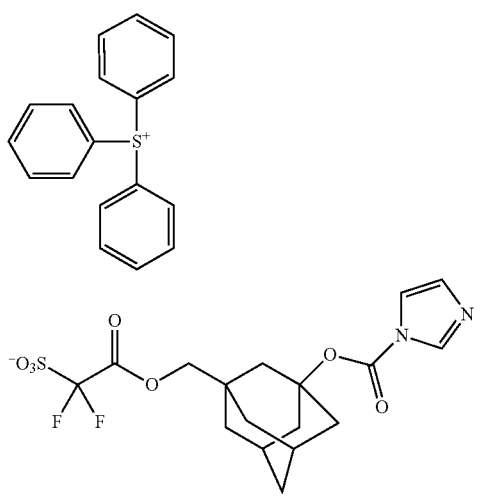

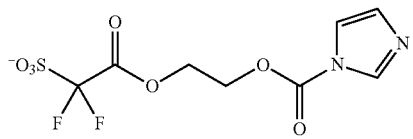

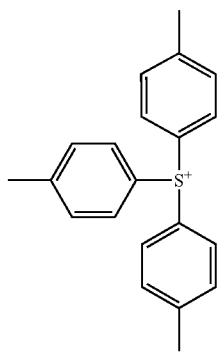

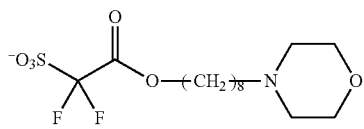

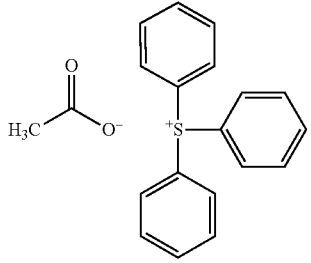

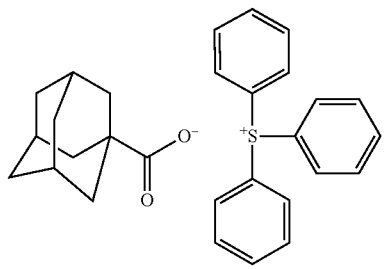

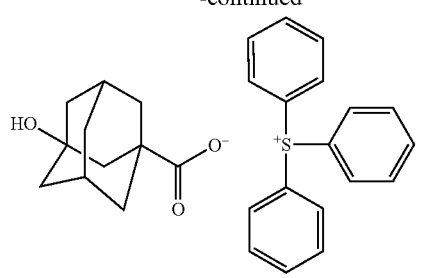
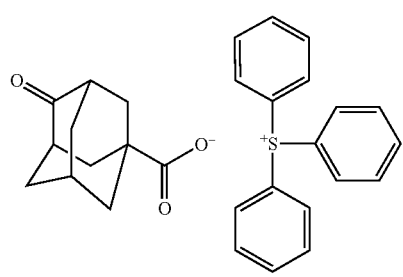
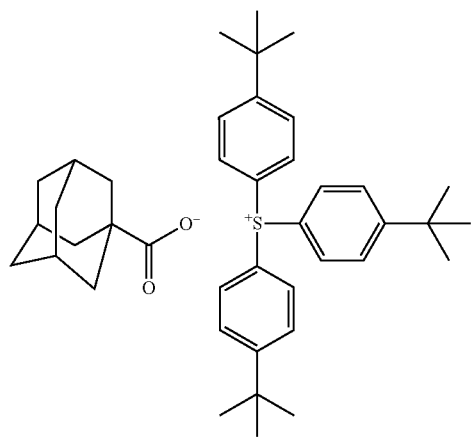
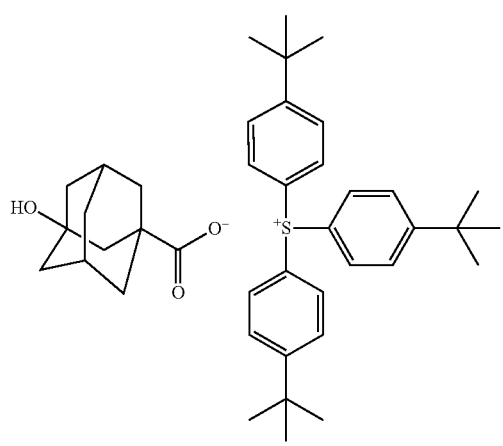
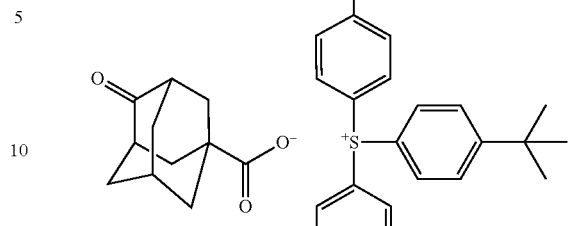
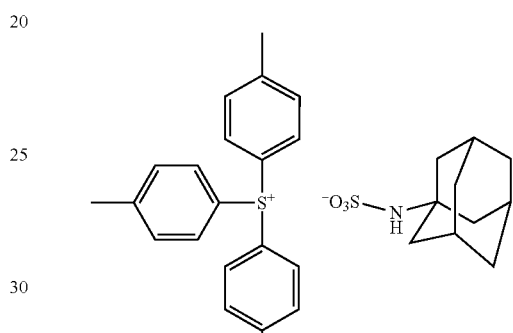
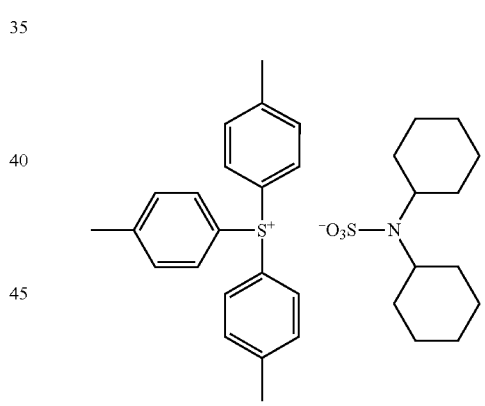
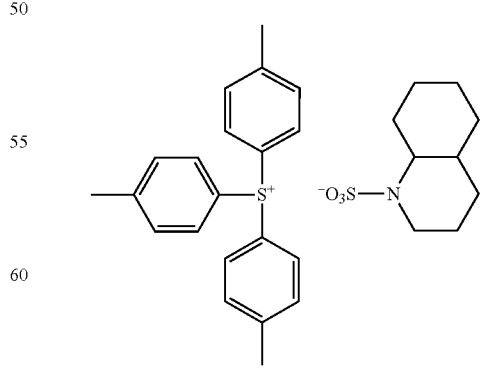
A weakly acidic inner salt (D) is a compound represented by the formula (D).

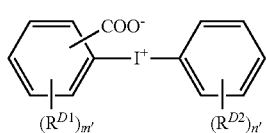

(D)

In the formula (D), $R^{D1}$ and $R^{D2}$ in each occurrence independently represent a $C_1$ to $C_{12}$ hydrocarbon group, a $C_1$ to $C_6$ alkoxyl group, a $C_2$ to $C_7$ acyl group, a $C_2$ to $C_7$ acyloxy group, a $C_2$ to $C_7$ alkoxycarbonyl group, a nitro group or a halogen atom;

m' and n' each independently represent an integer of 0 to 4.

Examples of the hydrocarbon group of $R^{D1}$ and $R^{D2}$ include any of an aliphatic hydrocarbon group, an alicyclic hydrocarbon group, an aromatic hydrocarbon group and a combination thereof.

Examples of the aliphatic hydrocarbon group include an alkyl group such as methyl, ethyl, propyl, isopropyl, butyl, isobutyl, tert-butyl, pentyl, hexyl and nonyl groups.

The alicyclic hydrocarbon group is any one of monocyclic or polycyclic hydrocarbon group, and saturated or unsaturated hydrocarbon group. Examples thereof include a cycloalkyl group such as cyclopropyl, cyclobutyl, cyclopentyl, cyclohexyl, cyclononyl and cyclododecyl groups; adamantyl and norbornyl groups.

Examples of the aromatic hydrocarbon group include an aryl group such as phenyl, 1-naphthyl, 2-naphthyl, 2-methylphenyl, 3-methylphenyl, 4-methylphenyl, 4-ethylphenyl, 4-propylphenyl, 4-isopropylphenyl, 4-butylphenyl, 4-tert-butylphenyl, 4-hexylphenyl, 4-cyclohexylphenyl, anthryl, p-adamantylphenyl, tolyl, xylyl, cumenyl, mesityl, biphenyl, phenanthryl, 2,6-diethylphenyl and 2-methyl-6-ethylphenyl groups.

Examples of the combination thereof include an alkyl-cycloalkyl, a cycloalkyl-alkyl, aralkyl (e.g., phenylmethyl, 1-phenylethyl, 2-phenylethyl, 1-phenyl-1-propyl, 1-phenyl-2-propyl, 2-phenyl-2-propyl, 3-phenyl-1-propyl, 4-phenyl-1-butyl, 5-phenyl-1-pentyl and 6-phenyl-1-hexyl groups) groups.

Examples of the alkoxyl group include methoxy and ethoxy groups.

Examples of the acyl group include acetyl, propanonyl, benzoyl and cyclohexanecarbonyl groups.

Examples of the acyloxy group include a group in which oxy group (—O—) bonds to an acyl group.

Examples of the alkoxycarbonyl group include a group in which the carbonyl group (—CO—) bonds to the alkoxy group.

Example of the halogen atom is a chlorine atom, a fluorine atom and bromine atom.

In the formula (D), $R^{D1}$ and $R^{D2}$ in each occurrence independently preferably represent a $C_1$ to $C_8$ alkyl group, a $C_3$ to $C_{10}$ cycloalkyl group, a $C_1$ to $C_6$ alkoxyl group, a $C_2$ to $C_4$ acyl group, a $C_2$ to $C_4$ acyloxy group, a $C_2$ to $C_4$ alkoxycarbonyl group, a nitro group or a halogen atom.

m' and n' independently preferably represent an integer of 0 to 3, more preferably an integer of 0 to 2, and more preferably 0.

Specific examples of the salt of the formula (D) include compounds below.

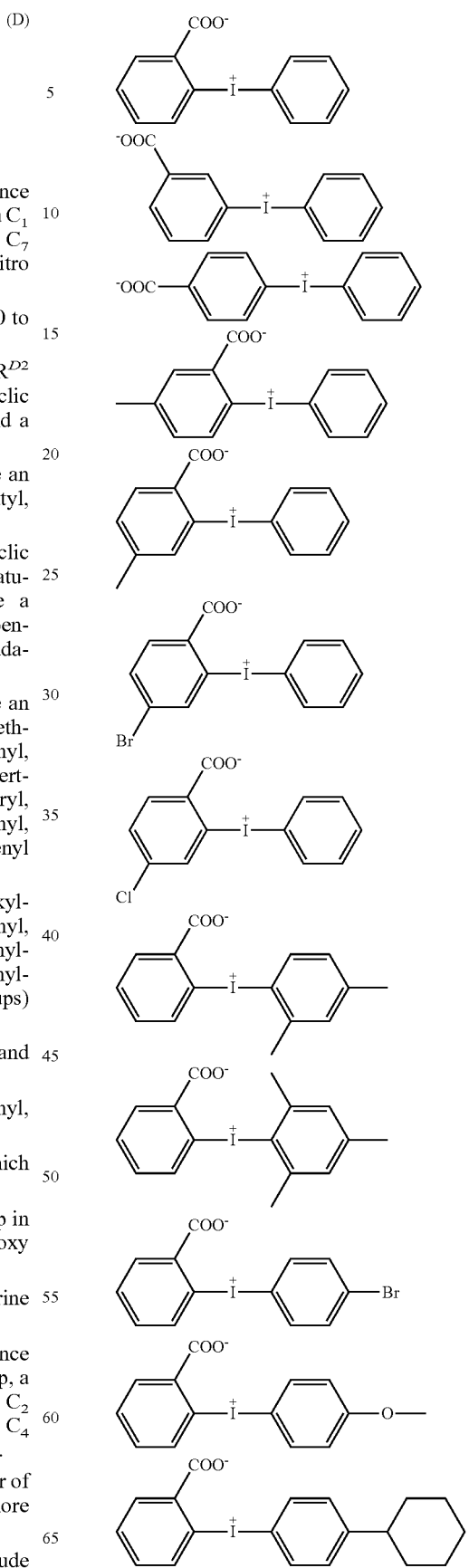

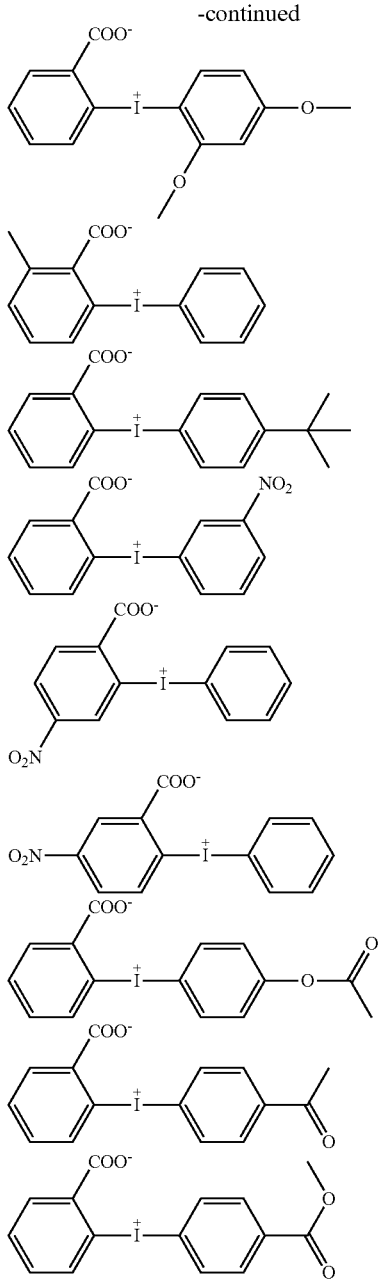

-continued

The salt of the formula (D) can be produced by a method described in "Tetrahedron Vol. 45, No. 19, p6281-6296". Also, commercially available compounds can be used as the salt of the formula (D).

In the resist composition of the disclosure, the proportion of the quencher is preferably 0.01% by mass to 5% by mass, more preferably 0.01% by mass to 4% by mass, and still more preferably 0.01% by mass to 3% by mass with respect to total solid components of the resist composition.

<Other Ingredient>

The resist composition can further contain other ingredient (which is sometimes referred to as "other ingredient (F)"). Examples of the other ingredient (F) include various additives such as sensitizers, dissolution inhibitors, surfactants, stabilizers, and dyes, as needed.

<Preparing the Resist Composition>

The present resist composition can be prepared by mixing the resins (X) and (A), the acid generator (B), the quencher (C), the solvent (E) and the other ingredient (F), as needed. There is no particular limitation on the order of mixing. The mixing may be performed in an arbitrary order. The temperature of mixing may be adjusted to an appropriate temperature within the range of 10 to 40° C., depending on the kinds of the resin and solubility in the solvent (E) of the resin. The time of mixing may be adjusted to an appropriate time within the range of 0.5 to 24 hours, depending on the mixing temperature. There is no particular limitation to the tool for mixing. An agitation mixing may be used.

After mixing the above ingredients, the present resist compositions can be prepared by filtering the mixture through a filter having about 0.003 to 0.2 µm pore diameter.

<Method for Producing Resist Pattern>

The method for producing a resist pattern of the disclosure includes the steps of:

(1) applying the resist composition of the disclosure onto a substrate;
(2) drying the applied composition to form a composition layer;
(3) exposing the composition layer;
(4) heating the exposed composition layer; and
(5) developing the heated composition layer.

Applying the resist composition onto the substrate can generally be carried out through the use of a resist application device, such as a spin coater known in the field of semiconductor microfabrication technique. Examples of the substrate include inorganic substrates such as silicon wafer. The substrate may be washed, and an organic antireflection film may be formed on the substrate by use of a commercially available antireflection composition, before the application of the resist composition.

The solvent evaporates from the resist composition and a composition layer with the solvent removed is formed. Drying the applied composition layer, for example, can be carried out using a heating device such as a hotplate (so-called "prebake"), a decompression device, or a combination thereof. The temperature is preferably within the range of 50 to 200° C. The time for heating is preferably 10 to 180 seconds. The pressure is preferably within the range of 1 to $1.0 \times 10^5$ Pa.

The obtained composition layer is generally exposed using an exposure apparatus or a liquid immersion exposure apparatus. The exposure is generally carried out using with various types of exposure light source, such as irradiation with ultraviolet lasers, i.e., KrF excimer laser (wavelength: 248 nm), ArF excimer laser (wavelength: 193 nm), $F_2$ excimer laser (wavelength: 157 nm), irradiation with harmonic laser light of far-ultraviolet or vacuum ultra violet wavelength-converted laser light from a solid-state laser source (YAG or semiconductor laser or the like), or irradiation with electron beam or EUV or the like. In the specification, such exposure to radiation is sometimes referred to be collectively called as exposure. The exposure is generally carried out through a mask that corresponds to the desired pattern. When electron beam is used as the exposure light source, direct writing without using a mask can be carried out.

After exposure, the composition layer is subjected to a heat treatment (so-called "post-exposure bake") to promote the deprotection reaction. The heat treatment can be carried out using a heating device such as a hotplate. The heating temperature is generally in the range of 50 to 200 OC, preferably in the range of 70 to 150° C.

The developing of the baked composition film is usually carried out with a developer using a development apparatus. Developing can be conducted in the manner of dipping method, paddle method, spray method and dynamic dispensing method. Temperature for developing is generally 5 to 60 OC. The time for developing is preferably 5 to 300 seconds.

The photoresist pattern obtained from the photoresist composition may be a positive one or a negative one by selecting suitable developer.

The development for obtaining a positive photoresist pattern is usually carried out with an alkaline developer. The alkaline developer to be used may be any one of various alkaline aqueous solution used in the art. Generally, an aqueous solution of tetramethylammonium hydroxide or (2-hydroxyethyl)trimethylammonium hydroxide (commonly known as "choline") is often used. The surfactant may be contained in the alkaline developer.

After development, the resist pattern formed is preferably washed with ultrapure water, and the residual water remained on the resist film or on the substrate is preferably removed therefrom.

The development for obtaining a negative photoresist pattern is usually carried out with a developer containing an organic solvent. The organic solvent to be used may be any one of various organic solvents used in the art, examples of which include ketone solvents such as 2-hexanone, 2-heptanone; glycol ether ester solvents such as propyleneglycol-monomethylether acetate; ester solvents such as the butyl acetate; glycol ether solvents such as the propyleneglycol-monomethylether; amide solvents such as N,N-dimethylacetamide; aromatic hydrocarbon solvents such as anisole.

In the developer containing an organic solvent, the amount of organic solvents is preferably 90% by mass to 100% by mass, more preferably 95% by mass to 100% by mass of the developer. The developer still more preferably consists essentially of organic solvents.

Among these, the developer containing an organic solvent preferably contains butyl acetate and/or 2-heptanone. In the developer containing an organic solvent, the total amount of butyl acetate and 2-heptanone is preferably 50% by mass to 100% by mass of the developer, more preferably 90% by mass to 100% by mass of the developer. The developer still more preferably consists essentially of butyl acetate and/or 2-heptanone.

Developers containing an organic solvent may contain a surfactant. Also, the developer containing an organic solvent may include a little water.

The developing with a developer containing an organic solvent can be finished by replacing the developer by another solvent.

After development, the photoresist pattern formed is preferably washed with a rinse agent. Such rinse agent is not unlimited provided that it does not detract a photoresist pattern. Examples of the agent include solvents which contain organic solvents other than the above-mentioned developers, such as alcohol agents or ester agents.

After washing, the residual rinse agent remained on the substrate or photoresist film is preferably removed therefrom.

<Application>

The resist composition of the disclosure is useful for excimer laser lithography such as ArF, KrF, electron beam (EB) exposure lithography or extreme-ultraviolet (EUV) esposure lithography, and is more useful for ArF excimer laser exposure lithography.

The resist composition of the disclosure can be used in semiconductor microfabrication.

EXAMPLES

The disclosure will be described more specifically by way of examples, which are not construed to limit the scope of the disclosure.

All percentages and parts expressing the content or amounts used in the Examples and Comparative Examples are based on mass, unless otherwise specified.

The weight average molecular weight is a value determined by gel permeation chromatography.

Column: TSK gel Multipore HXL-M x 3+guardcolumn (Tosoh Co. Ltd.)
Eluant: tetrahydrofuran
Flow rate: 1.0 mL/min
Detecting device: RI detector
Column temperature: 40° C.
Injection amount: 100 μL
Standard material for calculating molecular weight: standard polystyrene (Tosoh Co. ltd.)

Structures of compounds were determined by mass spectrometry (Liquid Chromatography: 1100 Type, manufactured by AGILENT TECHNOLOGIES LTD., Mass Spectrometry: LC/MSD Type, manufactured by AGILENT TECHNOLOGIES LTD.). The value of the peak in the mass spectrometry is referred to as "MASS".

Example 1

Synthesis of the compound represented by formula (I-1)

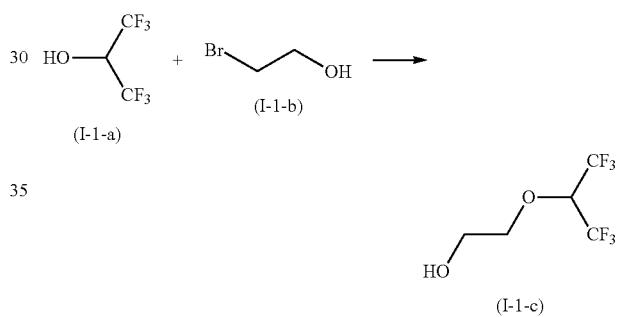

5.01 Part of potassium hydroxide and 120 parts of methyl ethyl ketone were mixed, stirred at 23° C. for 30 minutes, and cooled into 5° C. to obtain an alkaline solution. To the obtained alkaline solution, 15 parts of the compound represented by the formula (I-1-a) was added at 5° C. for 20 minutes and stirred at 23° C. for 2 hours. To the obtained mixture, 13.39 parts of the compound represented by the formula (I-1-b) was added, refluxed and stirred at 85° C. for 12 hours, and cooled into 23° C. To the obtained mixture, 60 parts of ion-exchanged water was added and stirred at 23° C. for 30 minutes, and left still, followed by separating an organic layer to wash with water. The washing step with water was conducted three times. To the obtained organic layer, 60 parts of 5% aqueous oxalic acid solution was added, and stirred at 23 degree C. for 30 minutes. Then, the mixture was left still, followed by separating an organic layer. The washing step with water was conducted twice. To the organic layer, 60 parts of ion-exchanged water was added and stirred at 23° C. for 30 minutes, and left still, followed by separating an organic layer to wash with water. The washing step with water was conducted five times. The washed organic layer was concentrated and purified with column chromatography [silica gel 60N spherical shape, neutral, 100-210 m, eluent solvent: of ethyl acetate, manufactured by Kanto Chem. Ltd.] to obtain 7.53 parts of the compound represented by formula (I-1-c).

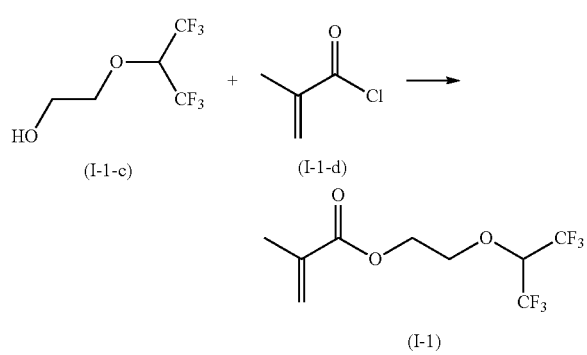

Into a reactor, 5.45 part of the compound represented by the formula (I-1-c), 40 parts of tetrahydrofuran and 8.75 parts of N-methylpyrrolidine were charged, and stirred at 23° C. for 30 minutes. To the obtained mixture, 9.40 parts of the compound represented by the formula (I-1-d) were added and stirred at 23° C. for 12 hours. Then, 40 parts of chloroform and 40 parts of 10% aqueous potassium carbonate solution were added and stirred at 23° C. for 30 minutes, and left still, followed by separating an organic layer. To the obtained organic layer, 40 parts of ion-exchanged water was added and stirred at 23° C. for 30 minutes, and left still, followed by separating an organic layer to wash with water. To the obtained organic layer, 40 parts of 10% aqueous oxalic acid solution was added, and stirred at 23 degree C. for 30 minutes. Then, the mixture was left still, followed by separating an organic layer to wash with water. The washing step with water was conducted four times. To the organic layer, 40 parts of ion-exchanged water was added, stirred at 23° C. for 30 minutes, and left still, followed by separating an organic layer to wash with water. The washing step with water was conducted four times. The washed organic layer was concentrated and purified with column chromatography [silica gel 60N spherical shape, neutral, 100-210 μm, eluent solvent: ethyl acetate, manufactured by Kanto Chem. Ltd.] to obtain 4.82 parts of the compound represented by formula (I-1).

MS (mass spectrography): 280.1 (molecular ion peak)

Synthesis Example 1

Synthesis of the compound represented by formula (I-8)

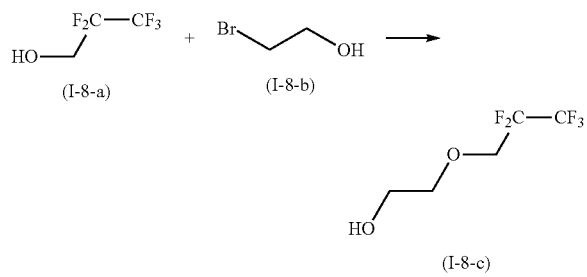

5.01 Part of potassium hydroxide and 120 parts of methyl ethyl ketone were mixed, stirred at 23° C. for 30 minutes, and cooled into 5° C. to obtain an alkaline solution. To the alkaline solution, 13.39 parts of the compound represented by the formula (I-8-a) was added at 5° C. for 20 minutes and stirred at 23° C. for 2 hours. 13.39 Parts of the compound represented by the formula (I-8-b) was added to the obtained mixture, then, refluxed and stirred at 85° C. for 12 hours, and cooled into 23° C. To the obtained mixture, 60 parts of ion-exchanged water was added and stirred at 23° C. for 30 minutes, and left still, followed by separating an organic layer to wash with water. The washing step with water was conducted three times. To the obtained organic layer, 60 parts of 5% aqueous oxalic acid solution was added, and stirred at 23 degree C. for 30 minutes. Then, the mixture was left still, followed by separating an organic layer. The washing step with water was conducted twice. 60 Parts of ion-exchanged water was added to the organic layer and stirred at 23° C. for 30 minutes, and left still, followed by separating an organic layer to wash with water. The washing step with water was conducted five times. The washed organic layer was concentrated and purified with column chromatography [silica gel 60N spherical shape, neutral, 100-210 μm, eluent solvent: ethyl acetate, manufactured by Kanto Chem. Ltd.] to obtain 6.68 parts of the compound represented by formula (I-8-c).

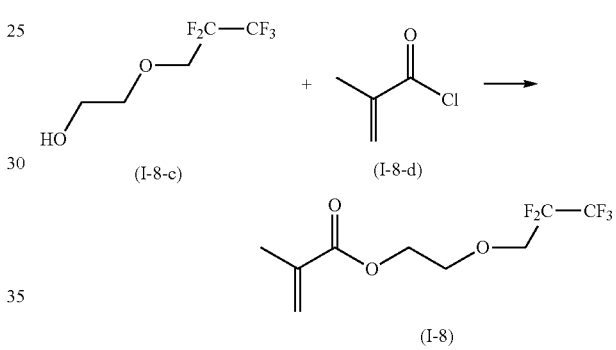

Into a reactor, 4.99 part of the compound represented by the formula (I-8-c), 40 parts of tetrahydrofuran and 8.75 parts of N-methylpyrrolidine were charged, and stirred at 23° C. for 30 minutes. To the obtained mixture, 9.40 parts of the compound represented by the formula (I-8-d) were added and stirred at 23° C. for 12 hours. Then, 40 parts of chloroform and 40 parts of 10% aqueous potassium carbonate solution were added and stirred at 23° C. for 30 minutes, and left still, followed by separating an organic layer. To the obtained organic layer, 40 parts of ion-exchanged water was added and stirred at 23° C. for 30 minutes, followed by separating an organic layer to wash with water. To the obtained organic layer, 40 parts of 10% aqueous oxalic acid solution was added, and stirred at 23 degree C. for 30 minutes. Then, the mixture was left still, followed by separating an organic layer to wash with water. The washing step with water was conducted four times. 40 Parts of ion-exchanged water was added to the organic layer and stirred at 23° C. for 30 minutes, and left still, followed by separating an organic layer to wash with water. The washing step with water was conducted four times. The washed organic layer was concentrated and purified with column chromatography [silica gel 60N spherical shape, neutral, 100-210 μm, eluent solvent: ethyl acetate, manufactured by Kanto Chem. Ltd.] to obtain 4.10 parts of the compound represented by formula (I-8).

MS (mass spectrography): 262.1 (molecular ion peak)

Synthesis Example 2

Synthesis of the salt represented by formula (B1-5)

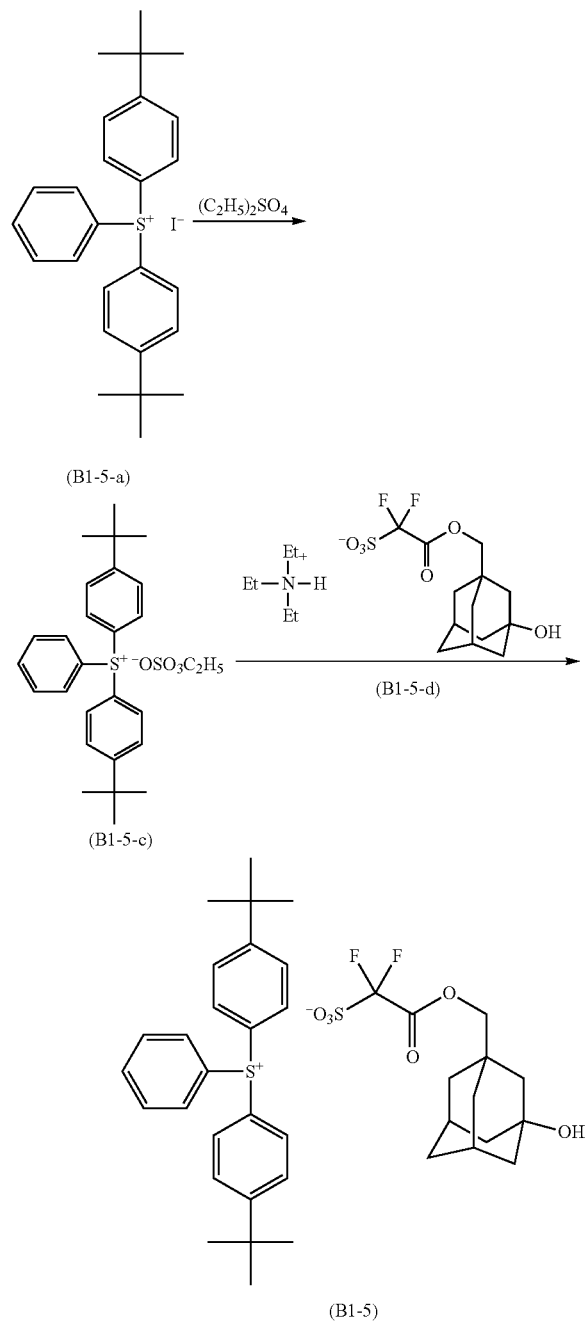

(B1-5-a)

(B1-5-c)

(B1-5-d)

(B1-5)

Into a reactor, 50.49 parts of a salt represented by the formula (B1-5-a) and 252.44 parts of chloroform were charged and stirred at 23° C. for 30 minutes. Then 16.27 parts of a compound represented by the formula (B1-5-b) were dropped thereinto and the obtained mixture was stirred at 23° C. for one hour to obtain a solution containing a salt represented by the formula (B1-5-c). To the obtained solution, 48.80 parts of a salt represented by the formula (B1-5-d) and 84.15 parts of ion-exchanged water were added and the obtained mixture was stirred at 23° C. for 12 hours. From the obtained solution which had two layers, a chloroform layer was collected and then 84.15 parts of ion-exchanged water were added thereto for washing. These steps were conducted five times. To the washed chloroform layer, 3.88 parts of active carbon was added and the obtained mixture was stirred, followed by filtrating. The collected filtrate was concentrated and then 125.87 parts of acetonitrile were added thereto and the obtained mixture was stirred, followed by being concentrated. 20.62 parts of acetonitrile and 309.30 parts of tert-butyl methyl ether were added to the obtained residues, followed by being stirred at 23° C. for about 30 minutes. Then a supernatant was removed therefrom, and the residues were concentrated. To the concentrated residues, 200 parts of n-heptane were added and the obtained mixture was stirred at 23° C. for about 30 minutes, followed by being filtrated to obtain 61.54 parts of the salt represented by the formula (B1-5).

MASS(ESI(+)Spectrum):M+ 375.2
MASS(ESI(−)Spectrum):M− 339.1

Synthesis Example 3

Synthesis of the salt represented by formula (B1-21)

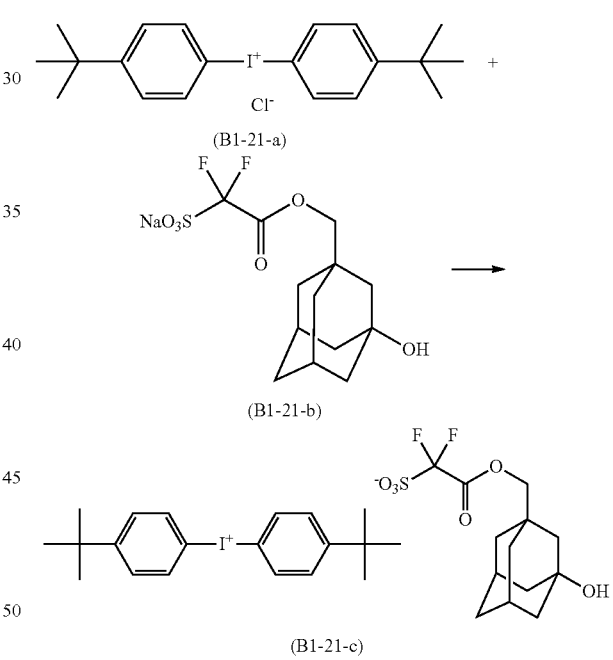

(B1-21-a)

(B1-21-b)

(B1-21-c)

The compound represented by the formula (B1-21-b) was produced according to a method recited in JP2008-209917A1.

Into a reactor, 30.00 parts of the compound represented by the formula (B1-21-b) and 35.50 parts of a salt represented by the formula (B1-21-a), 100 parts of chloroform and 50 parts of ion-exchanged water were charged and stirred at 23° C. for about 15 hours. From the obtained solution which had two layers, a chloroform layer was collected and then 30 parts of ion-exchanged water was added thereto for washing. These steps were conducted five times. Then the washed layer was concentrated, and then, 100 parts of tert-butyl methyl ether was added to the obtained residues and the obtained mixture was stirred at 23° C. for about 30 minutes.

The resulting mixture was filtrated to obtain 48.57 parts of the salt represented by the formula (B1-21-c).

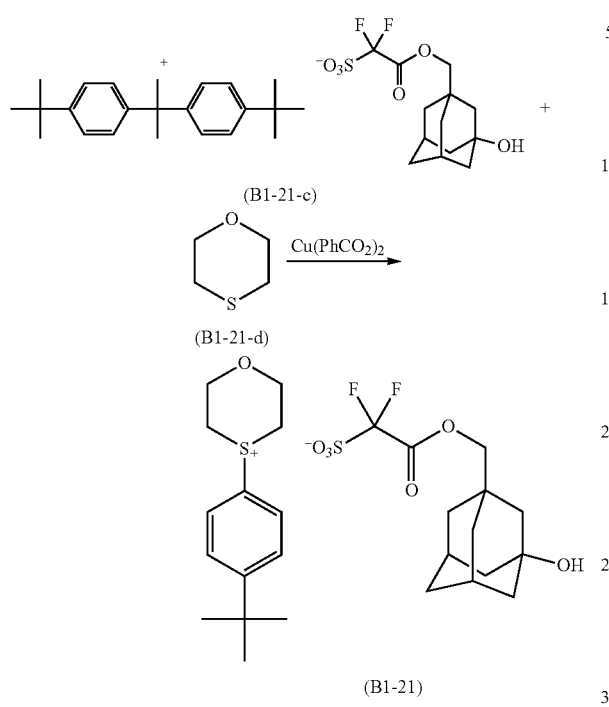

Into a reactor, 20.00 parts of salt represented by the formula (B1-21-c), 2.84 parts of compound represented by the formula (B1-21-d) and 250 parts of monochlorobenzene were charged and stirred at 23° C. for 30 minutes. To the resulting mixture, 0.21 parts of copper (II) dibenzoate was added and the obtained mixture was stirred at 100° C. for 1 hour. The reaction mixture was concentrated, and then, 200 parts of chloroform and 50 parts of ion-exchanged water were added to the obtained residues and the obtained mixture was stirred at 23° C. for 30 minutes, followed by separating an organic layer. 50 parts of ion-exchanged water was added to the obtained organic layer, and the obtained mixture was stirred at 23° C. for 30 minutes, followed by separating an organic layer. The washing step with water was conducted five times. The obtained organic layer was concentrated, and then the obtained residues were dissolved in 53.51 parts of acetonitrile. Then the mixture was concentrated, and 113.05 parts of tert-butyl methyl ether was added thereto and the obtained mixture was stirred, followed by filtrating it to obtain 10.47 parts of the salt represented by the formula (B1-21).

MASS(ESI(+)Spectrum):M+ 237.1
MASS(ESI(−)Spectrum):M− 339.1

Synthesis Example 4

Synthesis of the Salt Represented by Formula (B1-22)

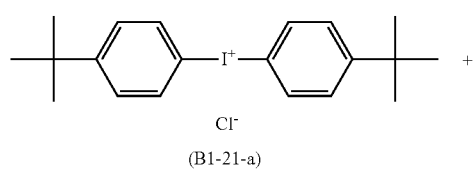

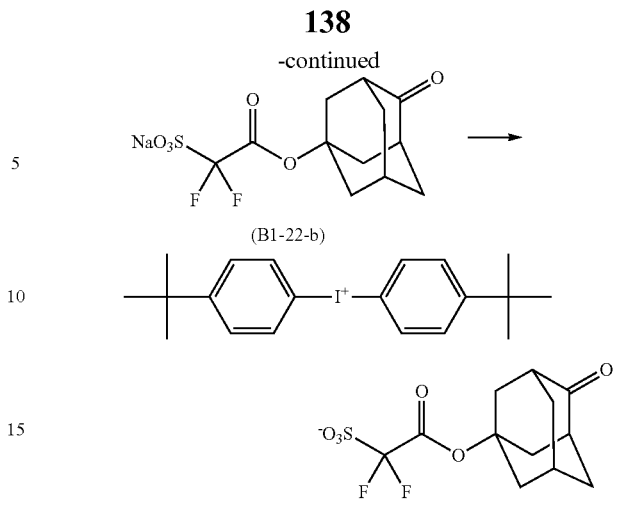

Into a reactor, 11.26 parts of the salt represented by the formula (B1-21-a), 10 parts of the compound represented by the formula (B1-22-b), 50 parts of chloroform and 25 parts of ion-exchanged water were charged and stirred at 23° C. for about 15 hours. From the obtained solution which had two layers, a chloroform layer was collected and then 15 parts of ion-exchanged water were added thereto for washing. These steps were conducted five times. Then the washed layer was concentrated, and then 50 parts of tert-butyl methyl ether was added to the obtained residues, and the obtained mixture was stirred at 23° C. for about 30 minutes. The resulting mixture was filtrated to obtain 11.75 parts of the salt represented by the formula (B1-22-c).

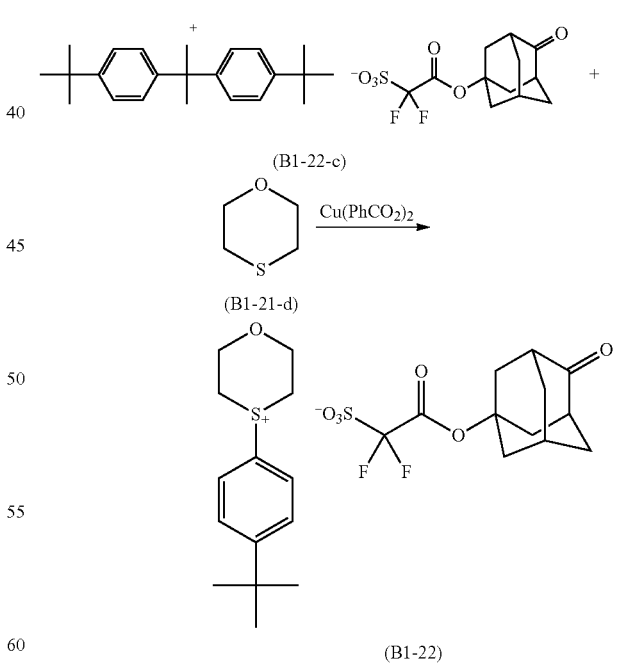

Into a reactor, 11.71 parts of the salt represented by the formula (B1-22-c), 1.70 parts of a compound represented by the formula (B1-21-d) and 46.84 parts of monochlorobenzene were charged and stirred at 23° C. for 30 minutes. To the resulting mixture, 0.12 parts of copper (II) dibenzoate was added and the obtained mixture was stirred at 100 OC for 30 minutes. The reaction mixture was concentrated, and then 50 parts of chloroform and 12.50 parts of ion-exchanged water were added to the obtained residues, and the obtained mixture was stirred at 23° C. for 30 minutes, followed by separating an organic layer. 12.50 parts of ion-exchanged water was added to the obtained organic layer and the obtained mixture was stirred at 23° C. for 30 minutes, followed by separating an organic layer to wash with water. The washing step with water was conducted eight times. Then the obtained organic layer was concentrated, and 50 parts of tert-butyl methyl ether were added thereto and the obtained mixture was stirred, followed by filtrating it to obtain 6.84 parts of the salt represented by the formula (B1-22).

MASS(ESI(+)Spectrum):M+ 237.1
MASS(ESI(−)Spectrum):M− 323.0

Synthesis Examples of Resins

The monomers used for Synthesis Examples of the resins are shown below. These monomers are referred to as "monomer (X)" where "(X)" is the symbol of the formula representing the structure of each monomer.

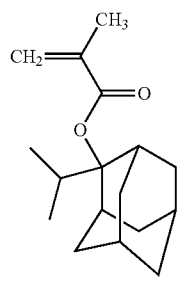
(a-1-1-3)

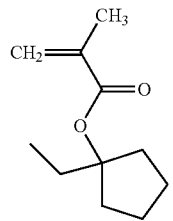
(a1-2-9)

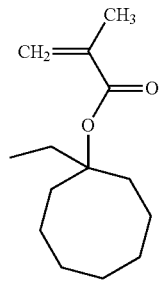
(a1-2-x)

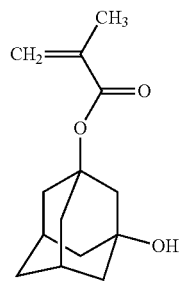
(a2-1-1)

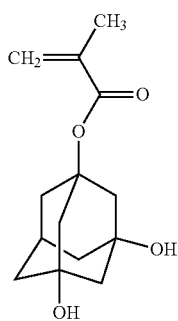
(a2-1-3)

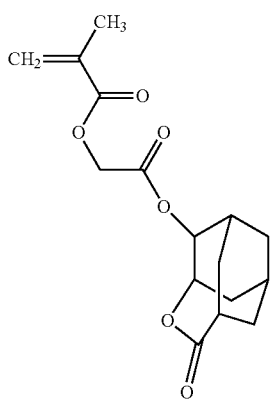
(a3-4-2)

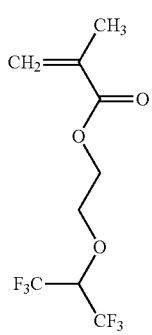
(I-1)

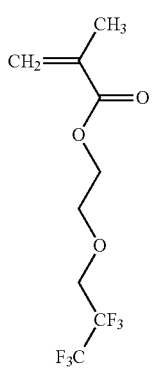
(I-8)

-continued (I-7)
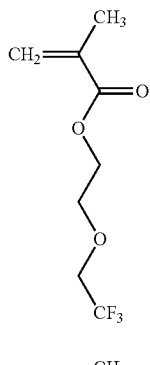

(IX-1)
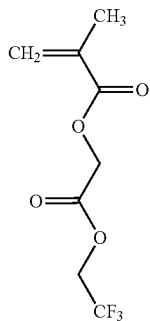

(IX-2)
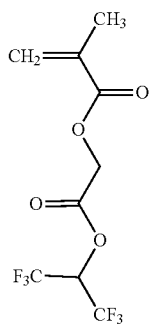

(a4-0-12)
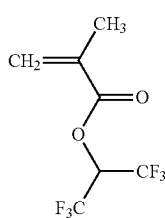

(a5-1-1)
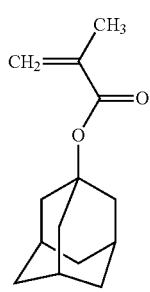

Synthesis Example 5

Synthesis of Resin A1-1

Monomer (a1-1-3), monomer (a1-2-9), monomer (a2-1-3) and monomer (a3-4-2) were mixed together with a mole ratio of monomer (a1-1-3), monomer (a1-2-9), monomer (a2-1-3) and monomer (a3-4-2)=45:14:2.5:38.5, and propyleneglycolmonomethylether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 1% by mole and 3% by mole respectively with respect to the total amount of monomers, and the resultant mixture was heated for about 5 hours at 73° C. Then, the obtained reaction mixture was poured into a large amount of a mixture of methanol and water to precipitate a resin. The obtained resin was filtrated. The obtained resin was dissolved in another propyleneglycolmonomethylether acetate to obtain a solution, and the solution was poured into a mixture of methanol and water to precipitate the resin. The obtained resin was filtrated. These operations were conducted twice to obtain the copolymer having a weight average molecular weight of about 7600 in 68% yield. This resin, which had the structural units of the following formulae, was referred to as Resin A1-1.

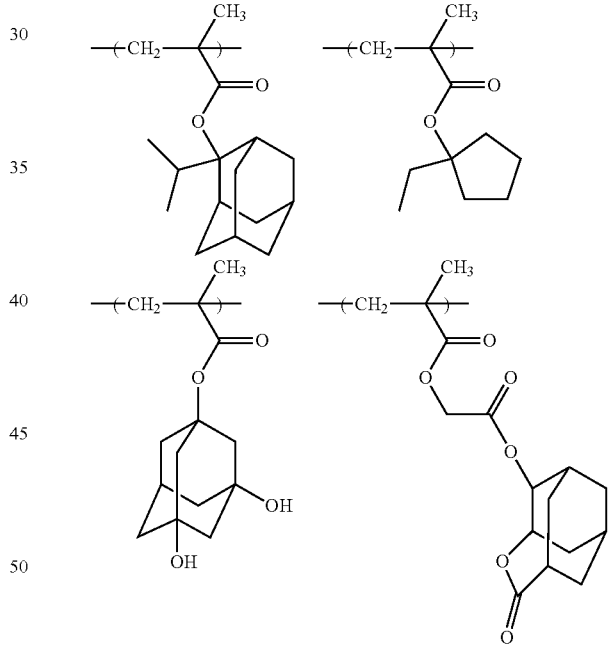

Synthesis Example 6

Synthesis of Resin A1-2

Monomer (a1-1-3), monomer (a1-2-9), monomer (a2-1-1) and monomer (a3-4-2) were mixed together with a mole ratio of monomer (a1-1-3), monomer (a1-2-9), monomer (a2-1-1) and monomer (a3-4-2)=45:14:2.5:38.5, and propyleneglycolmonomethylether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 1% by mole and 3% by mole respectively with respect to the total amount of monomers, and the resultant mixture was heated for about 5 hours at 73° C. Then, the obtained reaction mixture was poured into a large amount of a mixture of methanol and water to precipitate a resin. The obtained resin was filtrated. The obtained resin was dissolved in another propyleneglycolmonomethylether acetate to obtain a solution, and the solution was poured into a mixture of methanol and water to precipitate the resin. The obtained resin was filtrated. These operations were conducted twice to obtain the copolymer having a weight average molecular weight of about 7900 in 70% yield. This resin, which had the structural units of the following formulae, was referred to as Resin A1-2.

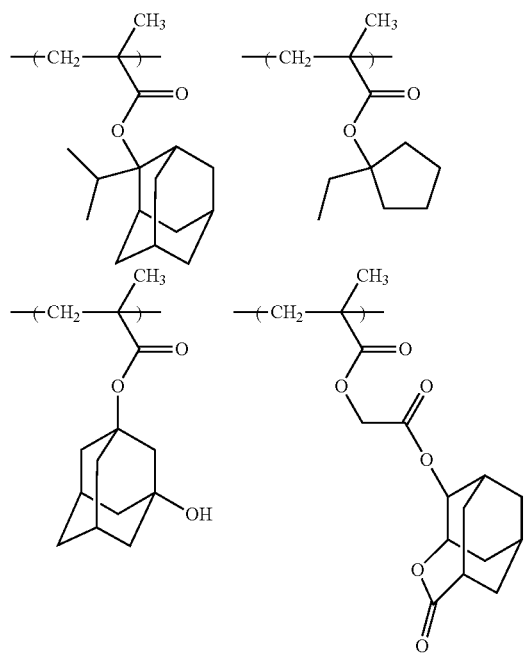

Example 2

Synthesis of Resin A2-1

To monomer (I-1), propyleneglycolmonomethylether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 0.7% by mole and 2.1% by mole respectively with respect to the total amount of monomers, and the resultant mixture was heated for about 5 hours at 75° C. Then, the obtained reaction mixture was poured into a large amount of a mixture of methanol and water to precipitate a resin. The obtained resin was filtrated. Thus obtained resin was poured into methanol to precipitate the resin. The obtained resin was filtrated to obtain the polymer having a weight average molecular weight of about 14000 in 80% yield. This resin, which had the structural units of the following formula, was referred to as Resin A2-1.

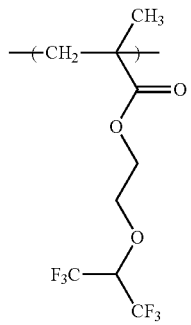

Example 3

Synthesis of Resin A2-2

Monomer (I-1) and monomer (a5-1-1) were mixed together with the mole ratio of monomer (I-1) and monomer (a5-1-1)=50:50, and propyleneglycolmonomethylether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 0.7% by mole and 2.1% by mole respectively with respect to the total amount of monomers, and the resultant mixture was heated for about 5 hours at 75° C. Then, the obtained reaction mixture was poured into a large amount of a mixture of methanol and water to precipitate a resin. The obtained resin was filtrated. Thus obtained resin was poured into methanol to precipitate the resin. The obtained resin was filtrated to obtain the copolymer having a weight average molecular weight of about 14000 in 86% yield. This resin, which had the structural units of the following formulae, was referred to as Resin A2-2.

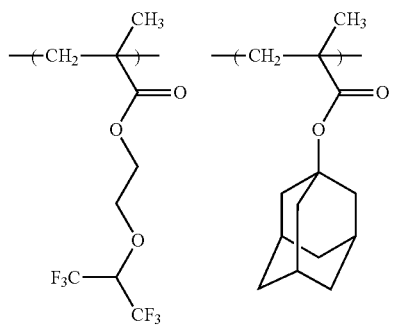

Synthesis Example 7

Synthesis of Resin A2-3

Monomer (1-7) and monomer (a5-1-1) were mixed together with the mole ratio of monomer (1-7) and monomer (a5-1-1)=50:50, and propyleneglycolmonomethylether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 0.7% by mole and 2.1% by mole respectively with respect to the total amount of monomers, and the resultant mixture was heated for about 5 hours at 75° C. Then, the obtained reaction mixture was poured into a large amount of a mixture of methanol and water to precipitate a resin. The obtained resin was filtrated. Thus obtained resin was poured into methanol to precipitate the resin. The obtained resin was filtrated to obtain the copolymer having a weight average molecular weight of about 13000 in 78% yield. This resin, which had the structural units of the following formulae, was referred to as Resin A2-3.

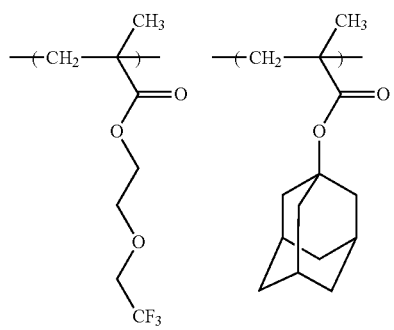

Example 4

Synthesis of Resin A2-4

Monomer (1-1), monomer (a4-0-12) and monomer (a5-1-1) were mixed together with the mole ratio of monomer (I-1), monomer (a4-0-12) and monomer (a5-1-1)=50:25:25, and propyleneglycolmonomethylether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 0.7% by mole and 2.1% by mole respectively with respect to the total amount of monomers, and the resultant mixture was heated for about 5 hours at 75° C. Then, the obtained reaction mixture was poured into a large amount of a mixture of methanol and water to precipitate a resin. The obtained resin was filtrated. Thus obtained resin was poured into methanol to precipitate the resin. The obtained resin was filtrated to obtain the copolymer having a weight average molecular weight of about 14000 in 73% yield. This resin, which had the structural units of the following formulae, was referred to as Resin A2-4.

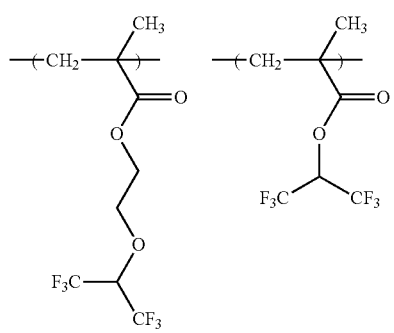

-continued

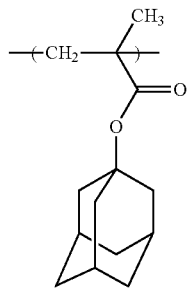

Example 5

Synthesis of Resin A2-5

Monomer (I-1) and monomer (a5-1-1) were mixed together with the mole ratio of monomer (I-1) and monomer (a5-1-1)=50:50, and propyleneglycolmonomethylether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 1% by mole and 3% by mole respectively with respect to the total amount of monomers, and the resultant mixture was heated for about 5 hours at 75° C. Then, the obtained reaction mixture was poured into a large amount of a mixture of methanol and water to precipitate a resin. The obtained resin was filtrated. Thus obtained resin was poured into methanol to precipitate the resin. The obtained resin was filtrated to obtain the copolymer having a weight average molecular weight of about 7900 in 76% yield. This resin, which had the structural units of the following formulae, was referred to as Resin A2-5.

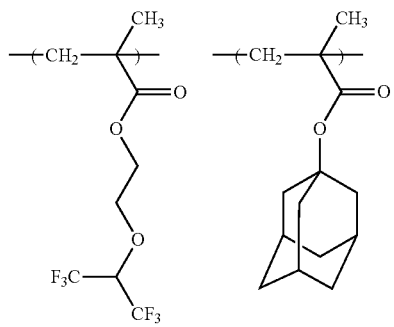

Synthesis Example 8

Synthesis of Resin A2-6

Monomer (1-8) and monomer (a5-1-1) were mixed together with the mole ratio of monomer (1-8) and monomer (a5-1-1)=50:50, and propyleneglycolmonomethylether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 0.7% by mole and 2.1% by mole respectively with respect to the total amount of monomers, and the resultant mixture was heated for about 5 hours at 75° C.

Then, the obtained reaction mixture was poured into a large amount of a mixture of methanol and water to precipitate a resin. The obtained resin was filtrated. Thus obtained resin was poured into methanol to precipitate the resin. The obtained resin was filtrated to obtain the copolymer having a weight average molecular weight of about 12000 in 70% yield. This resin, which had the structural units of the following formula, was referred to as Resin A2-6.

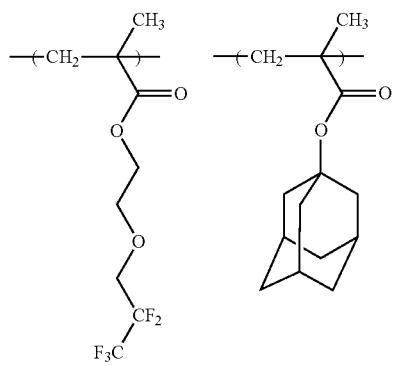

Synthesis Example 9

Synthesis of Resin A2-7

Monomer (I-8) and monomer (a5-1-1) were mixed together with the mole ratio of monomer (I-8) and monomer (a5-1-1)=50:50, and propyleneglycolmonomethylether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 1% by mole and 3% by mole respectively with respect to the total amount of monomers, and the resultant mixture was heated for about 5 hours at 75° C. Then, the obtained reaction mixture was poured into a large amount of a mixture of methanol and water to precipitate a resin. The obtained resin was filtrated. Thus obtained resin was poured into methanol to precipitate the resin. The obtained resin was filtrated to obtain the copolymer having a weight average molecular weight of about 7800 in 73% yield. This resin, which had the structural units of the following formulae, was referred to as Resin A2-7.

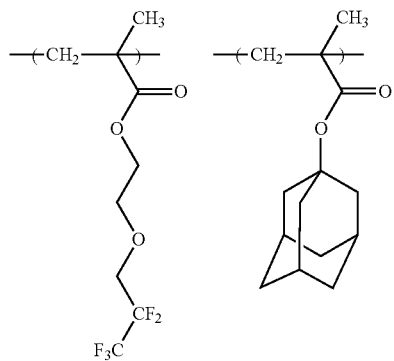

Synthesis Example 10

Synthesis of Resin AX2-1

To monomer (IX-1), propyleneglycolmonomethylether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 0.5% by mole and 1.5% by mole respectively with respect to the total amount of monomers, and the resultant mixture was heated for about 5 hours at 75° C. Then, the obtained reaction mixture was poured into a large amount of a mixture of methanol and water to precipitate a resin. The obtained resin was filtrated. Thus obtained resin was poured into methanol to precipitate the resin. The obtained resin was filtrated to obtain the polymer having a weight average molecular weight of about 32000 in 45% yield. This resin, which had the structural units of the following formula, was referred to as Resin AX2-1.

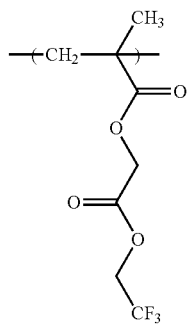

Synthesis Example 11

Synthesis of Resin AX2-2

Monomer (IX-2) and monomer (a1-2-x) were mixed together with the mole ratio of monomer (IX-2) and monomer (a1-2-x)=75:25, and propyleneglycolmonomethylether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 0.6% by mole and 2.4% by mole respectively with respect to the total amount of monomers, and the resultant mixture was heated for about 5 hours at 75° C. Then, the obtained reaction mixture was poured into a large amount of a mixture of methanol and water to precipitate a resin. The obtained resin was filtrated. Thus obtained resin was poured into methanol to precipitate the resin. The obtained resin was filtrated to obtain the copolymer having a weight average molecular weight of about 20000 in 58% yield. This resin, which had the structural units of the following formulae, was referred to as Resin AX2-2

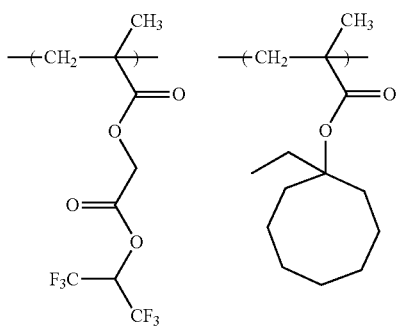

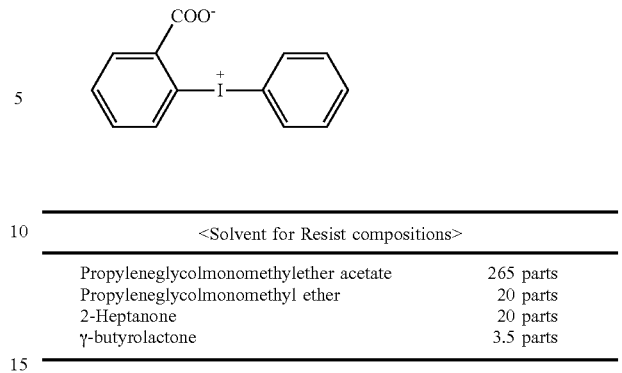

(Preparing Resist Compositions)

Resist compositions were prepared by mixing and dissolving each of the components shown in Table 1, and then filtrating through a fluororesin filter having 0.2 μm pore diameter. The obtained resist compositions were stored for 3 weeks at 30° C. Then, the properties of the resist compositions were evaluated.

TABLE 1

| Resist Comp. | Resin (parts) | Acid Generator (B) (parts) | Weakly Acidic Inner Salt (D) (parts) | PB/PEB (° C./° C.) |
|---|---|---|---|---|
| Composition 1 | A2-1/A1-1 = 0.5/10 | B1-21/B1-22 = 0.9/0.4 | D1 = 0.28 | 90/85 |
| Composition 2 | A2-1/A1-1 = 0.5/10 | B1-5/B1-22 = 0.4/0.4 | D1 = 0.28 | 90/85 |
| Composition 3 | A2-2/A1-1 = 0.5/10 | B1-21/B1-22 = 0.9/0.4 | D1 = 0.28 | 90/85 |
| Composition 4 | A2-3/A1-1 = 0.5/10 | B1-21/B1-22 = 0.9/0.4 | D1 = 0.28 | 90/85 |
| Composition 5 | A2-2/A1-1 = 0.5/10 | B1-21/B1-22 = 0.9/0.4 | C1 = 0.12 | 90/85 |
| Composition 6 | A2-2/A1-2 = 0.5/10 | B1-21/B1-22 = 0.9/0.4 | D1 = 0.28 | 90/85 |
| Composition 7 | A2-2/A1-2 = 0.4/10 | B1-21/B1-22 = 0.9/0.4 | D1 = 0.28 | 90/85 |
| Composition 8 | A2-4/A1-2 = 0.4/10 | B1-21/B1-22 = 0.9/0.4 | D1 = 0.28 | 90/85 |
| Composition 9 | A2-5/A1-2 = 0.4/10 | B1-21/B1-22 = 0.9/0.4 | D1 = 0.28 | 90/85 |
| Composition 10 | A2-6/A1-2 = 0.4/10 | B1-21/B1-22 = 0.9/0.4 | D1 = 0.28 | 90/85 |
| Composition 11 | A2-7/A1-2 = 0.4/10 | B1-21/B1-22 = 0.9/0.4 | D1 = 0.28 | 90/85 |
| Comparative Comp. 1 | AX2-1/A1-1 = 0.5/10 | B1-21/B1-22 = 0.9/0.4 | C1 = 0.12 | 90/85 |
| Comparative Comp. 2 | AX2-2/A1-1 = 0.5/10 | B1-21/B1-22 = 0.9/0.4 | C1 = 0.12 | |

<Resin>

A1-1, A1-2, A2-1 to A2-7, AX2-1, AX2-2: Resins A1-1, A1-2, A2-1 to A2-7, AX2-1, AX2-2 respectively, prepared by the method as described above <Acid Generator (B)>

B1-5: Salt represented by the formula (B1-5)

B1-21: Salt represented by the formula (B1-21)

B1-22: Salt represented by the formula (B1-22)

<Quencher>

C1: tri-n-pentylamine

D1: Compound as follow, a product of Tokyo Chemical Industry Co., LTD

| <Solvent for Resist compositions> | |
|---|---|
| Propyleneglycolmonomethylether acetate | 265 parts |
| Propyleneglycolmonomethyl ether | 20 parts |
| 2-Heptanone | 20 parts |
| γ-butyrolactone | 3.5 parts |

<Evaluation of Resist Compositions: Negative Resist Patterns>

A composition for an organic antireflective film ("ARC-29", by Nissan Chemical Co. Ltd.) was applied onto 12-inch silicon wafer [circular shape, diameter 12 inch] and baked for 60 seconds at 205° C. to form a 78 nm thick organic antireflective film.

One of the resist compositions was then applied thereon by spin coating in such a manner that the thickness of the film after drying (pre-baking) became 100 nm.

The obtained wafer was then pre-baked for 60 second on a direct hot plate at the temperature given in the "PB" column in Table 1.

On the wafers on which the composition layer had thus been formed, the film was then exposed through a mask for forming trench patterns (pitch 120 nm/trench width 40 nm) with changing exposure quantity stepwise, using an ArF excimer laser stepper for liquid-immersion lithography ("XT:1900Gi" by ASML Ltd.: NA=1.35, Annular oout=0.85 oin=0.65 XY-pol.). Ultrapure water was used as medium for liquid-immersion.

After the exposure, post-exposure baking was carried out for 60 seconds at the temperature given in the "PEB" column in Table 1.

Then, development was carried out with butyl acetate (a product of Tokyo Chemical Industry Co., LTD) at 23° C. for 20 seconds in the manner of dynamic dispensing method to obtain negative resist patterns.

Effective sensitivity was represented as the exposure quantity at which the resist pattern with 40 nm trench width was obtained.

(Line Edge Roughness (LER) Evaluation)

The wall surface of the resist pattern following the lithography process was observed using a scanning electron microscope.

The "o" was given when the irregularity in wall surface has a roughness width of 3 nm or less.

The "x" was given when the irregularity in wall surface has a roughness width of more than 3 nm.

Table 2 illustrates the results thereof. The figures in parentheses mean roughness width values (nm).

(Evaluation of Defects)

The negative patterns were produced in the same method described above except that the film was exposed through a mask for forming 1:1 line and space patterns (pitch 80 nm) with the exposure quantity at which the resist pattern with 1:1 line and space patterns was obtained using an ArF excimer laser stepper for liquid-immersion lithography ("XT:1900Gi" by ASML Ltd.: NA=1.35, ¾ Annular XY-pol.).

Thereafter, the number of defects was counted using a defect inspection apparatus (KLA-2360, KLA-Tencor Co. Ltd.)

Table 2 illustrates the results thereof.

TABLE 2

|  | Resist Composition | LER | Defects |
|---|---|---|---|
| Ex. 6 | Composition 1 | ○(2.87) | 170 |
| Ex. 7 | Composition 2 | ○(2.86) | 310 |
| Ex. 18 | Composition 3 | ○(2.74) | 190 |
| Ex. 19 | Composition 4 | ○(2.89) | 350 |
| Ex. 10 | Composition 5 | ○(2.98) | 260 |
| Ex. 11 | Composition 6 | ○(2.72) | 150 |
| Ex. 12 | Composition 7 | ○(2.71) | 170 |
| Ex. 13 | Composition 8 | ○(2.75) | 120 |
| Ex. 14 | Composition 9 | ○(2.69) | 180 |
| Ex. 15 | Composition 10 | ○(2.84) | 280 |
| Ex. 16 | Composition 11 | ○(2.83) | 290 |
| Comparative Ex. 1 | Comparative Comp. 1 | x(3.16) | 620 |
| Comparative Ex. 2 | Comparative Comp. 2 | x(3.42) | 360 |

The compound of the disclosure is useful as a resin for resist compositions. the The resist composition of the disclosure, which contains the resin, can provide resist patterns with less line edge roughness (LER) and reduced defects even after storage for a certain period. Therefore, the present resist composition can be used for semiconductor microfabrication.

What is claimed is:

1. A resist composition comprising
   (A1) a resin having an acid-labile group,
   (A2) a resin which comprises a structural unit represented by formula (I), and
   an acid generator:

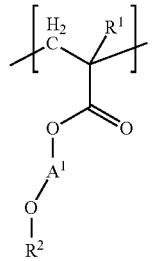

(I)

wherein $R^1$ represents a hydrogen atom, a halogen atom or a $C_1$, to $C_6$ alkyl group in which a hydrogen atom can be replaced by a halogen atom, $R^2$ represents a $C_1$, to $C_{12}$ fluorinated saturated hydrocarbon group, $A^1$ represents a $C_2$ to $C_6$ alkanediyl group or *-$A^2$-$X^1$-$(A^3$-$X^2)_a$-$A^4$-,

* represents a binding site to an oxygen atom in —O—CO—, $A^2$, $A^3$ and $A^4$ each independently represent a $C_1$ to $C_6$ alkanediyl group, $X^1$ and $X^2$ each independently represent —O—, —CO—O— or —O—CO—, and "a" represents 0 or 1.

2. The resist composition according to claim 1, wherein $A^1$ represents a $C_2$ to $C_6$ alkanediyl group.

3. The resist composition according to claim 1, wherein the resin (A2) comprises 50% by mole or more of the structural unit represented by formula (I).

4. The resist composition according to claim 1, wherein the resin (A2) is contained in the amount of 0.5 to 60 parts by mass with respect to 100 part by mass of the resin (A1).

5. The resist composition according to claim 1, further comprising a salt which generates an acid weaker in acidity than an acid generated from the acid generator.

6. A method for producing a resist pattern comprising steps (1) to (5);
   (1) applying the resist composition according to claim 1 onto a substrate;
   (2) drying the applied composition to form a composition layer;
   (3) exposing the composition layer;
   (4) heating the exposed composition layer, and
   (5) developing the heated composition layer.

7. A compound represented by formula (Ia):

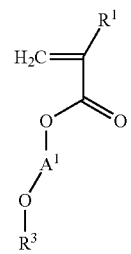

(Ia)

wherein $R^1$ represents a hydrogen atom, a fluorine atom or a $C_1$ to $C_6$ alkyl group in which a hydrogen atom can be replaced by a fluorine atom, $R^3$ represents —CH($R^{f1}$)($R^{f2}$), $R^{f1}$ and $R^{f2}$ each independently represent a $C_1$ to $C_6$ perfluoroalkyl group, $A^1$ represents a $C_2$ to $C_6$ alkanediyl group or *-$A^2$-$X^1$-$(A^3$-$X^2)_a$-$A^4$-,

* represents a binding site to an oxygen atom in —O—CO—, $A^2$, $A^3$ and $A^4$ each independently represent a $C_1$ to $C_6$ alkanediyl group, $X^1$ and $X^2$ each independently represent —O—, —CO—O— or —O—CO—, and "a" represents 0 or 1.

8. A resin comprising a structural unit derived from the compound according to claim 7.

* * * * *